(12) United States Patent
Kakhlon et al.

(10) Patent No.: US 11,891,381 B2
(45) Date of Patent: Feb. 6, 2024

(54) COMPOUNDS FOR THE TREATMENT OF GLYCOGEN STORAGE DISORDERS

(71) Applicants: HADASIT MEDICAL RESEARCH SERVICES AND DEVELOPMENT LTD., Jerusalem (IL); RAMOT AT TEL-AVIV UNIVERSITY LTD., Tel Aviv (IL)

(72) Inventors: Or Kakhlon, Jerusalem (IL); Miguel Enrique Weil, Tel-Aviv (IL); Leonardo Javier Solmesky, Yavne (IL)

(73) Assignees: HADASIT MEDICAL RESEARCH SERVICES AND DEVELOPMENT LTD., Jerusalem (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 39 days.

(21) Appl. No.: 17/334,905

(22) Filed: May 31, 2021

(65) Prior Publication Data

US 2021/0395237 A1    Dec. 23, 2021

Related U.S. Application Data

(62) Division of application No. 16/485,577, filed as application No. PCT/IL2018/050207 on Feb. 22, 2018, now Pat. No. 11,053,231.

(60) Provisional application No. 62/461,884, filed on Feb. 22, 2017.

(51) Int. Cl.
| C07D 409/12 | (2006.01) |
| A61P 25/28 | (2006.01) |
| C07D 487/08 | (2006.01) |

(52) U.S. Cl.
CPC ............ *C07D 409/12* (2013.01); *A61P 25/28* (2018.01); *C07D 487/08* (2013.01)

(58) Field of Classification Search
CPC .................................................. C07D 409/12
USPC ........................................................ 514/221
See application file for complete search history.

(56) References Cited

U.S. PATENT DOCUMENTS

| 2006/0122256 A1 | 6/2006 | Gillespie et al. |
| 2011/0112161 A1 | 5/2011 | Bolin et al. |
| 2011/0118314 A1 | 5/2011 | Yun |

FOREIGN PATENT DOCUMENTS

| WO | 2006058648 | 6/2006 |
| WO | WO2011035064 A2 * | 3/2011 |
| WO | 2011057959 | 5/2011 |
| WO | 2011058122 | 5/2011 |
| WO | 2016161086 | 10/2016 |

OTHER PUBLICATIONS

Berge, et al., "Pharmaceutical Salts", Journal of Pharmaceutical Sciences, vol. 66(1), 1-19. (1977).
CAS Registry No. 1257155-76-2, CA Index Name: 4-Pyridinecarboxamide, 1,2-dihydro-N-(2-methoxyethyl)-6-methyl-N-[(3-methyl-2-thienyl)methyl]-2-oxo-, Entered STN: Dec. 20, 2010.
PubChem CID: 50955298, Create Date: Mar. 29, 2011, URL: <https://pubchem.ncbi.nlm.nih.gov/compound/50955298> Mar. 28, 2011 (Mar. 28, 2011).
CAS Registry No. 1523531-28-3, CA Index Name: 3,9-Diazabicyclo[4.2.1]nonan-4-one,9-[[4-(methoxymethyl)-5-methyl-3-isoxazolyl]carbonyl]-3-methyl-, (1S,6R)-, Entered STN: Jan. 18, 2014.
PubChem CID: 56720648, Create Date: Mar. 8, 2012, URL: <https://pubchem.ncbi.nlm.nih.gov/compound/56720648> Mar. 8, 2012 (Mar. 8, 2012).
Pederson, et al., "Inhibiting Glycogen Synthesis Prevents Lafora Disease in a Mouse Model", Annals of Neurology (Aug. 1, 2013);74(2), pp. 297-300.
Berthier, et al., "Pharmacological Interventions to Ameliorate Neuropathological Symptoms in a Mouse Model of Lafora Disease", Molecular Neurobiology (Mar. 1, 2016); 53(2), pp. 1296-1309.
Solmesky, et al., "A novel image-based high-throughput screening assay discovers therapeutic candidates for adult polyglucosan body disease", Biochemical Journal (Oct. 15, 2017); 474(20), pp. 3403-3420.
PubChem AID: 1259354; "Small-molecule inhibitors of ST2 (IL1RL1)"; External ID ST2_IL33_Inhibitors_Primary_Screening_77700; Paczesny and Yang Labs, IUPUI and University of Michigan (Jan. 15, 2018). URL: <https://pubchem.ncbi.nlm.nih.gov/bioassay/1259354>.
International Search Report, International Application No. PCT/IL2018/050207, dated Jun. 7, 2018.
PCT Written Opinion for International Application No. PCT/IL2018/050207, dated Jun. 7, 2018, 9 pp.
PCT Preliminary Report on Patentability for International Application No. PCT/IL2018/050207, dated Aug. 27, 2018, 10 pp.

* cited by examiner

*Primary Examiner* — Taofiq A Solola
(74) *Attorney, Agent, or Firm* — The Roy Gross Law Firm, LLC; Roy Gross

(57) ABSTRACT

Compounds represented by general Formulae I to IV as described herein are disclosed. Further disclosed are composition utilizing the herein disclosed compounds and using the same for the treatment of glycogen storage disorders.

10 Claims, 91 Drawing Sheets

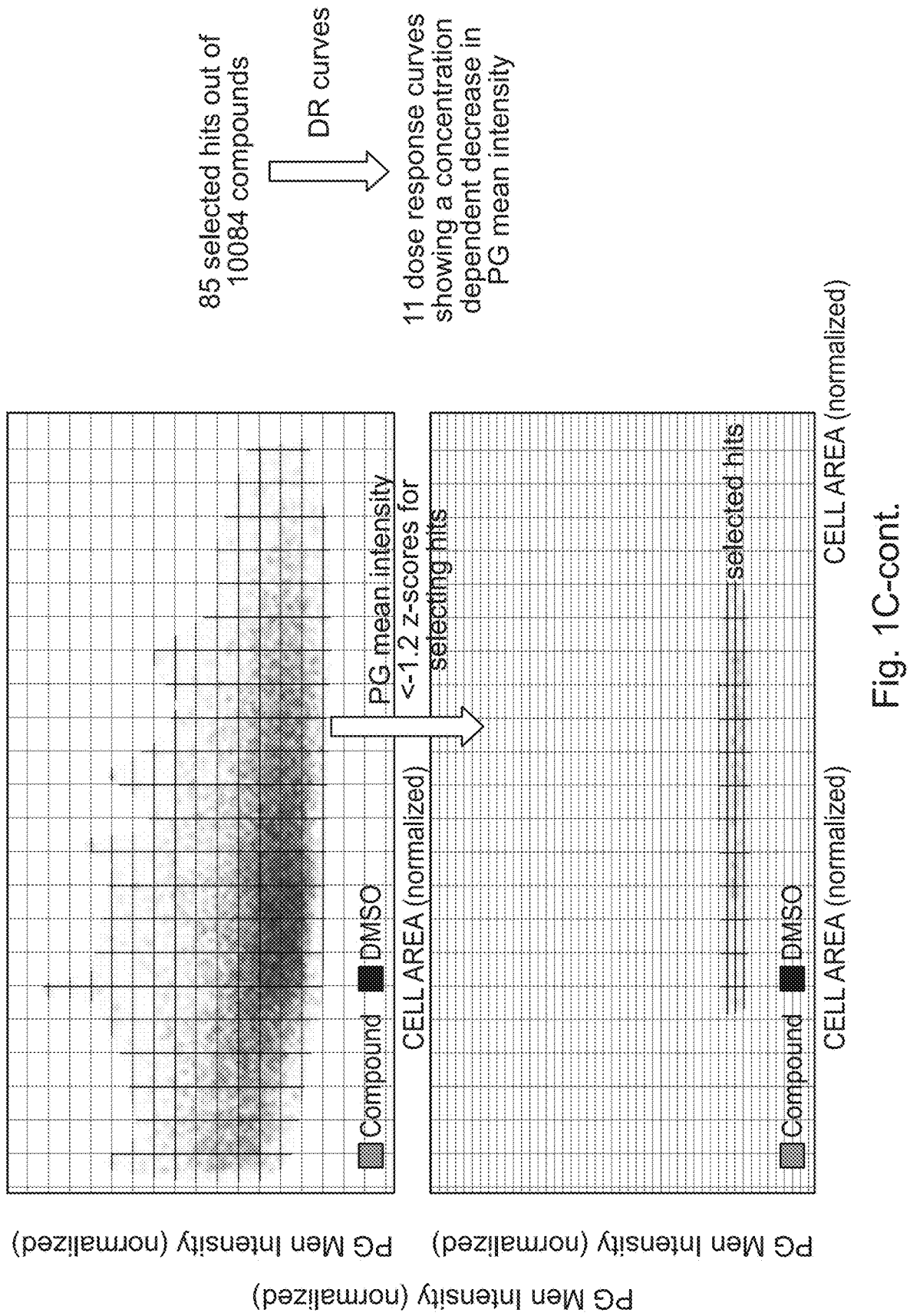
Fig. 1C-cont.

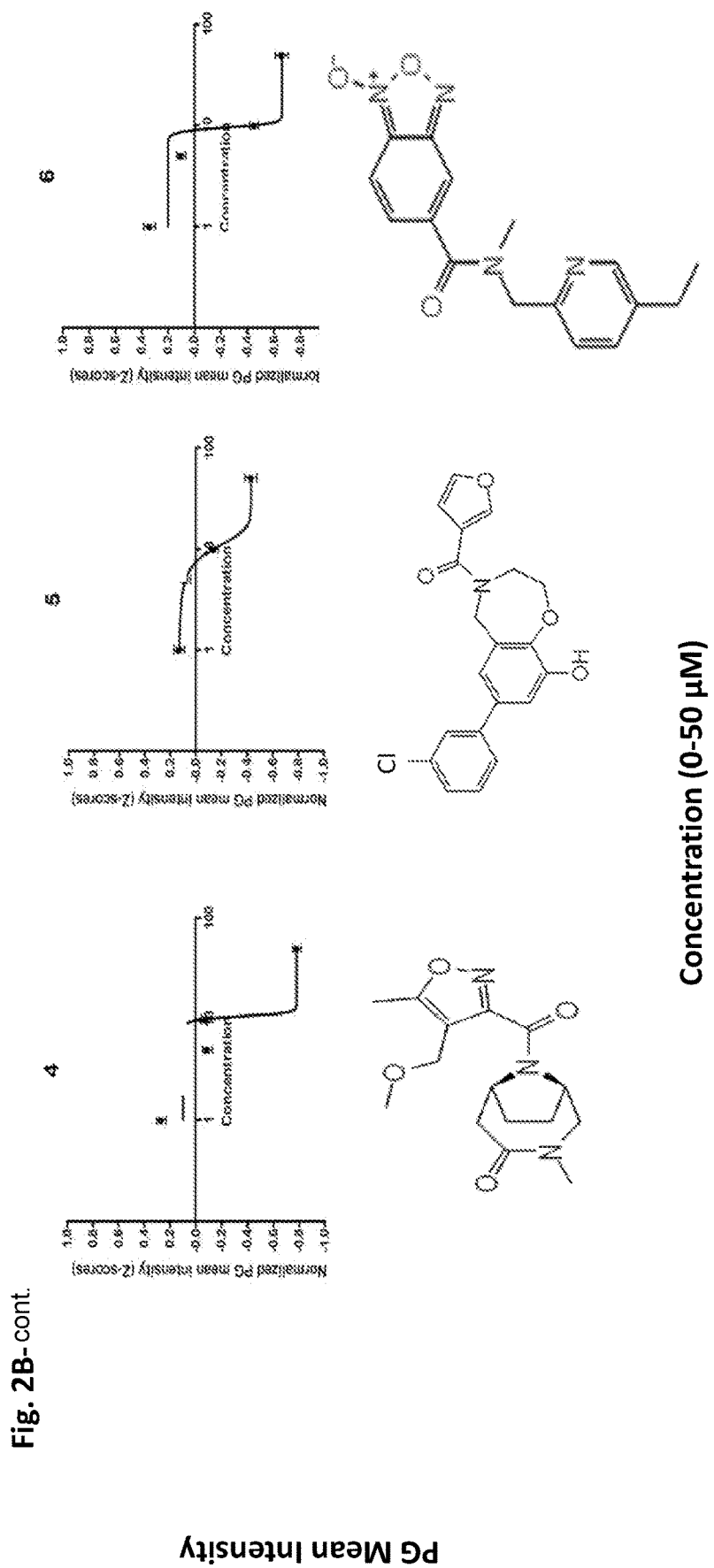
Fig. 2B-cont.

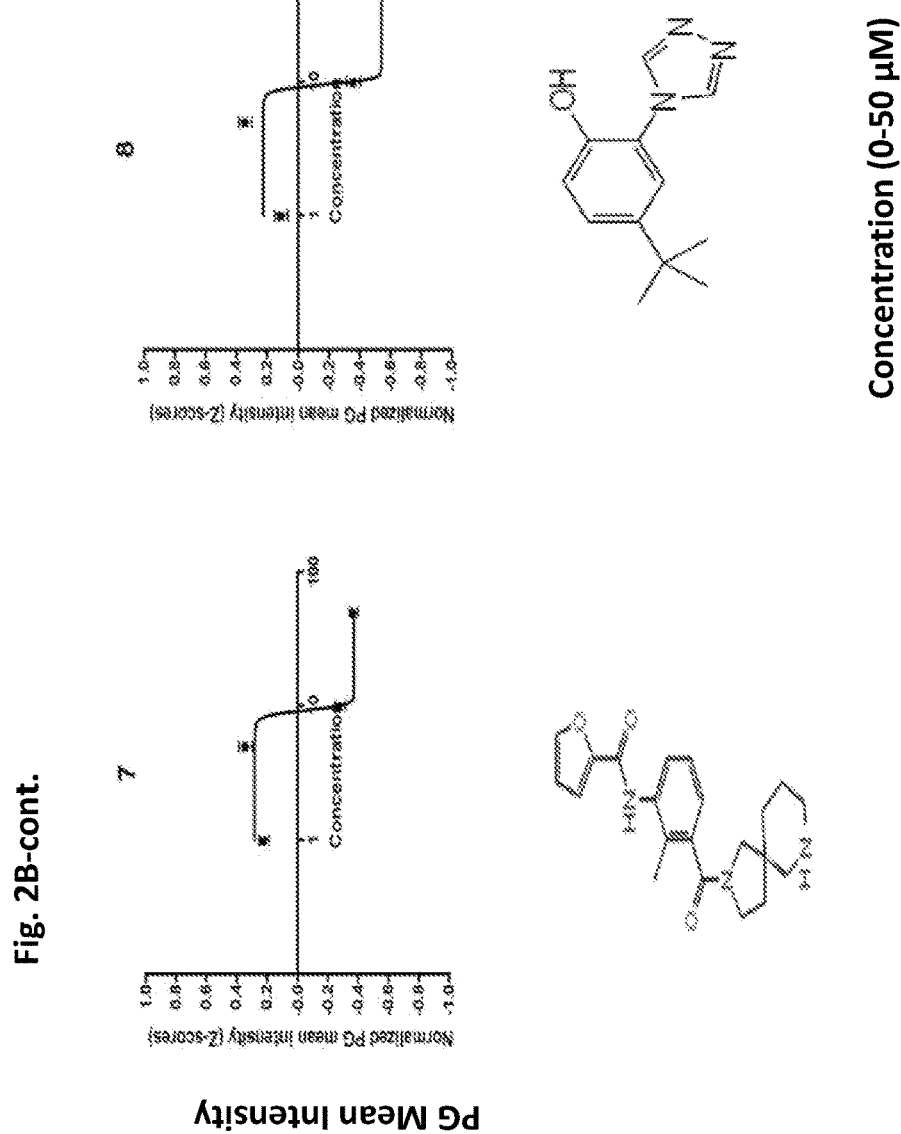
Fig. 2B-cont.

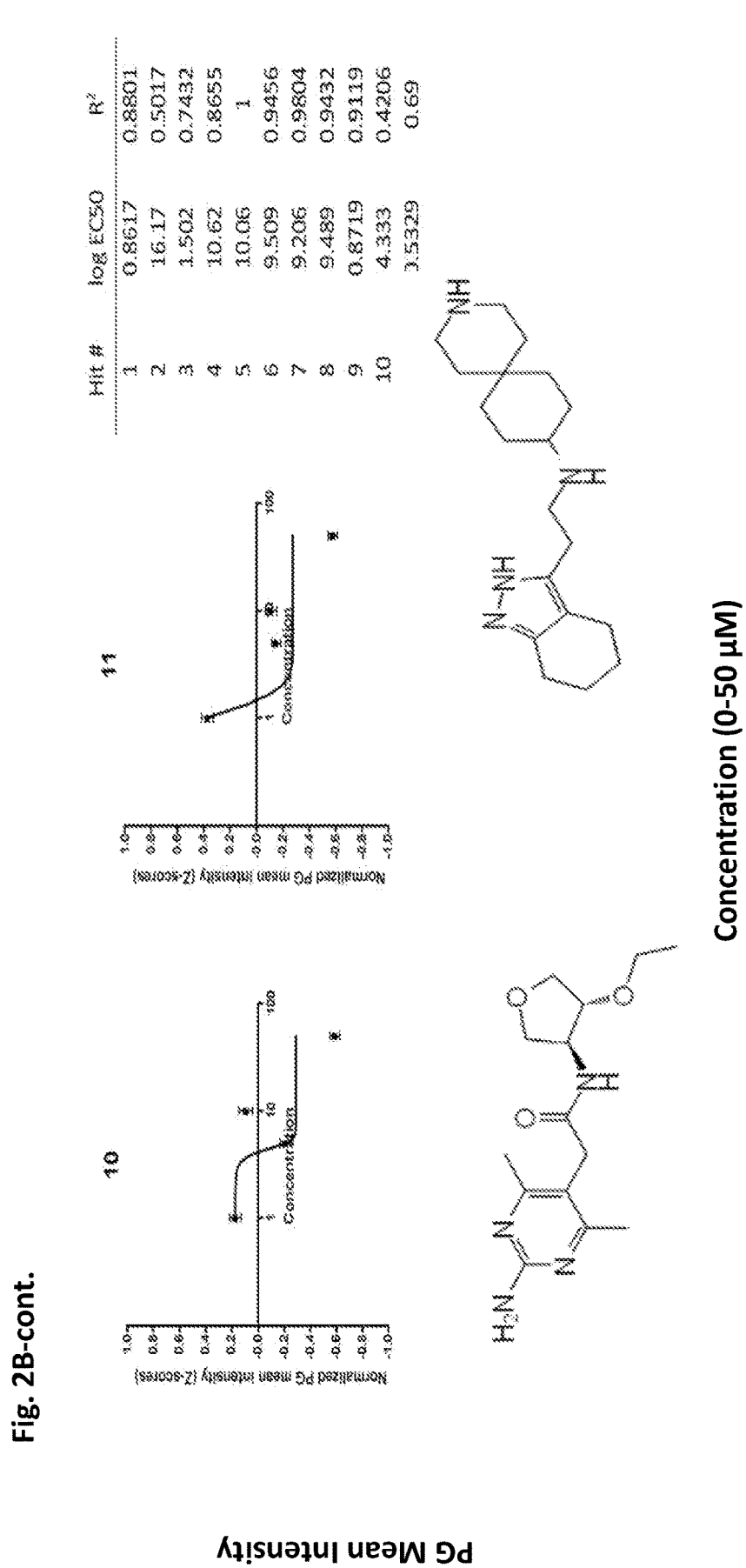
Fig. 2B-cont.

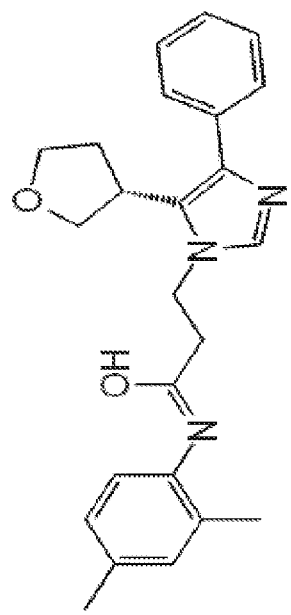
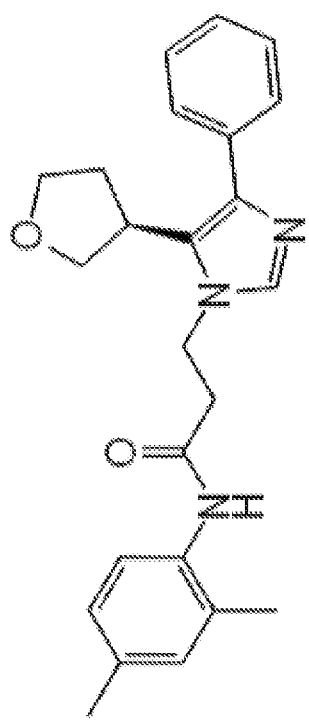
Fig. 2C

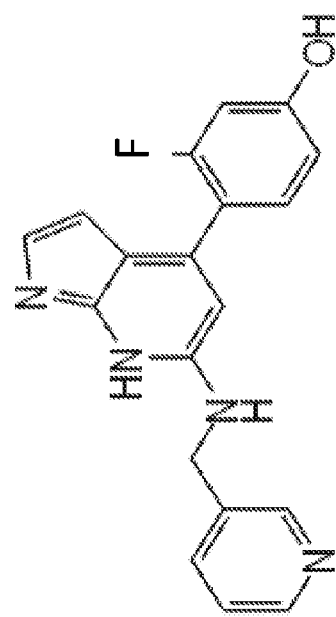
Compound 4
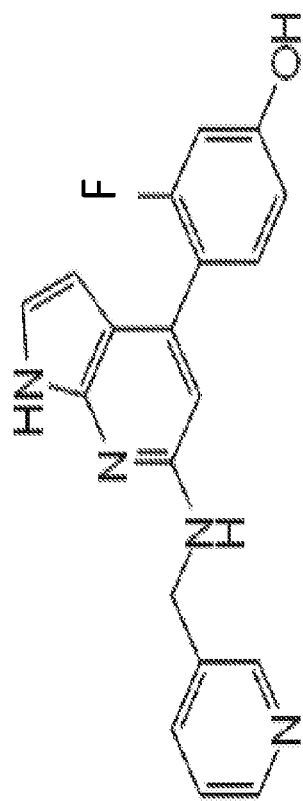
Compound 3
Fig. 2C-cont.

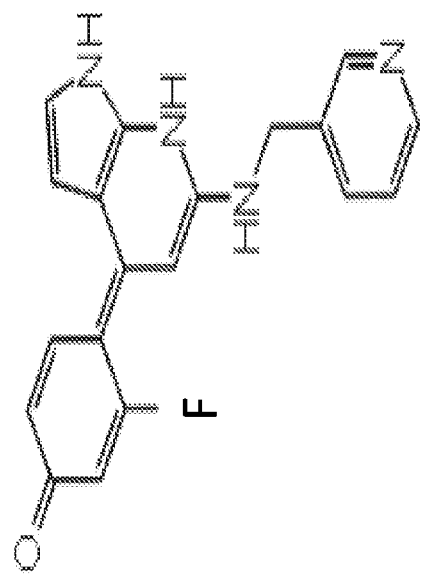
Compound 6
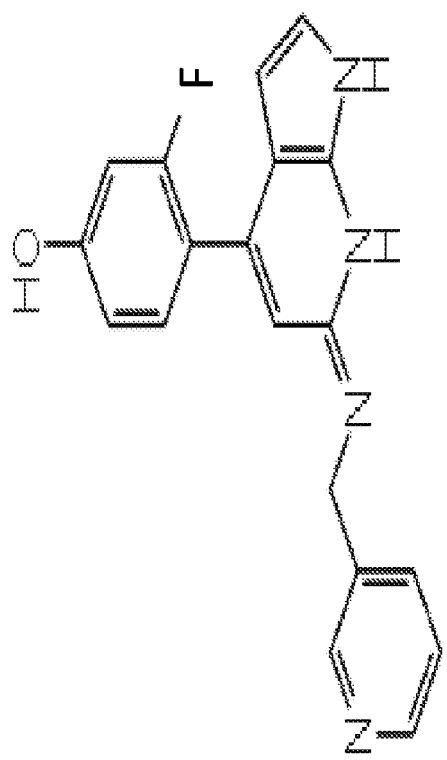
Compound 5
Fig. 2C-cont.

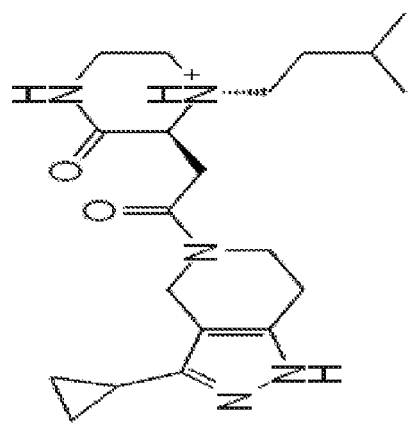
Compound 8
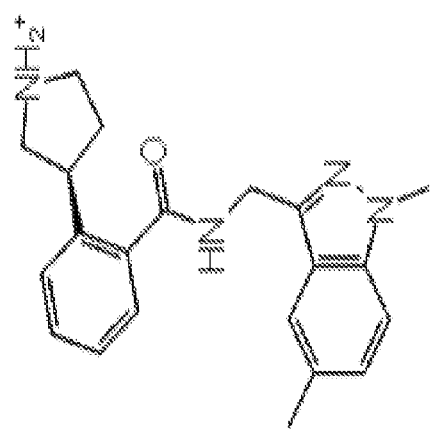
Compound 7
Fig. 2C-cont.

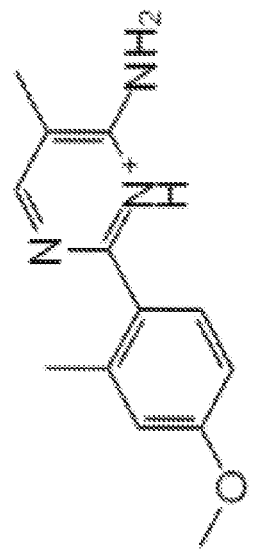
Compound 10
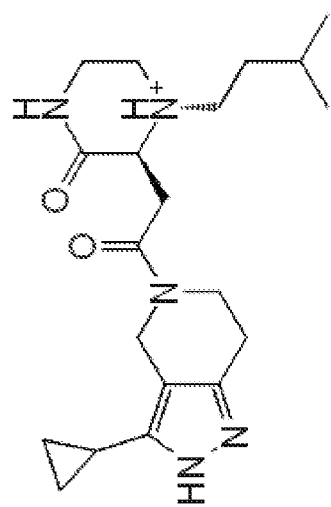
Compound 9
Fig. 2C-cont.

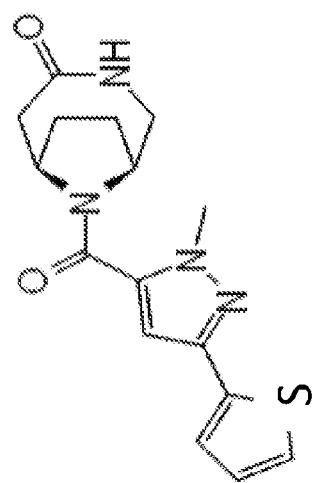
Compound 12
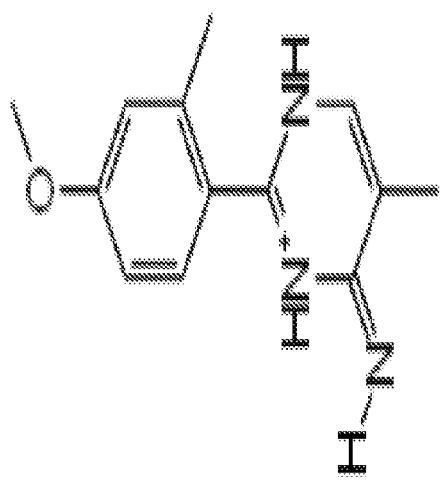
Compound 11
Fig. 2C-cont.

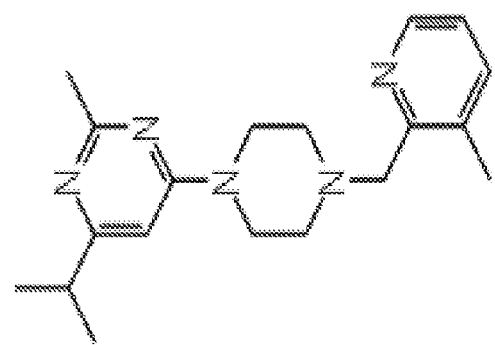
Compound 14
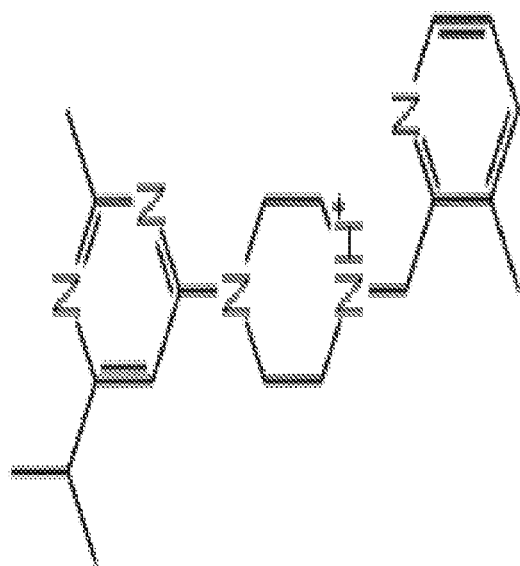
Compound 13
Fig. 2C-cont.

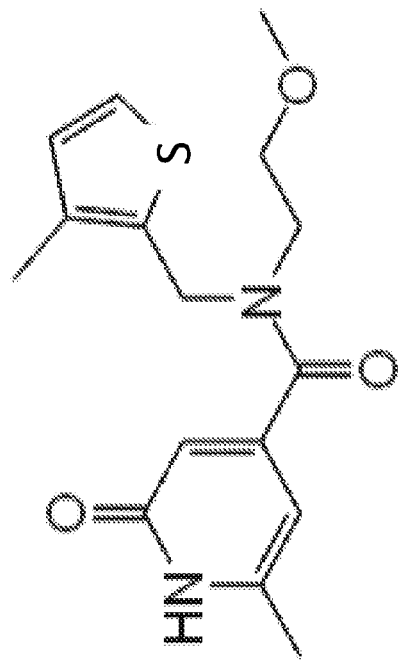
Compound 16
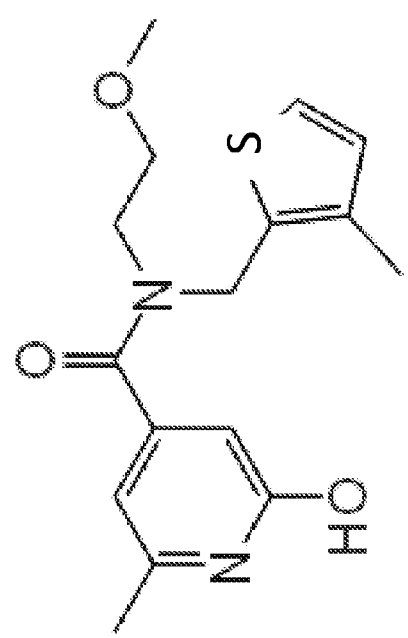
Compound 15
Fig. 2C-cont.

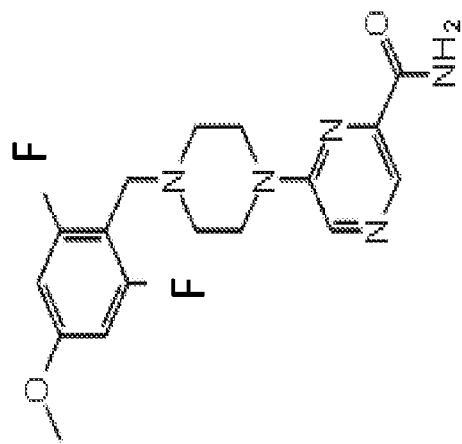
Compound 18
Fig. 2C-cont.
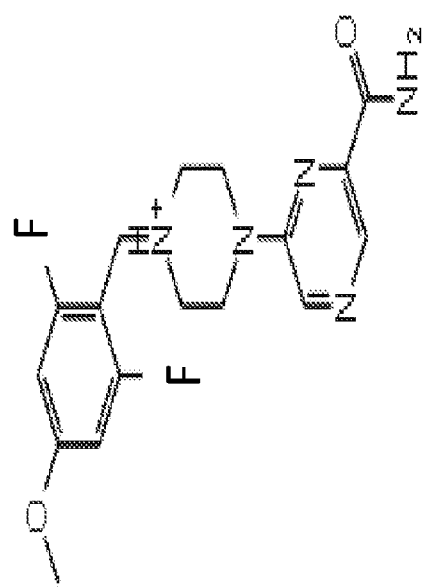
Compound 17

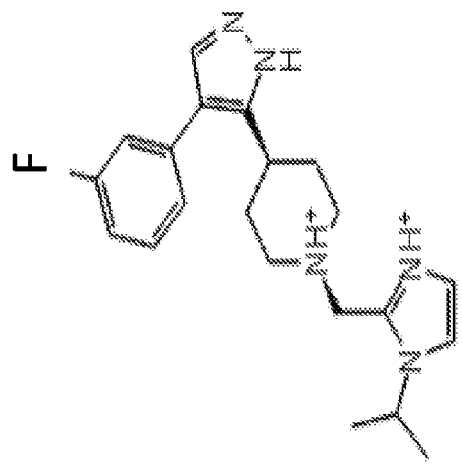
Compound 20
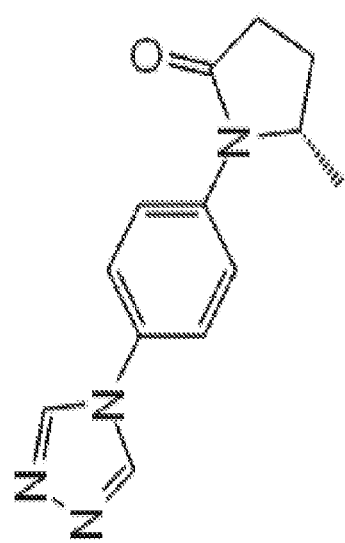
Compound 19
Fig. 2C-cont.

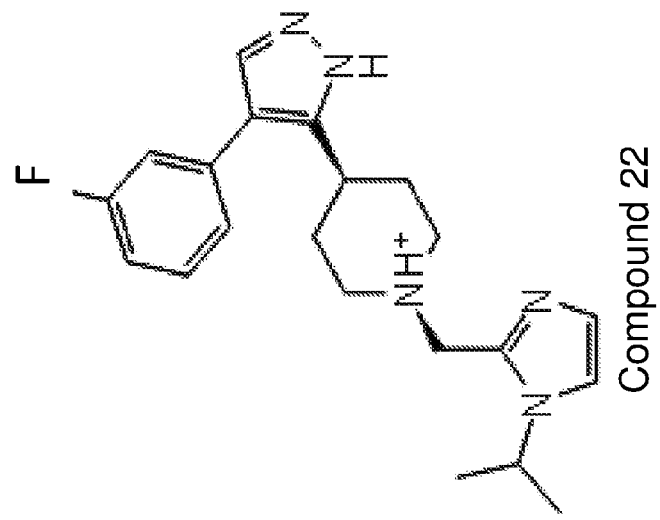
Fig. 2C-cont.

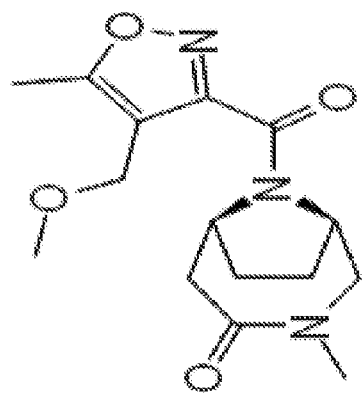
Compound 24
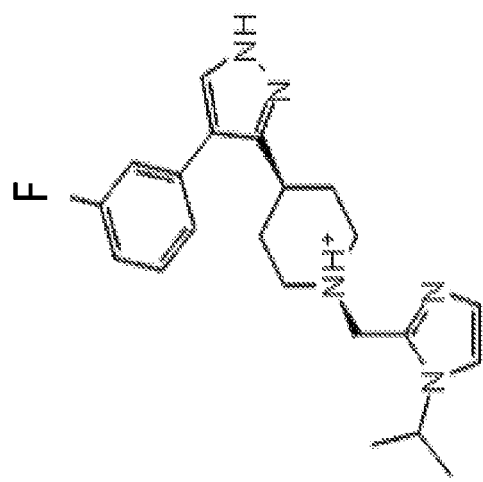
Compound 23
Fig. 2C-cont.

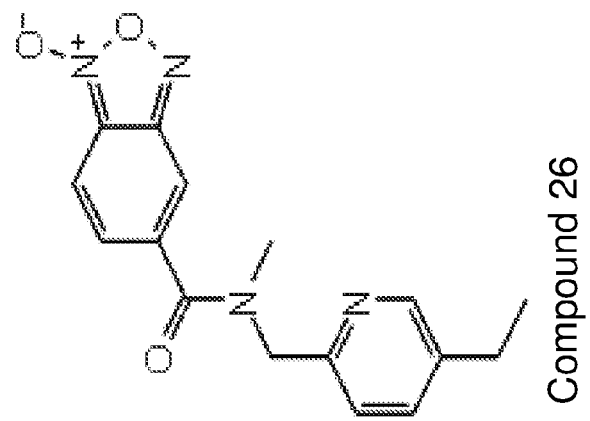
Compound 26
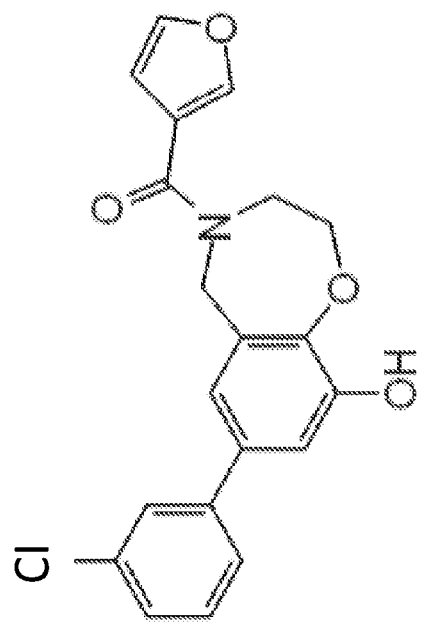
Compound 25
Fig. 2C-cont.

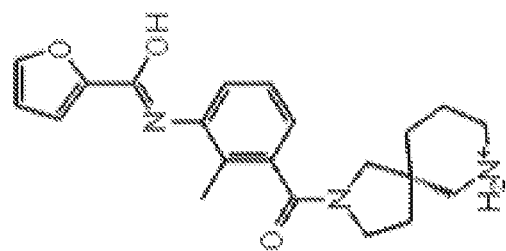
Compound 28
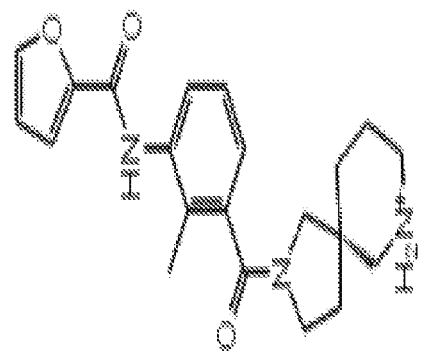
Compound 27
Fig. 2C-cont.

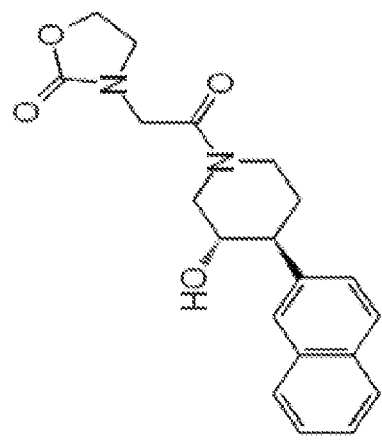
Compound 30
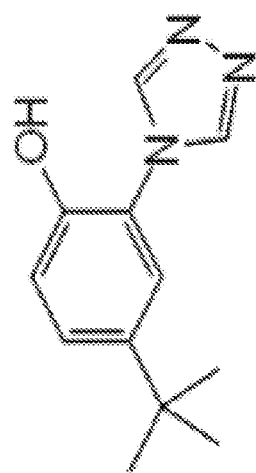
Compound 29
Fig. 2C-cont.

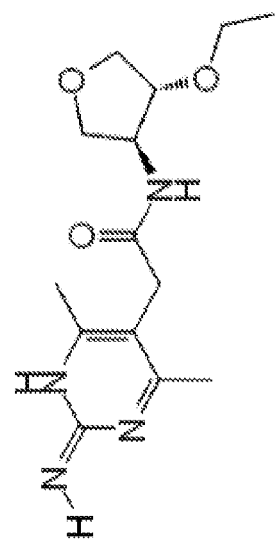
Compound 32
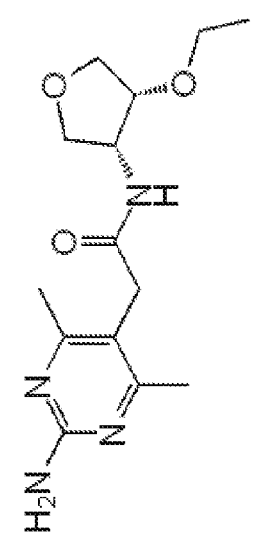
Compound 31
Fig. 2C-cont.

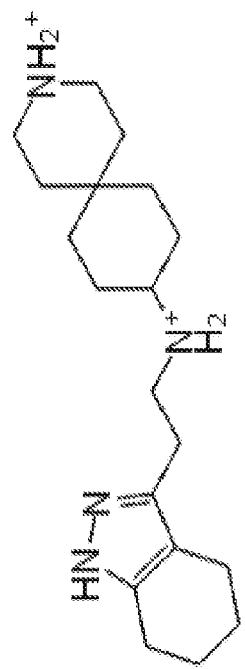
Compound 34
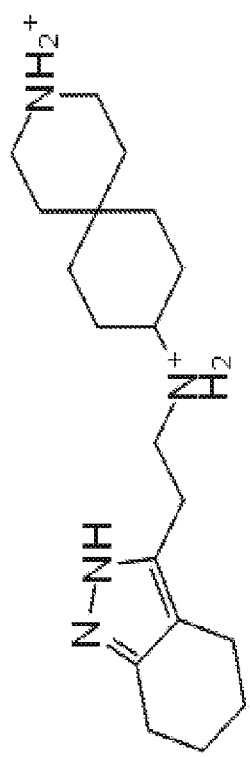
Compound 33
Fig. 2C-cont.

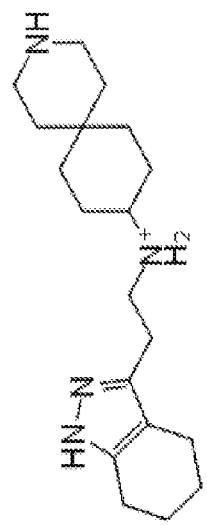
Compound 36
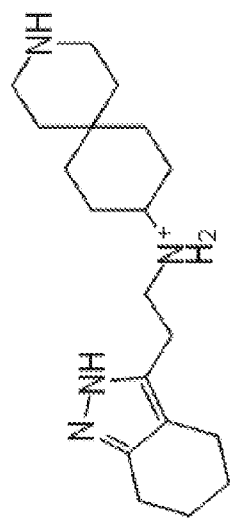
Compound 35
Fig. 2C-cont.

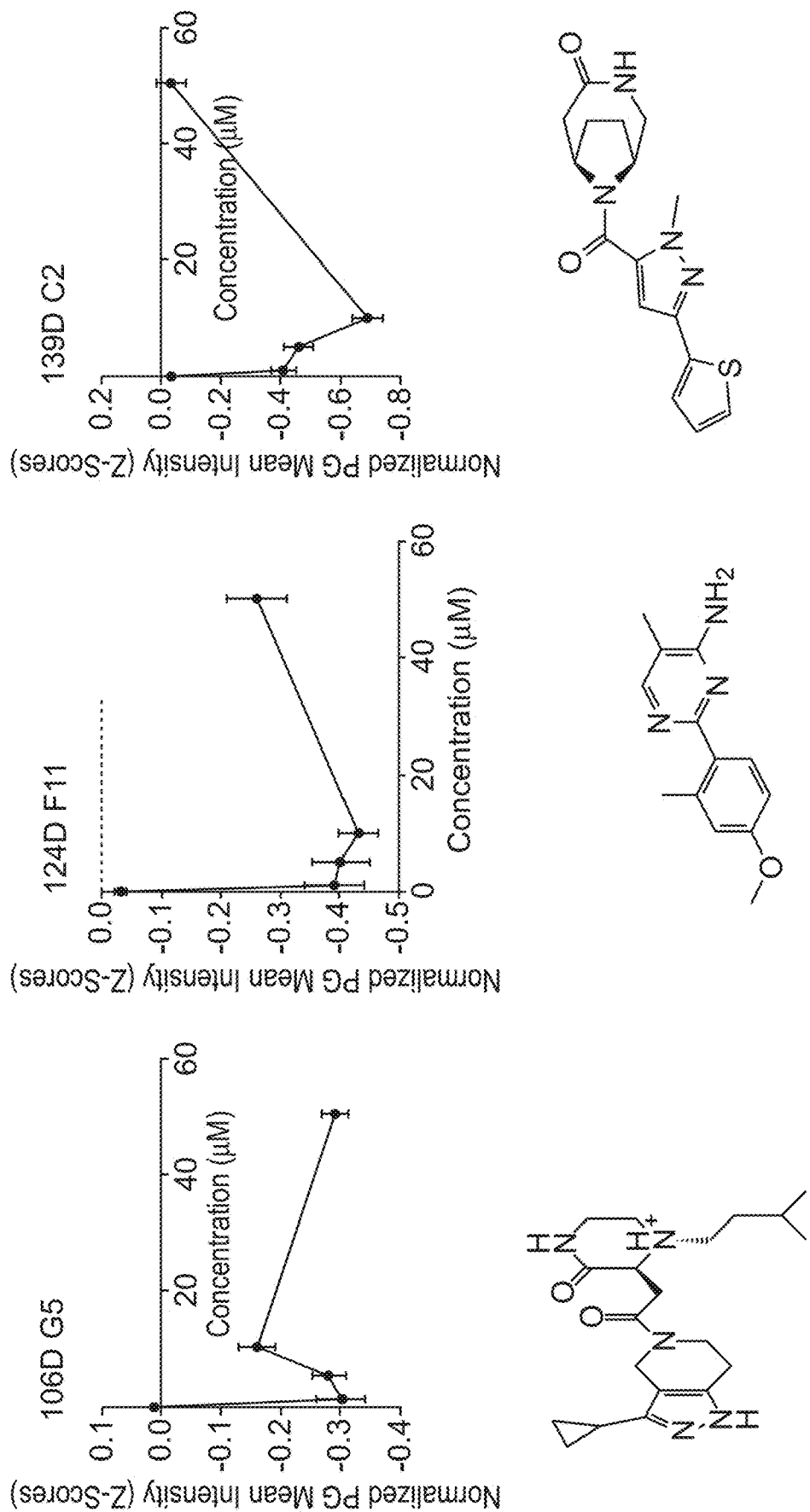
Fig. 3B-cont.

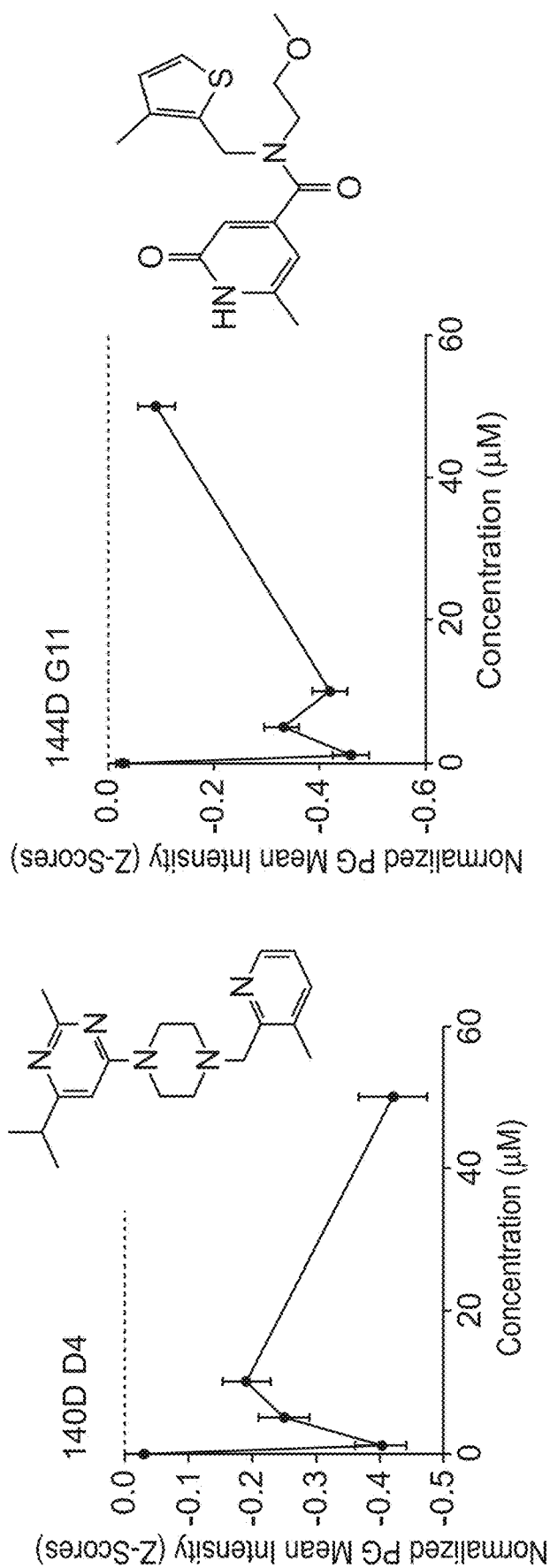
Fig. 3B-cont.

| Structure | Hit number and Name | Rank of Similarity to PP1 Interacting Drugs | Rank of Efficacy of GS Inhibition | % activity remaining |
|---|---|---|---|---|
| | UDP (positive control for GS) | Irrelevant. Not a hit. | 1 | 47.6 |
| 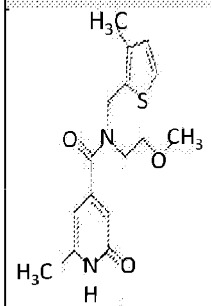 | #4: N-(2-methoxyethyl)-6-methyl-N-[(3-methyl-2-thienyl)methyl]-2-oxo-1,2-dihydropyridine-4-carboxamide | 3 | 2 | 67.7 |
| 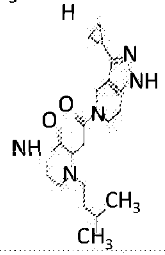 | #3: 3-[2-(3-cyclopropyl-1,4,6,7-tetrahydro-5H-pyrazolo[4,3-c]pyridin-5-yl)-2-oxoethyl]-4-(3-methylbutyl)-2-piperazinone | Below cutoff | 3 | 69.0 |
| 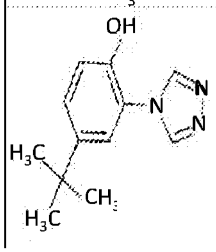 | #14: 4-tert-butyl-2-(4H-1,2,4-triazol-4-yl)phenol | Below cutoff | 4 | 72.3 |

Fig. 4B

| | 4 | 5 | 6 | 7 |
|---|---|---|---|---|
| #17: N-[3-(2,7-diazaspiro[4.5]dec-2-ylcarbonyl)-2-methylphenyl]-2-furamide | | | | 73.3 |
| #13: 2-(2-amino-4,6-dimethylpyrimidin-5-yl)-N-[(3S*,4R*)-4-ethoxytetrahydrofuran-3-yl]acetamide | Below cutoff | | | 73.5 |
| #1: 3-fluoro-4-{6-[(pyridin-3-ylmethyl)amino]-1H-pyrrolo[2,3-b]pyridin-4-yl}phenol | Below cutoff | | | 77.3 |

Fig. 4B-Cont.

| | | | |
|---|---|---|---|
| 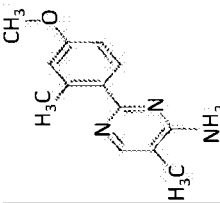 #16: 2-(4-methoxy-2-methylphenyl)-5-methylpyrimidin-4-amine | Below cutoff | | |
| 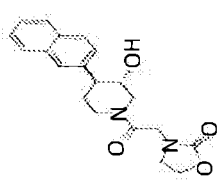 #5: 3-{2-[(3S*,4S*)-3-hydroxy-4-(2-naphthyl)piperidin-1-yl]-2-oxoethyl}-1,3-oxazolidin-2-one | 1 | 8 | 82.1 |
| | | 9 | 86.5 |
| 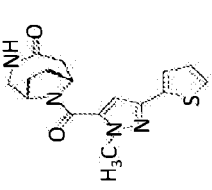 #9: (1S*,6R*)-9-{[1-methyl-3-(2-thienyl)-1H-pyrazol-5-yl]carbonyl}-3,9-diazabicyclo[4.2.1]nonan-4-one | Below cutoff | 10 | 87.1 |
Fig. 4B-Cont.

| | | |
|---|---|---|
|  #11: N-[(5-ethylpyridin-2-yl)methyl]-N-methyl-2,1,3-benzoxadiazole-5-carboxamide 1-oxide | Below cutoff | 11 | 90.5 |
|  #2: 6-[4-(2,6-difluoro-4-methoxybenzyl)piperazin-1-yl]pyrazine-2-carboxamide | Below cutoff | 12 | 91.4 |
| 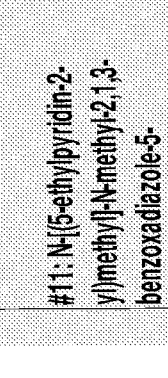 #15: N-[2-(4,5,6,7-tetrahydro-2H-indazol-3-yl)ethyl]-3-azaspiro[5.5]undecan-9-amine | Below cutoff | 13 | 93.6 |
FIG. 4B-Cont.

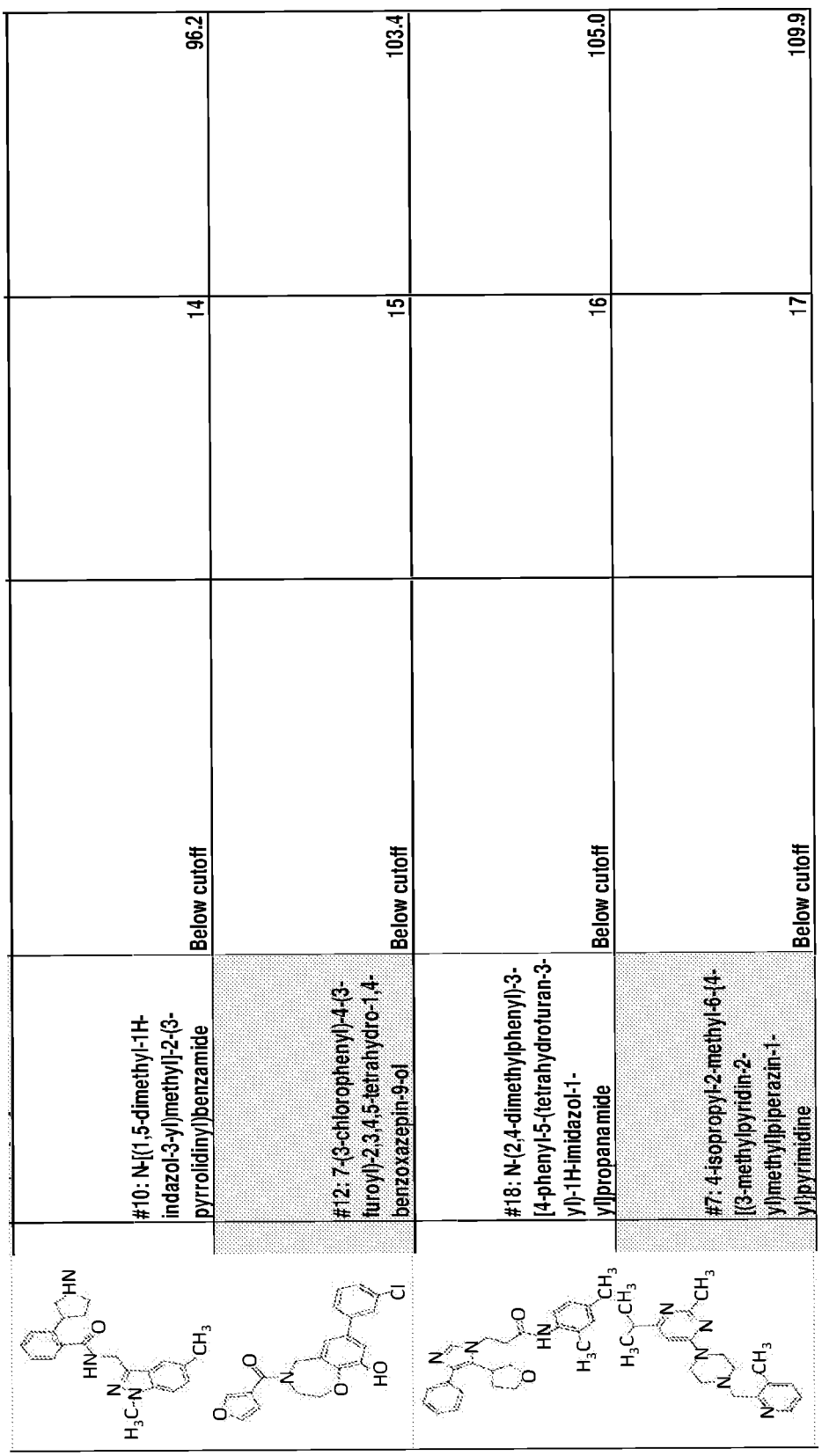
Fig. 4B-Cont

| | | | |
|---|---|---|---|
| ![structure] #19: (1S*,6R*)-9-[(4-(methoxymethyl)-5-methylisoxazol-3-yl]carbonyl]-3-methyl-3,9-diazabicyclo[4.2.1]nonan-4-one | 2 | 18 | 114.2 |
| ![structure] #8: 5-methyl-1-[4-(4H-1,2,4-triazol-4-yl)phenyl]pyrrolidin-2-one | Below cutoff | 19 | 115.4 |
| ![structure] #6: 4-[4-(3-fluorophenyl)-1H-pyrazol-5-yl]-1-[(1-isopropyl-1H-imidazol-2-yl)methyl]piperidine | Below cutoff | 20 | 118.3 |

Fig. 4B-Cont.

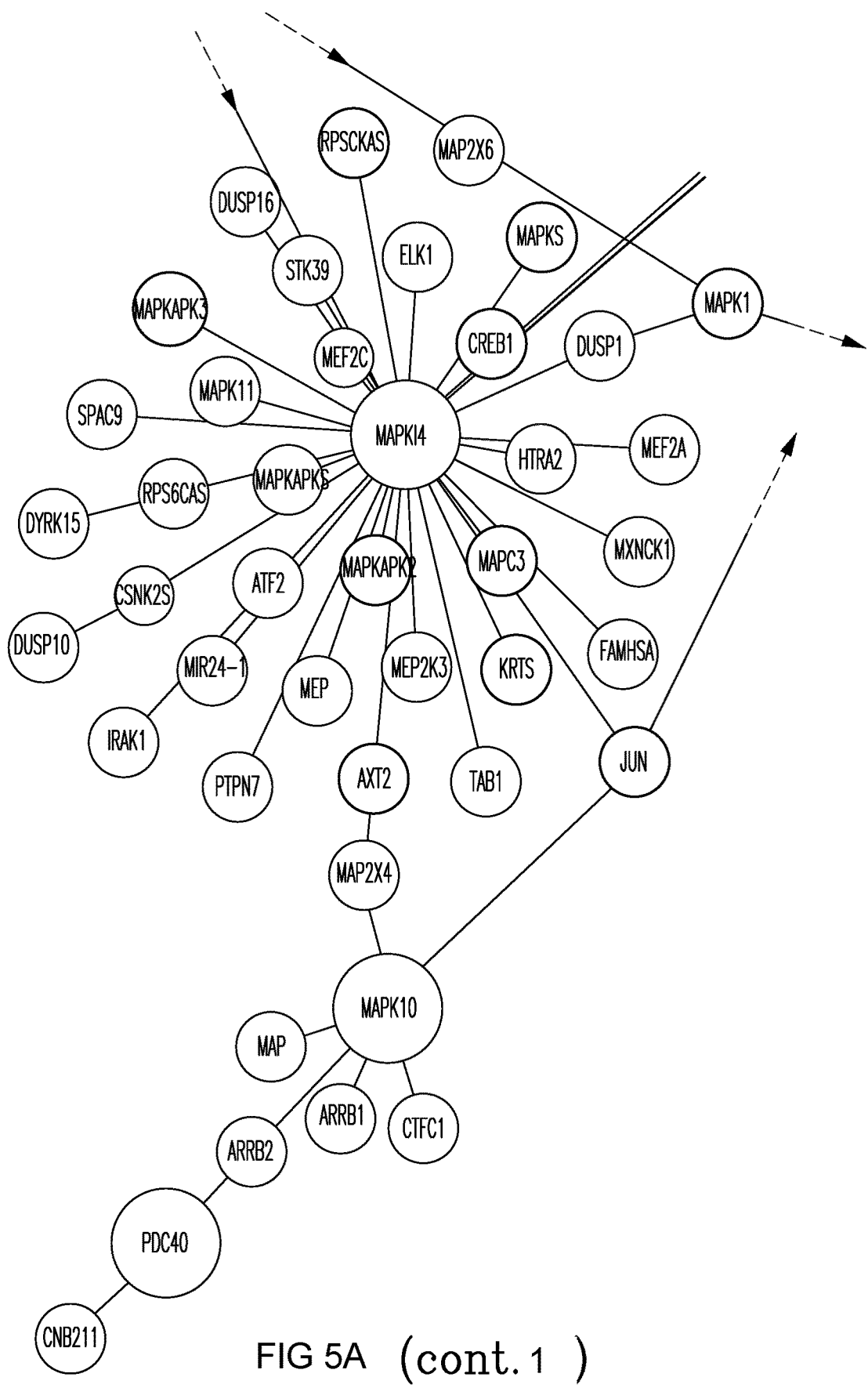
FIG 5A (cont. 1)

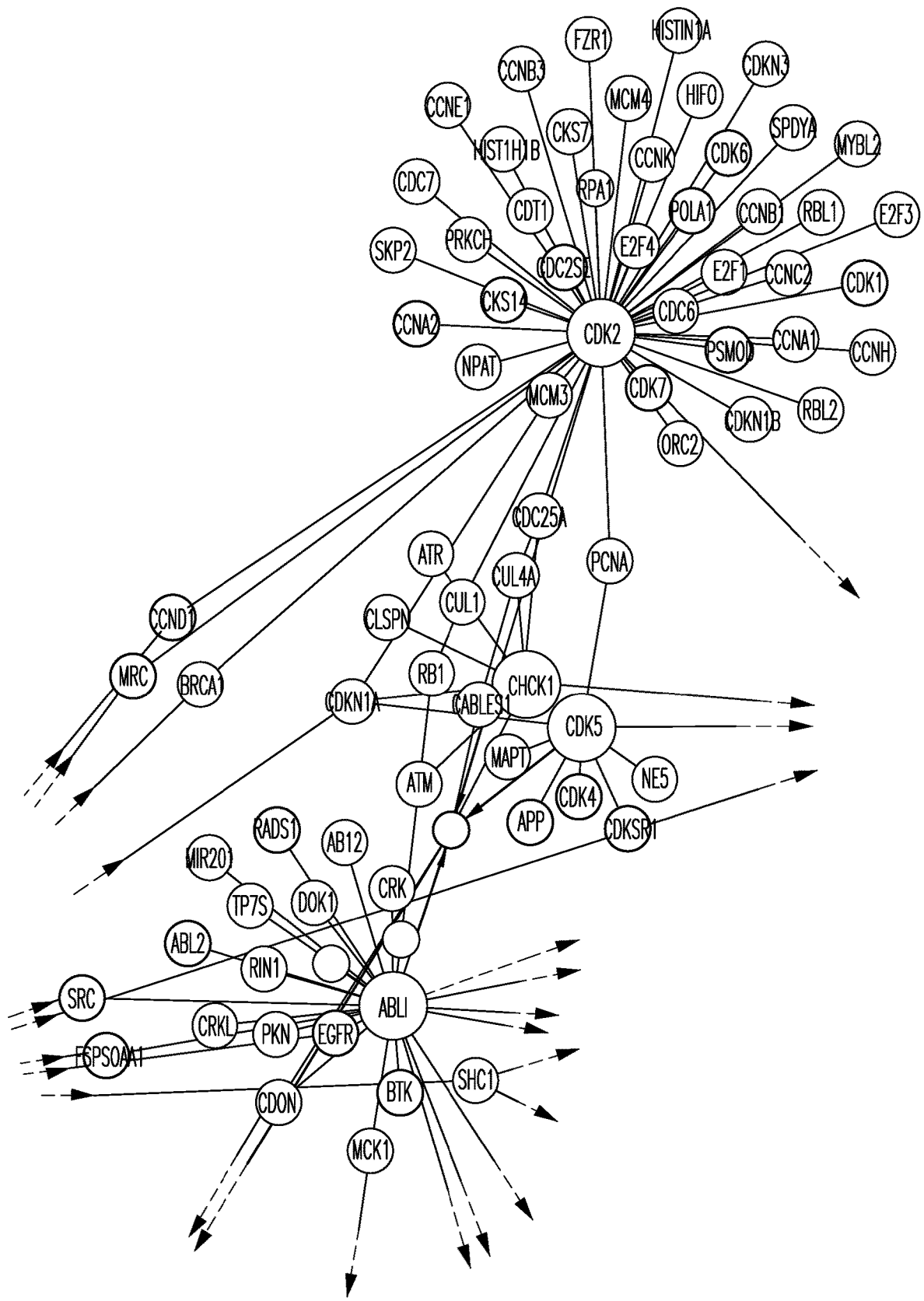
FIG 5A (cont. 2)

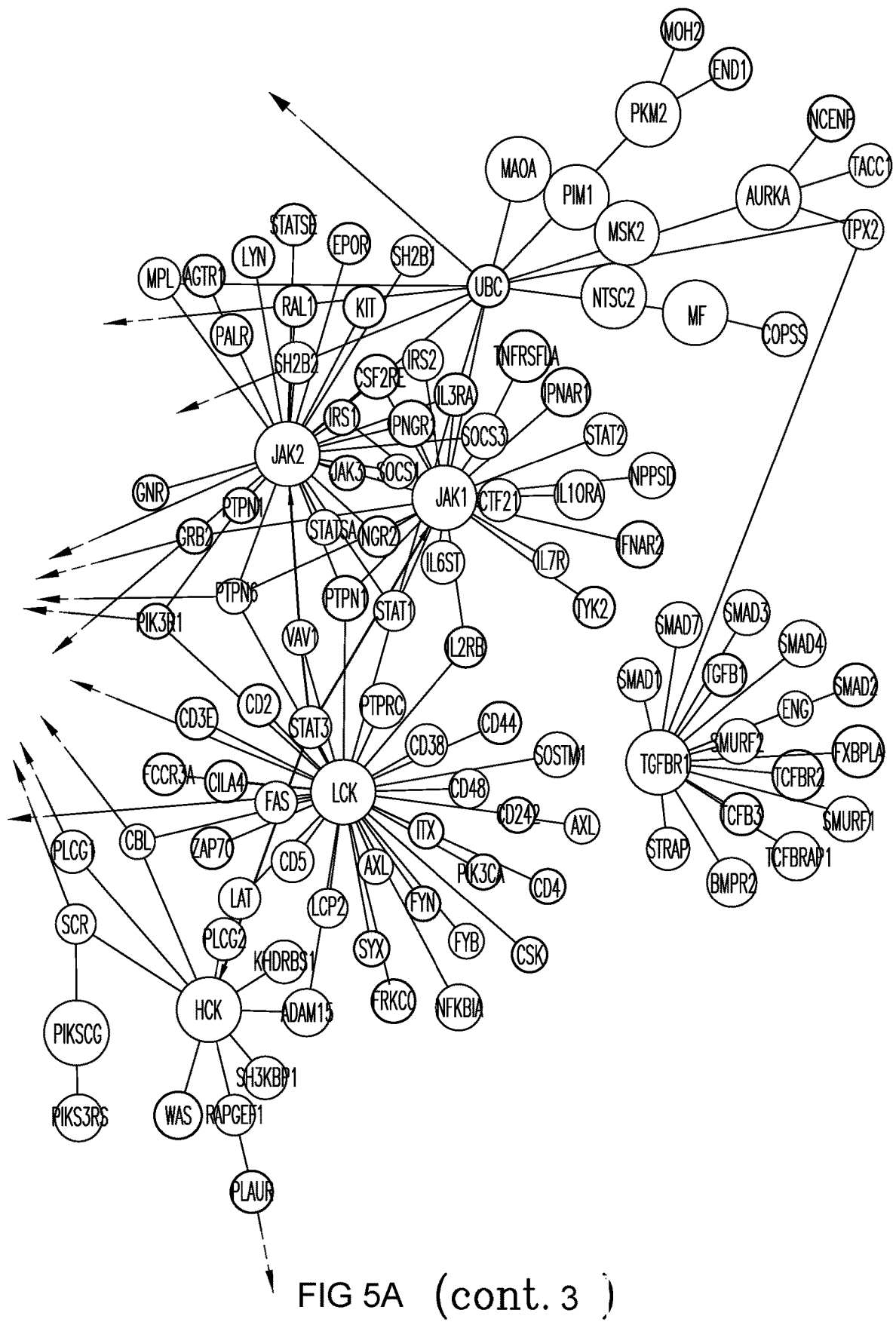
FIG 5A (cont. 3)

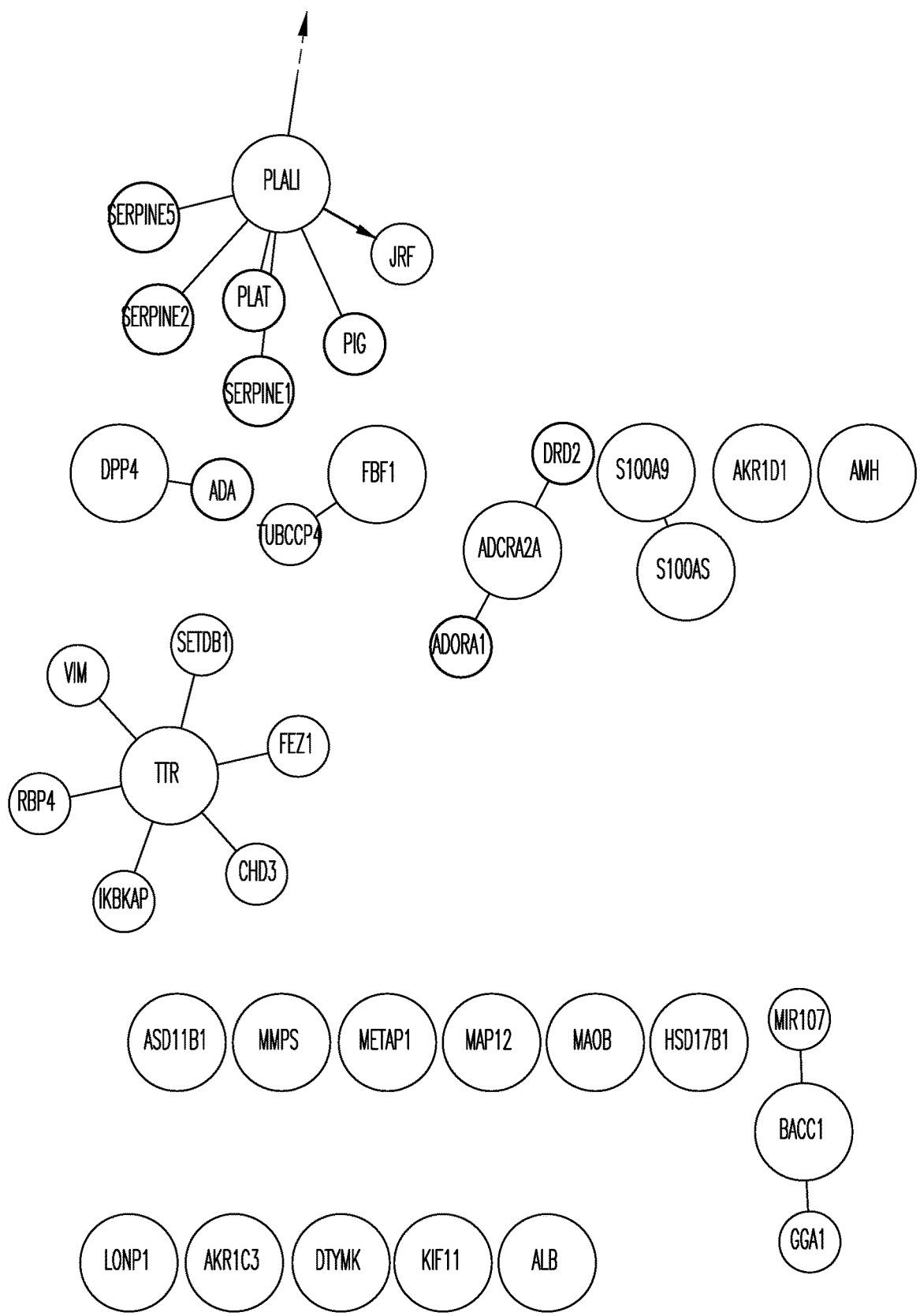
FIG 5A (cont. 4)

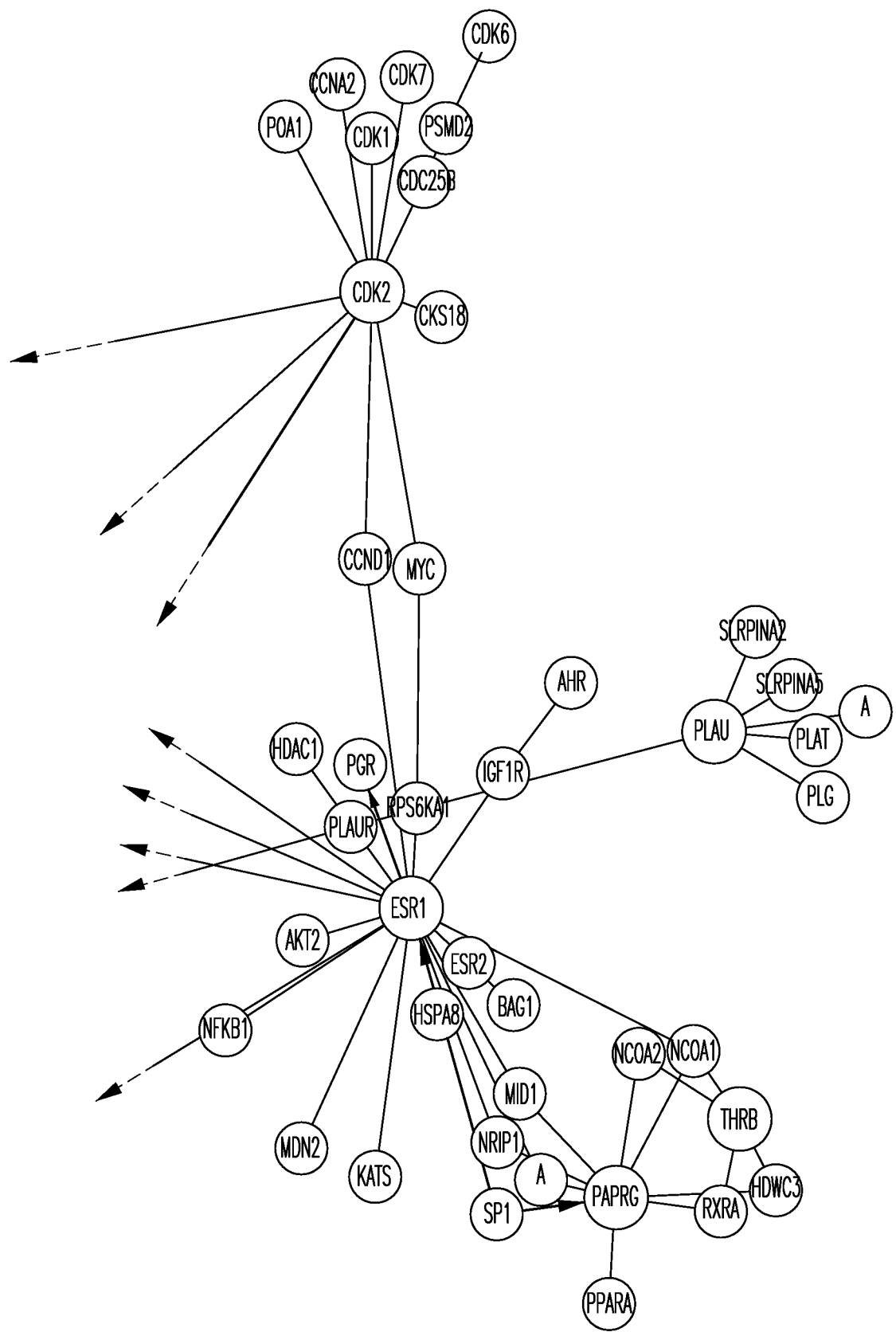
FIG 5B (cont. 1)

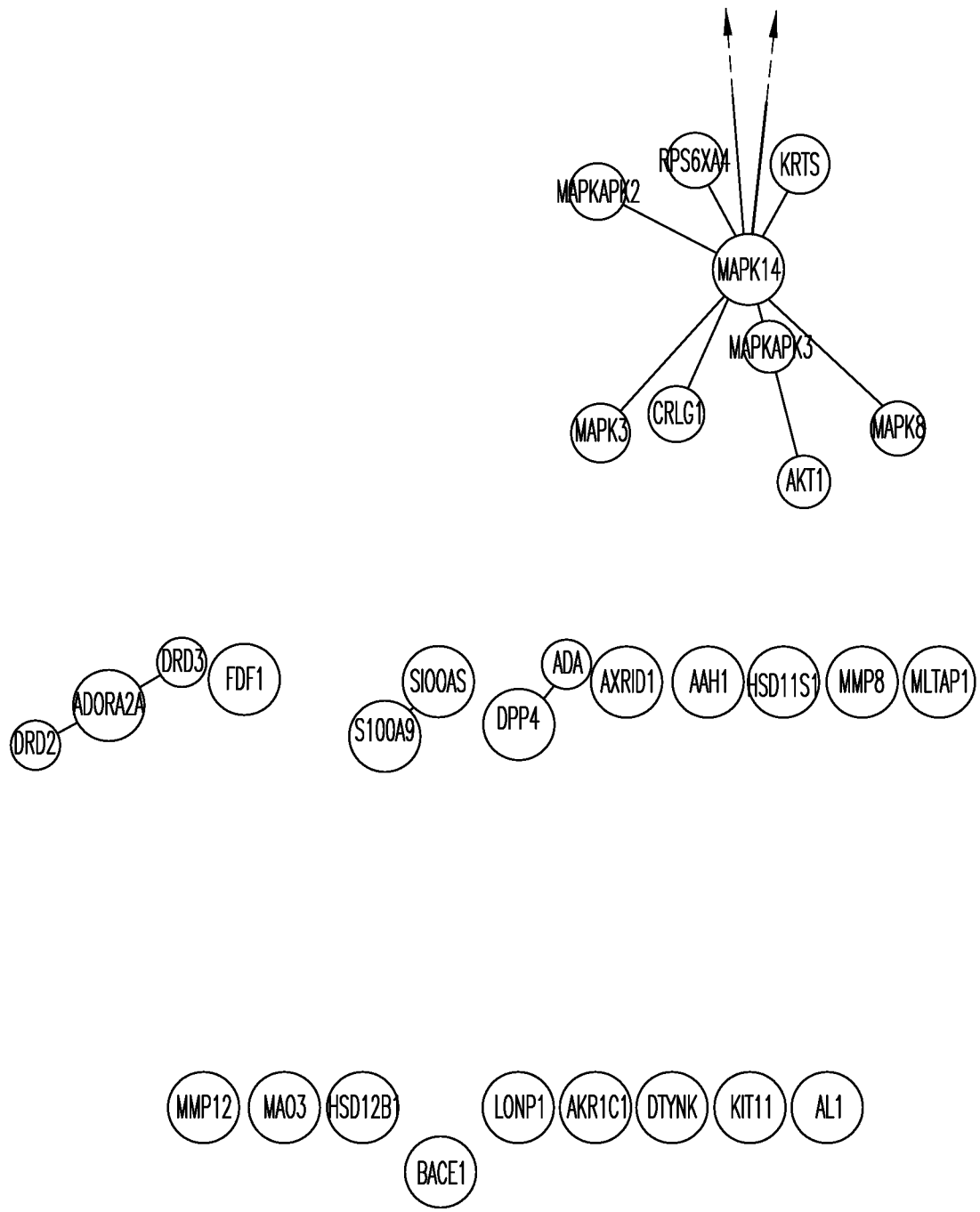
FIG 5B (cont. 2)

Table 3

Fig. 6

| | | General properties | Lipophilicity (LogP) | Solubility (LogS) | Pharmacokinetics (mainly absorption, including P-glycoprotein transporter and metabolism, which is CYPs inhibition) | Druglikeness (including Lipinski) | Medicinal Chemistry |
|---|---|---|---|---|---|---|---|
| QikProp | Informative and understandable plot (About 50 different properties) | | | | | | |
| SwissADME | | General properties | Lipophilicity (LogP) | Solubility (LogS) | Pharmacokinetics (mainly absorption, including P-glycoprotein transporter and metabolism, which is CYPs inhibition) | Druglikeness (including Lipinski) | Medicinal Chemistry |
| admetSAR | Absorption: Details about the: 1. Absorption (in general 2. Caco-2 permability 3. Blood Brain Barrier 4. P-glycoprotein transporter 5. Renal Organic Cation transporter | Distribution: Prediction of the location at the cell | Metabolism: The main value is "CYP Inhibitory Promiscuity" | Excretion: No data | Toxicity: 8 different values on toxicity | | |

Table 4     Fig. 7

| | Candidate | CNS | QPPMDCK (CNS) | QPPCaco | Human Oral Absorption | Percent Human Oral Absorption | QPlogPo/w | QPlogS | QPlogHERG | #amine | #amide | dip^2/V | IP(eV) | EA(eV) | General Problems |
|---|---|---|---|---|---|---|---|---|---|---|---|---|---|---|---|
| 01-02 | 86282818 | 0 | + | + | 1 | + | - | - | - | + | + | + | + | + | 4 |
| 03-06 | 15607447 | -2 | +/- | +/- | 3 | + | + | - | + | + | + | - | - | + | 4 |
| 07 | 42992072 | 1 | +/- | + | 3 | + | + | - | + | + | + | + | + | + | 1 |
| 08-09 | 25760823 | 0 | +/- | +/- | 3 | +/- | + | + | - | + | - | + | + | + | 4 |
| 10-11 | 82320451 | -1 | + | + | 3 | + | + | + | - | + | + | + | - | + | 2 |
| 12 | 42459198 | 0 | + | + | 3 | + | + | - | - | + | + | + | + | + | 1 |
| 13-14 | 37867671 | 2 | + | + | 4 | + | + | - | + | + | + | + | + | + | 1 |
| 15-16 [A] | 27686904 | 0 | + | +/- | 3 | + | + | + | - | + | + | + | + | + | 2 |
| 17-18 | 17057751 | 1 | +/- | + | 3 | + | + | + | + | - | + | - | + | + | 2 |
| 19 | 38058095 | 0 | +/- | +/- | 3 | + | + | - | - | + | + | + | + | + | 2 |
| 20-23 | 36585388 | 1 | +/- | + | 2 | +/- | - | - | + | + | + | + | + | + | 4 |
| 24 [B] | 88095528 | -1 | + | + | 3 | + | + | + | - | + | + | + | + | + | 3 |
| 25 | 57540036 | 0 | + | + | 3 | + | + | - | + | + | + | + | + | + | 1 |
| 26 | 54056378 | -2 | +/- | +/- | 3 | +/- | + | - | - | + | + | + | + | + | 4 |
| 27-28 | 83101459 | 1 | +/- | +/- | 3 | + | + | + | + | + | + | + | + | - | 2 |
| 29 | 76195865 | 0 | +/- | + | 3 | + | + | - | - | + | + | + | + | + | 1 |
| 30 | 34834825 | -1 | +/- | +/- | 3 | + | + | + | - | + | + | + | + | + | 3 |
| 31-32 | 68349003 | -1 | +/- | +/- | 3 | +/- | + | + | - | + | + | + | + | + | 3 |
| 33-36 | 78653061 | 1 | +/- | +/- | 3 | +/- | + | + | + | - | + | + | + | + | 3 |

Table 5

Fig. 8

| Compound | Candidate | Plot | LogP | LogS | GI absorption | BBB permeant | P-gp substrate | CYPs inhibition | Lipinski violations | General problems |
|---|---|---|---|---|---|---|---|---|---|---|
| 01-02 | 86282818 | + | + | - | + | + | s | 4/5 | 0/4 | 3 |
| 03-06 | 15607447 | - | + | - | + | + | s | 4/5 | 0/4 | 4 |
| 07 | 42992072 | + | + | - | + | + | s | 1/5 | 0/4 | 2 |
| 08-09 | 25760823 | + | + | +/- | + | - | s | 1/5 | 0/4 | 1 |
| 10-11 | 82320451 | + | + | +/- | + | + | + | 0/5 | 0/4 | 0 |
| 12 | 42459198 | + | + | - | + | - | s | 0/5 | 0/4 | 2 |
| 13-14 | 37867671 | + | + | +/- | + | + | s | 3/5 | 0/4 | 2 |
| 15-16 [A] | 27686904 | + | + | +/- | + | - | + | 2/5 | 0/4 | 1 |
| 17-18 | 17057751 | + | + | +/- | + | - | s | 2/5 | 0/4 | 2 |
| 19 | 38058095 | + | + | + | + | + | + | 0/5 | 0/4 | 0 |
| 20-23 | 36585388 | + | + | - | + | + | s | 1/5 | 0/4 | 2 |
| 24 [B] | 88095528 | + | + | - | + | - | s | 0/5 | 0/4 | 1 |
| 25 | 57540036 | - | + | +/- | + | + | + | 5/5 | 0/4 | 4 |
| 26 | 54056378 | - | + | - | + | - | s | 3/5 | 0/4 | 2 |
| 27-28 | 83101459 | + | + | + | + | + | + | 1/5 | 0/4 | 2 |
| 29 | 76195865 | + | + | + | + | - | s | 1/5 | 0/4 | 0 |
| 30 | 34834825 | + | + | + | + | - | s | 1/5 | 0/4 | 1 |
| 31-32 | 68349003 | + | + | + | + | - | s | 0/5 | 0/4 | 1 |
| 33-36 | 78653061 | + | + | +/- | + | + | s | 0/5 | 0/4 | 1 |

Fig. 9A

Table 6

| Compound | Candidate | Human Intestinal Absorption | Caco-2 Permeability | Blood-Brain Barrier | P-gp substrate | Renal Organic Cation Transporter Inhibition | Subcellular localization | CYPs Substrate | CYPs inhibition | Toxicity | General Problems |
|---|---|---|---|---|---|---|---|---|---|---|---|
| 01-02 | 86282818 | + | + | + | S | - | Mitochondira | 1/3 | 3/5 | 2/7 | 5 |
| 03-06 | 15607447 | + | - | + | S | NI | Nucleus | 0/3 | 5/5 | 2/7 | 6 |
| 07 | 42992072 | + | - | + | S | NI | Mitochondira | 1/3 | 2/5 | 2/7 | 5 |
| 08-09 | 25760823 | + | - | + | S | NI | Mitochondira | 1/3 | 0/5 | 2/7 | 4 |
| 10-11 | 82320451 | + | - | - | S | NI | Nucleus | 1/3 | 3/5 | 2/7 | 5 |
| 12 | 42459198 | + | + | + | S | NI | Mitochondira | 1/3 | 0/5 | 2/7 | 4 |
| 13-14 | 37867671 | + | + | + | S | - | Mitochondira | 1/3 | 3/5 | 2/7 | 5 |
| 15-16 [A] | 27686904 | + | - | + | S | NI | Mitochondira | 1/3 | 0/5 | 2/7 | 3 |
| 17-18 | 17057751 | + | - | + | S | - | Mitochondira | 1/3 | 1/5 | 2/7 | 5 |
| 19 | 38058095 | + | + | + | + | NI | Mitochondira | 1/3 | 0/5 | 2/7 | 2 |
| 20-23 | 36585388 | + | - | + | S | - | Mitochondira | 1/3 | 1/5 | 3/7 | 6 |
| 24 [B] | 88095528 | + | - | + | S | NI | Mitochondira | 1/3 | 0/5 | 3/7 | 5 |
| 25 | 57540036 | + | + | + | S | - | Mitochondira | 1/3 | 1/5 | 2/7 | 4 |
| 26 | 54056378 | + | - | + | S | NI | Mitochondira | 1/3 | 1/5 | 2/7 | 4 |
| 27-28 | 83101459 | + | - | + | S | NI | Lysosome | 1/3 | 0/5 | 1/7 | 3 |
| 29 | 76195865 | + | + | + | + | NI | Mitochondira | 1/3 | 4/5 | 2/7 | 3 |
| 30 | 34834825 | + | - | + | S | NI | Mitochondira | 1/3 | 0/5 | 2/7 | 4 |
| 31-32 | 68349003 | + | - | - | S | NI | Mitochondira | 1/3 | 0/5 | 2/7 | 4 |
| 33-36 | 78653061 | + | - | + | S | - | Nucleus | 0/3 | 0/5 | 2/7 | 6 |

Fig. 9B

Table 7

| Candidate | | # of problems per program | | | Decission | Prefferd in the previous report |
|---|---|---|---|---|---|---|
| | | QikProp | SwissADME | AdmetSAR | | |
| 01-02 | 86282818 | 4 | 3 | 5 | | |
| 03-06 | 15607447 | 4 | 4 | 6 | | Yes |
| 07 | 42992072 | 1 | 2 | 5 | | Yes |
| 08-09 | 25760823 | 4 | 1 | 4 | | |
| 10-11 | 82320451 | 2 | 0 | 5 | | |
| 12 | 42459198 | 1 | 2 | 4 | | |
| 13-14 | 37867671 | 1 | 2 | 5 | | Yes |
| 15-16 [A] | 27686904 | 2 | 1 | 3 | Prefered | |
| 17-18 | 17057751 | 2 | 2 | 5 | | |
| 19 | 38058095 | 2 | 0 | 2 | Prefered | |
| 20-23 | 36585388 | 4 | 2 | 6 | | |
| 24 [B] | 88095528 | 3 | 1 | 5 | | |
| 25 | 57540036 | 1 | 4 | 4 | | |
| 26 | 54056378 | 4 | 2 | 4 | | Yes |
| 27-28 | 83101459 | 2 | 2 | 3 | Prefered | |
| 29 | 76195865 | 1 | 0 | 3 | Prefered | Yes |
| 30 | 34834825 | 3 | 1 | 4 | | |
| 31-32 | 68349003 | 3 | 1 | 4 | | |
| 33-36 | 78653061 | 3 | 1 | 6 | | |

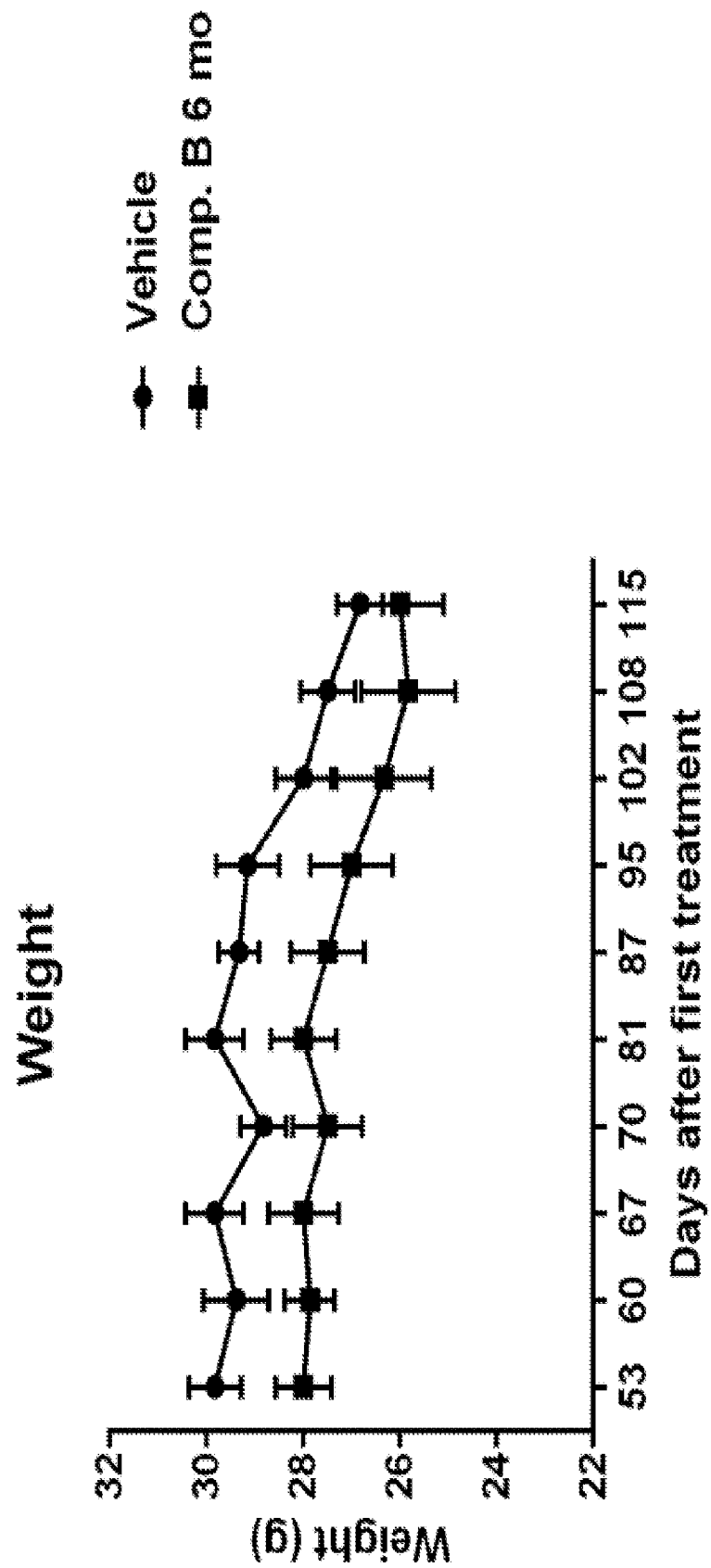

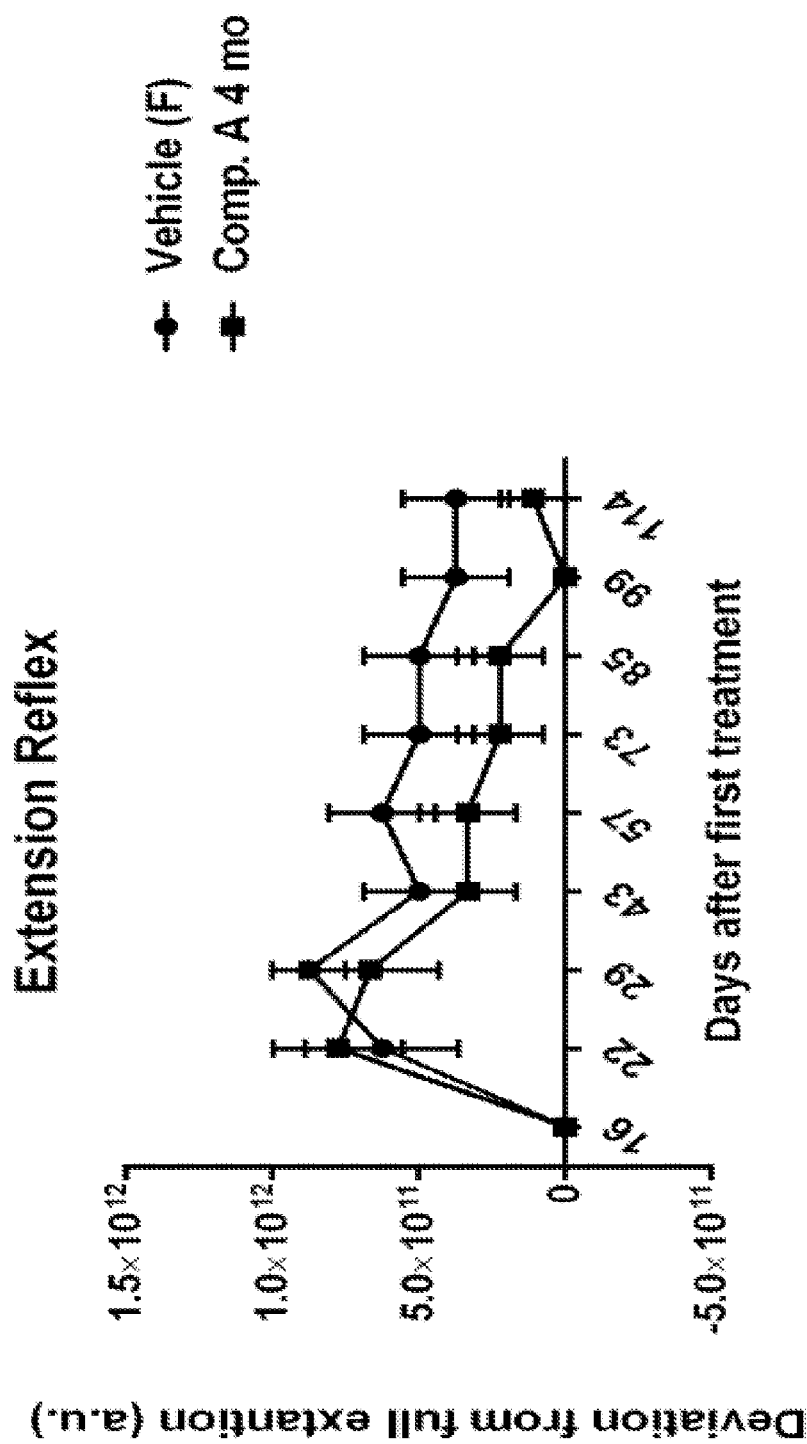

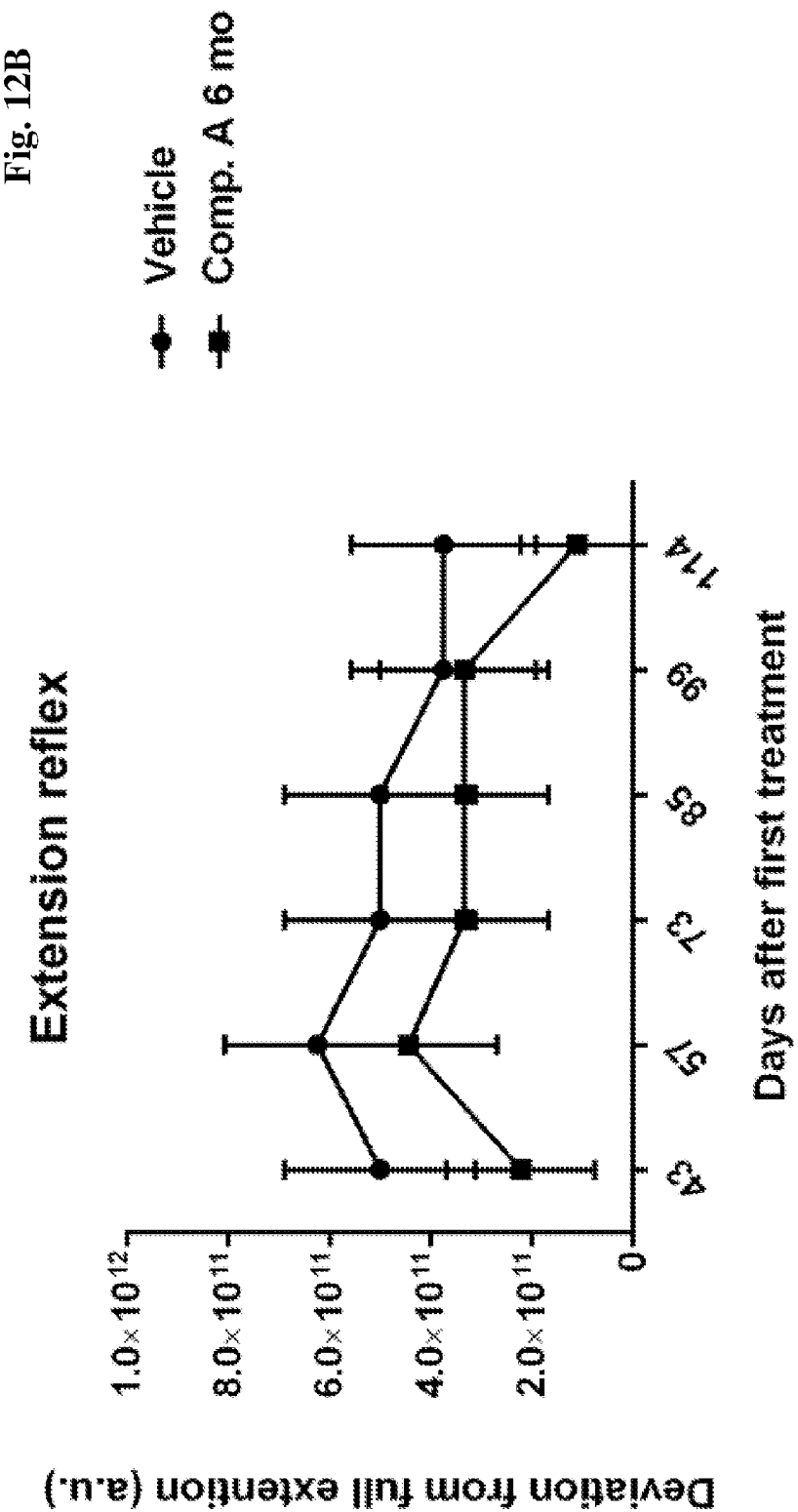

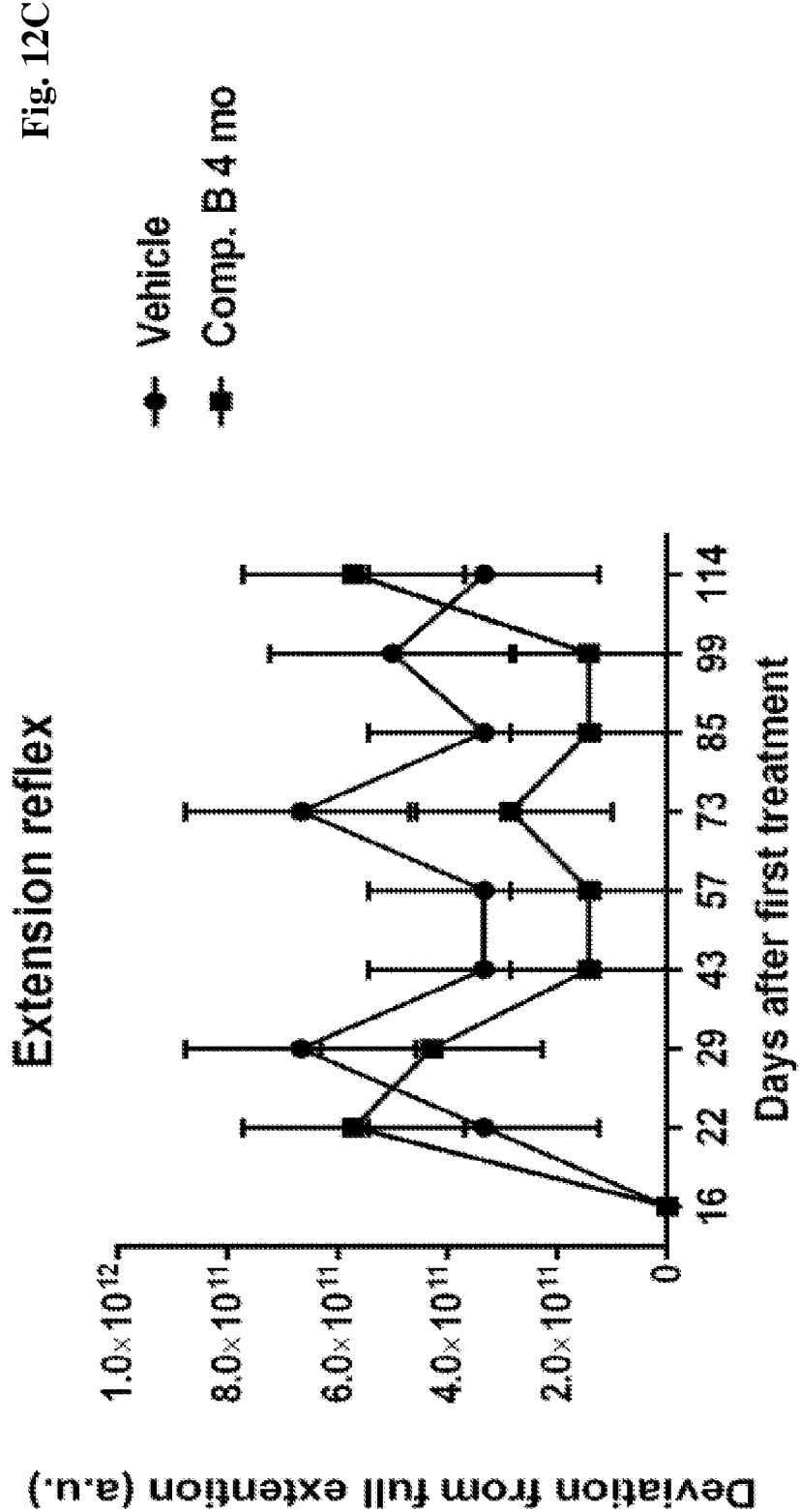

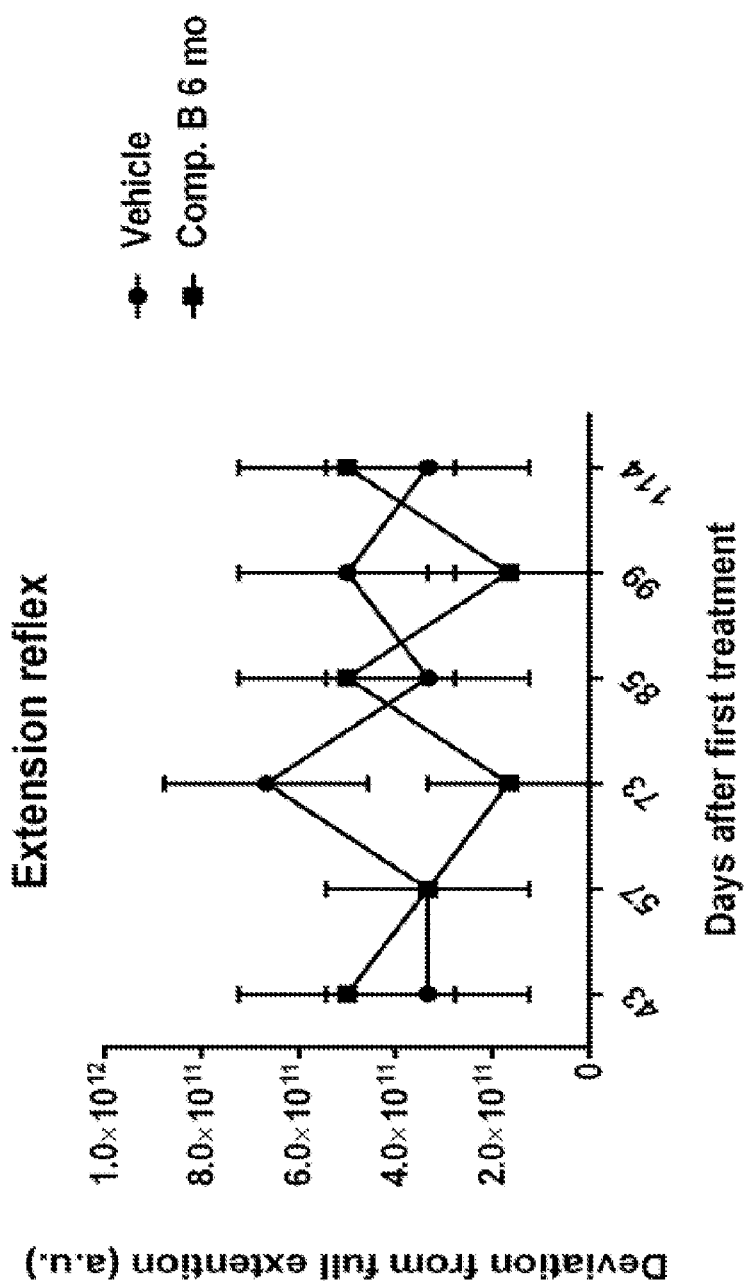

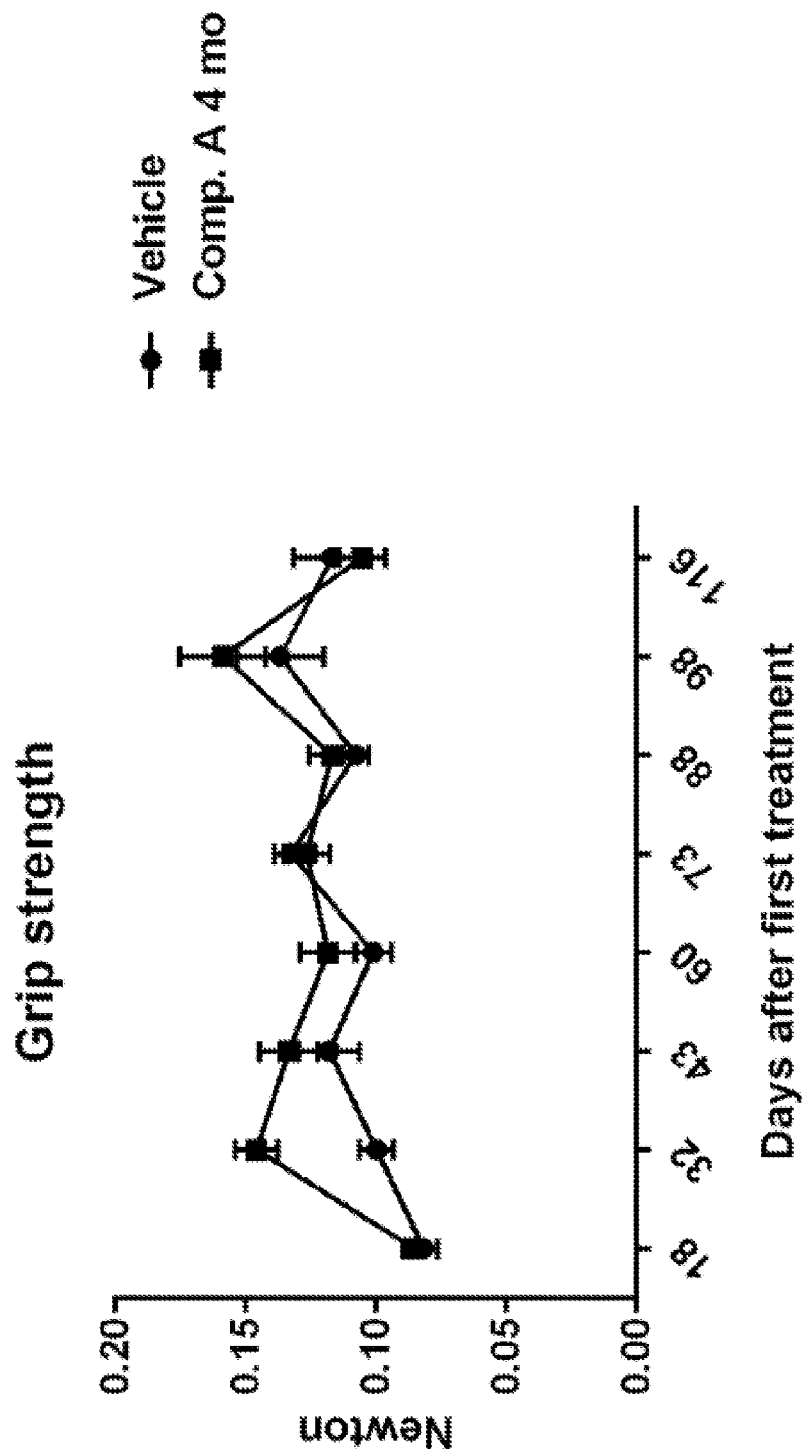

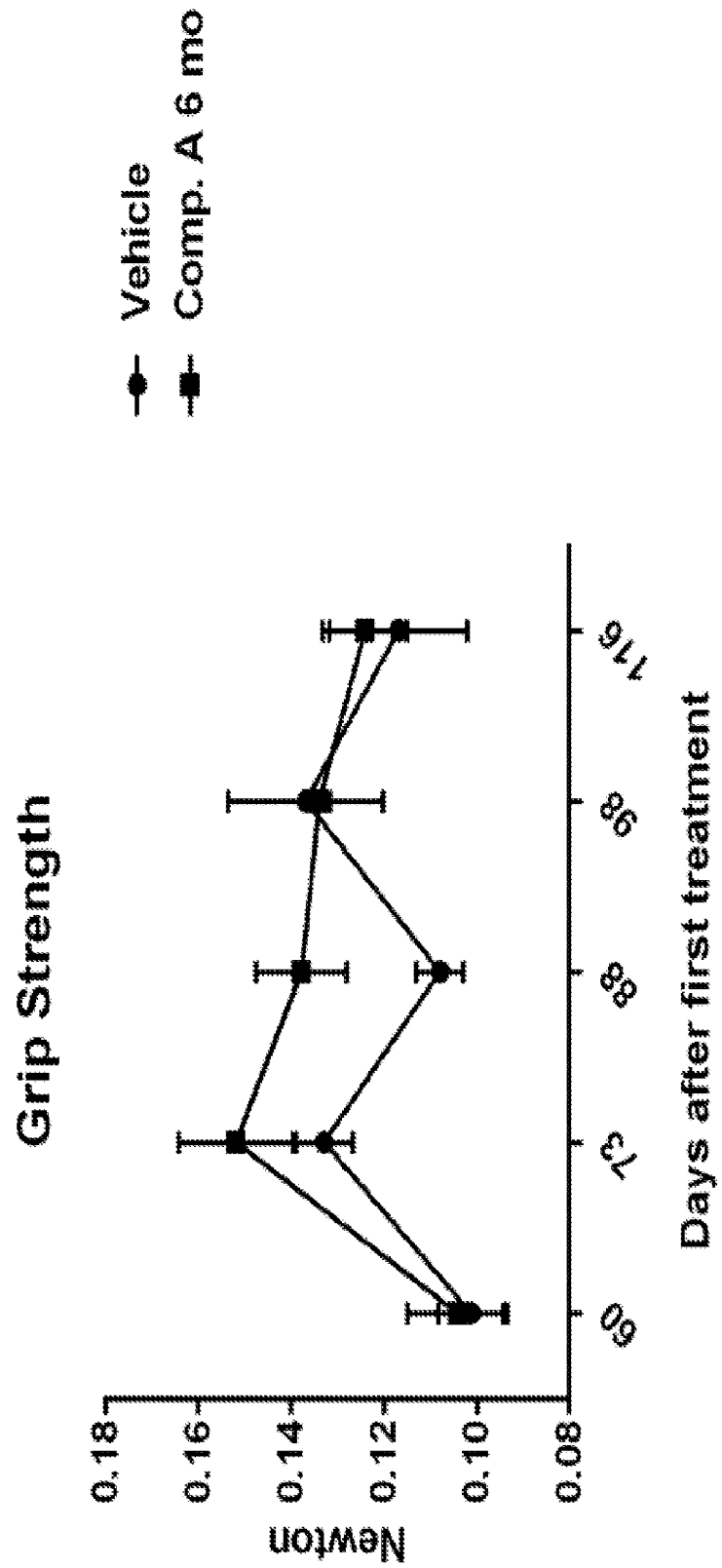

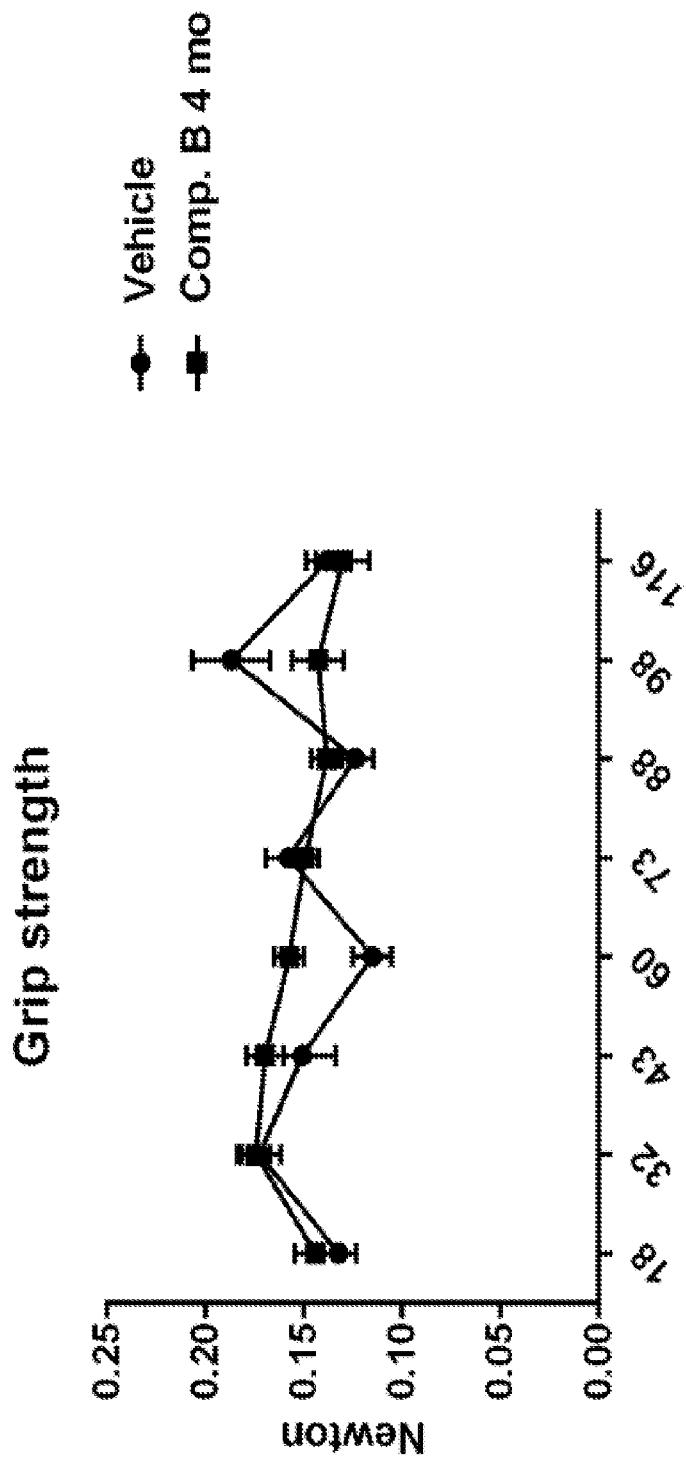

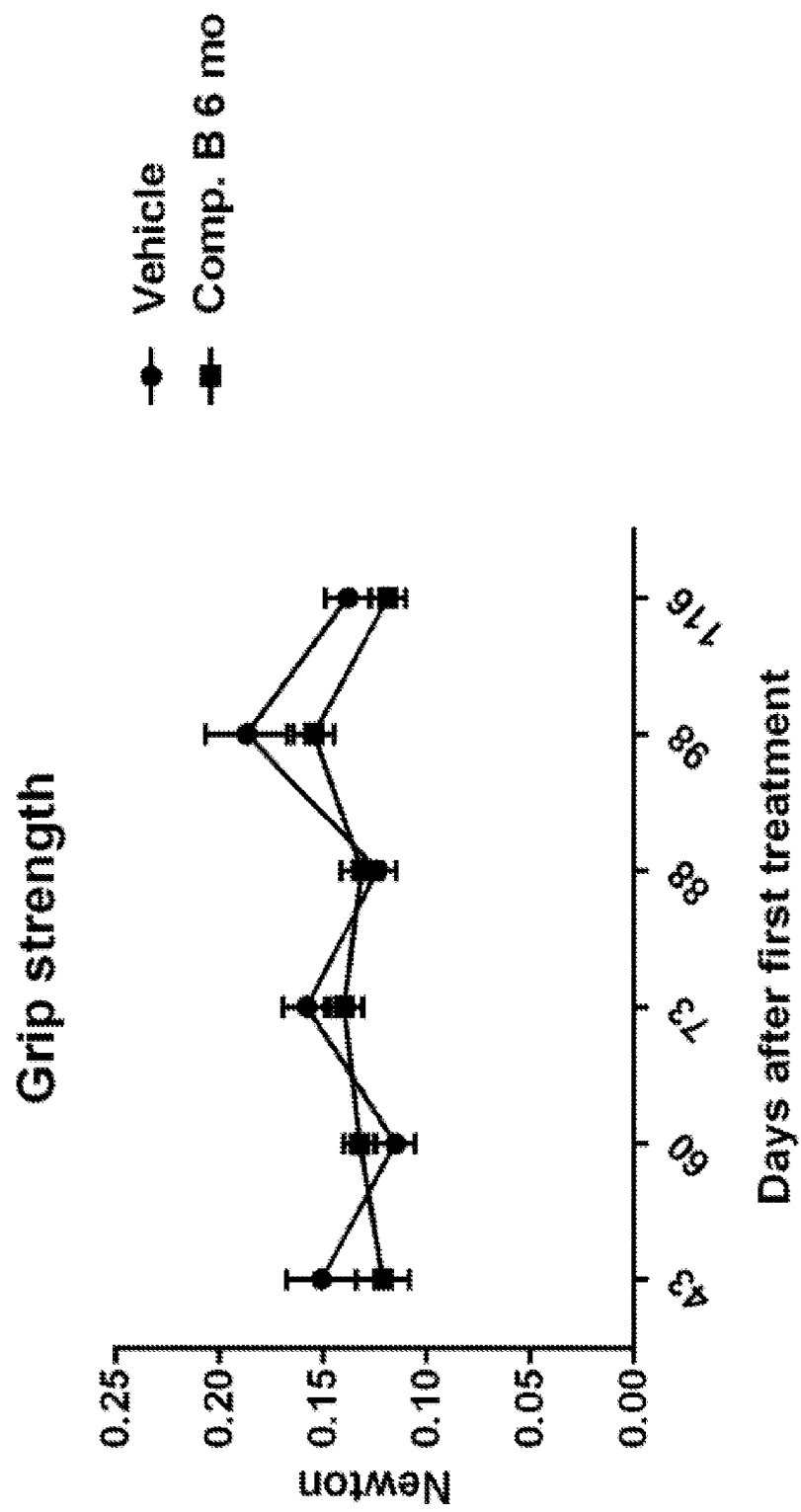

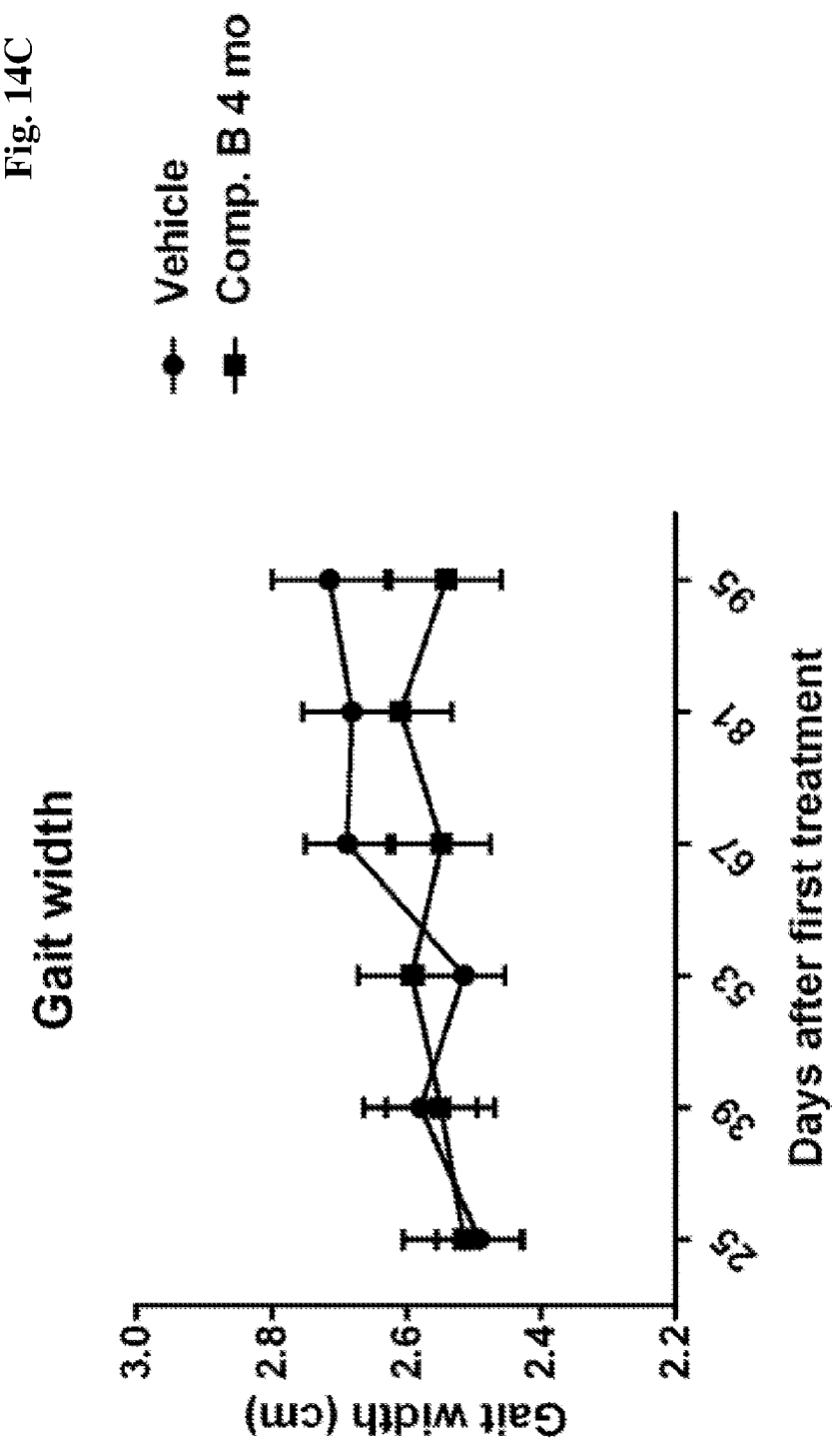

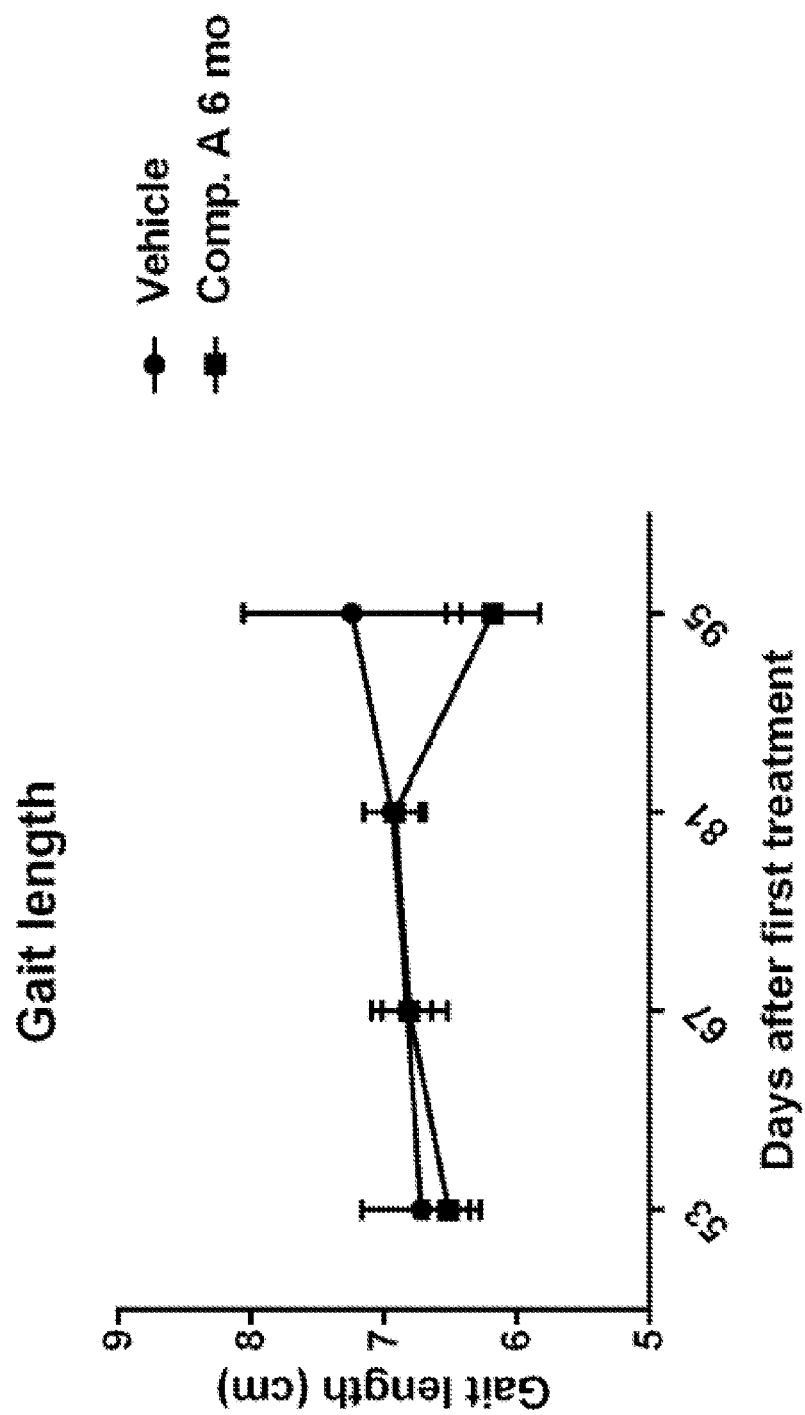

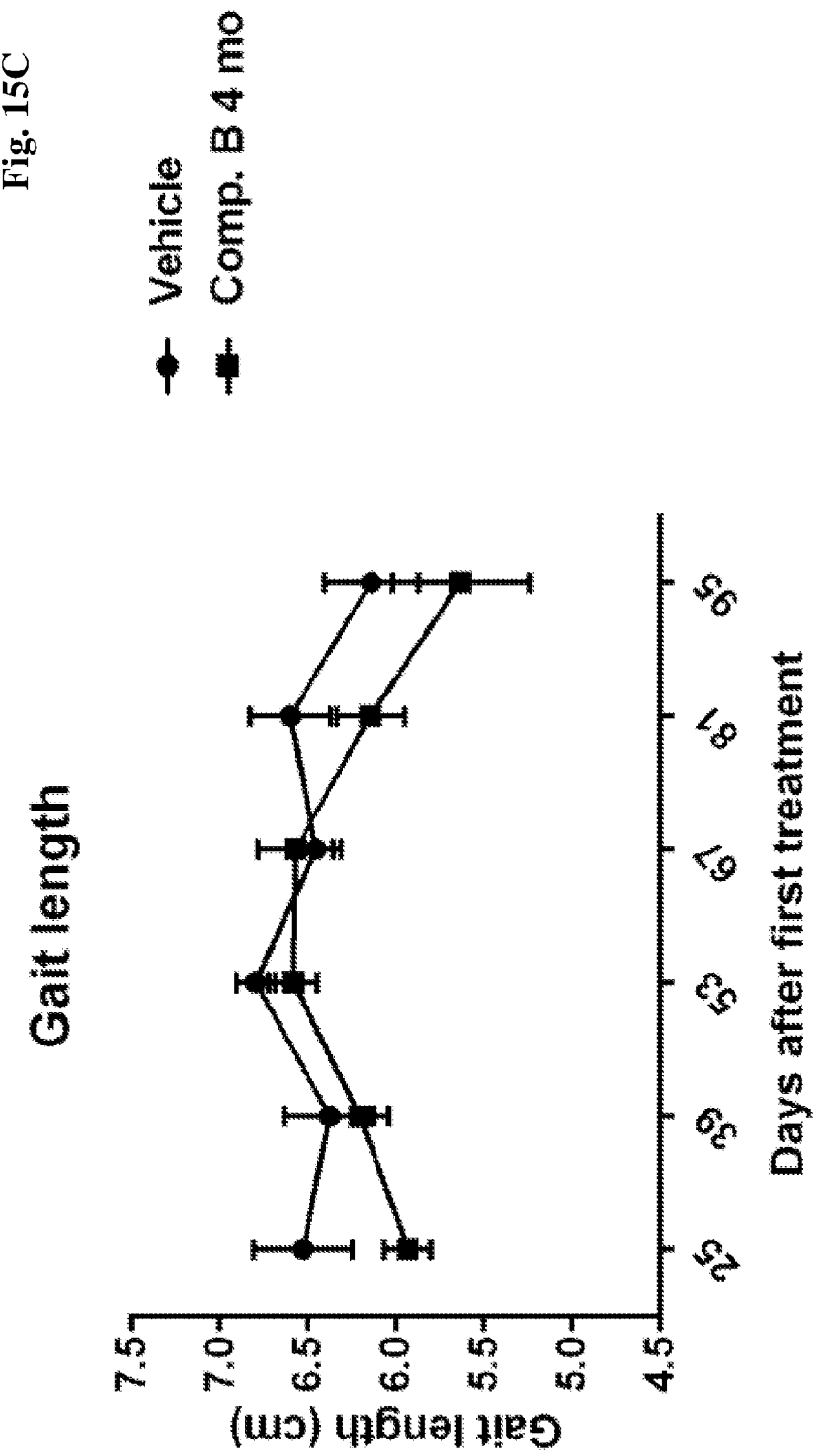

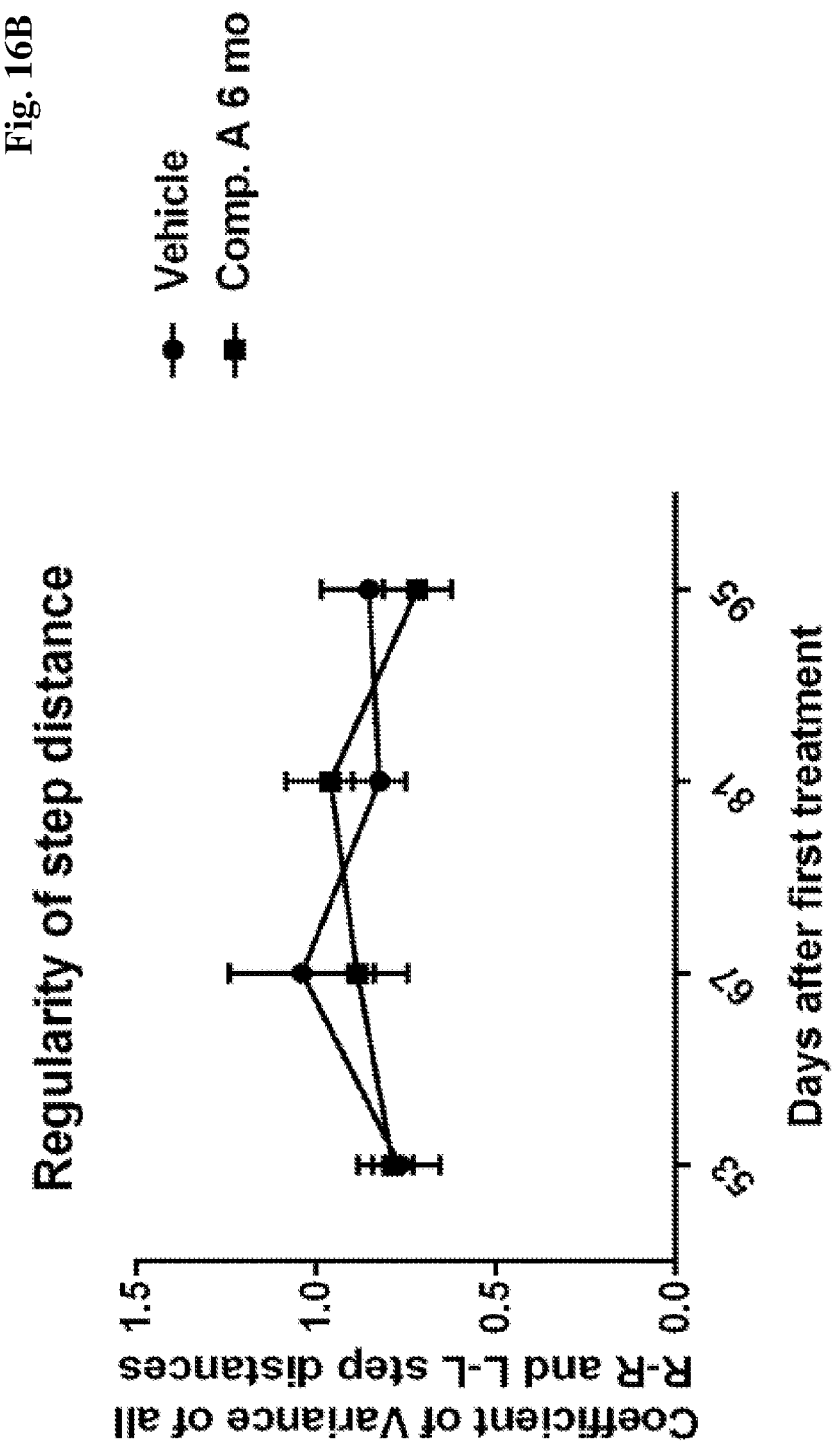

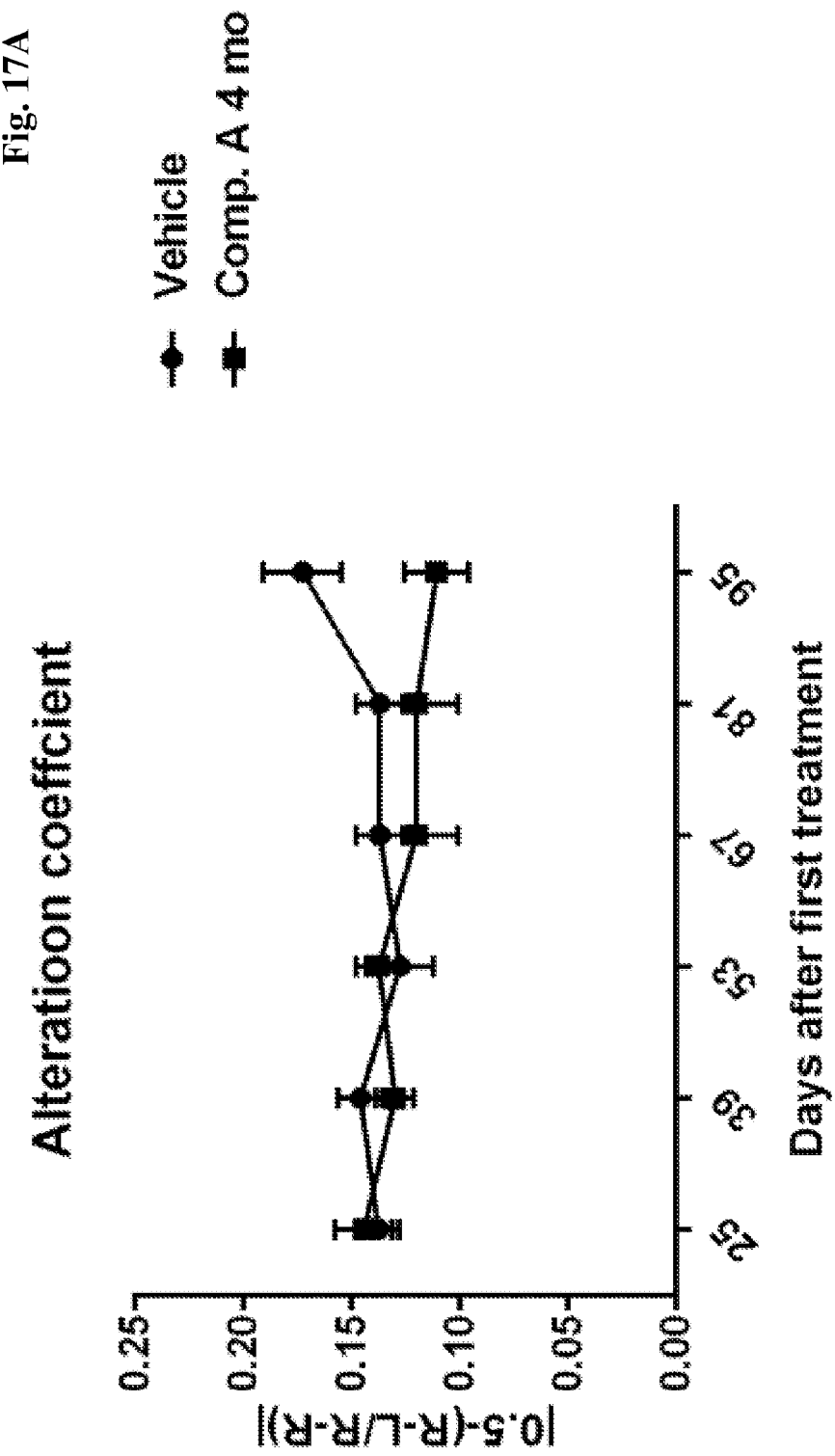

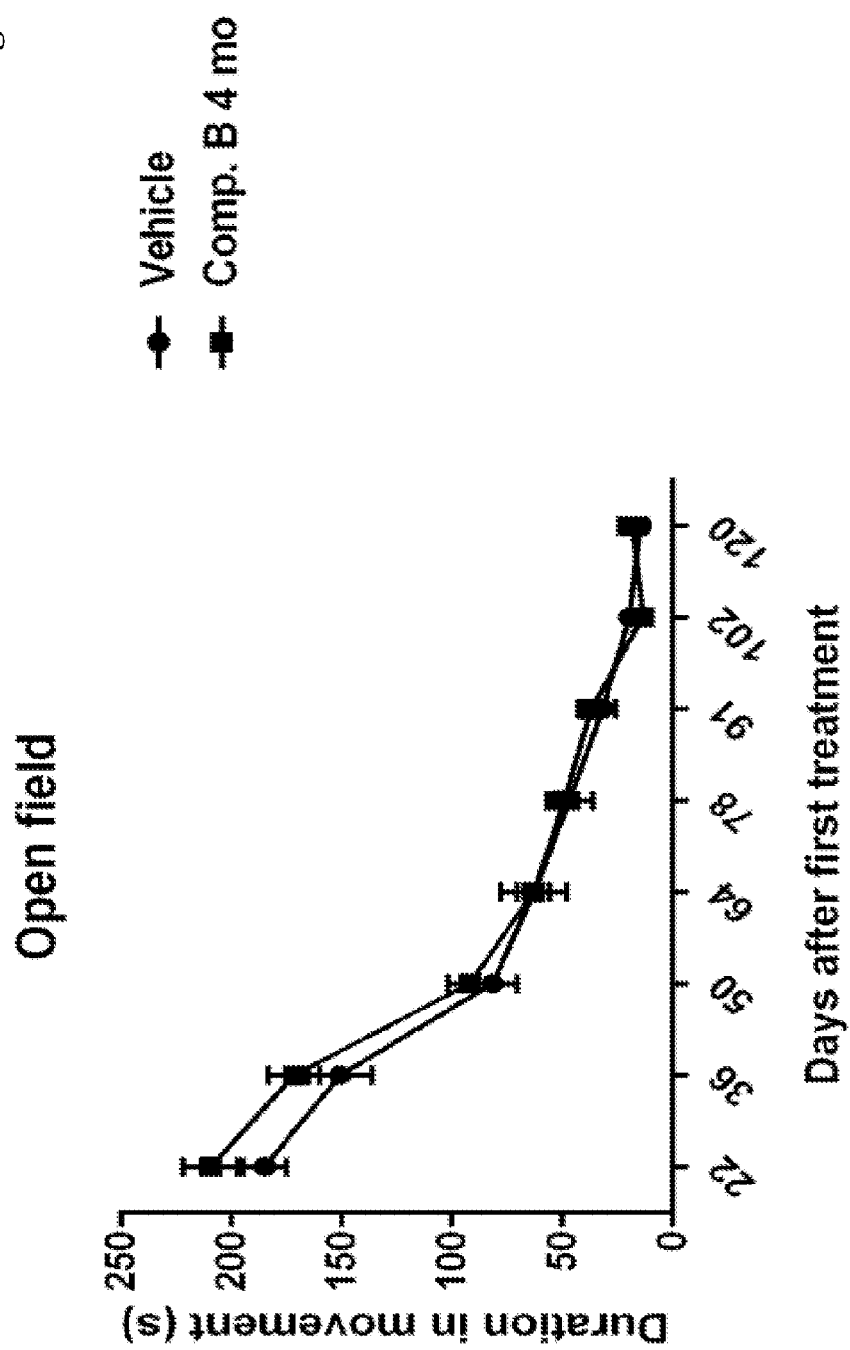

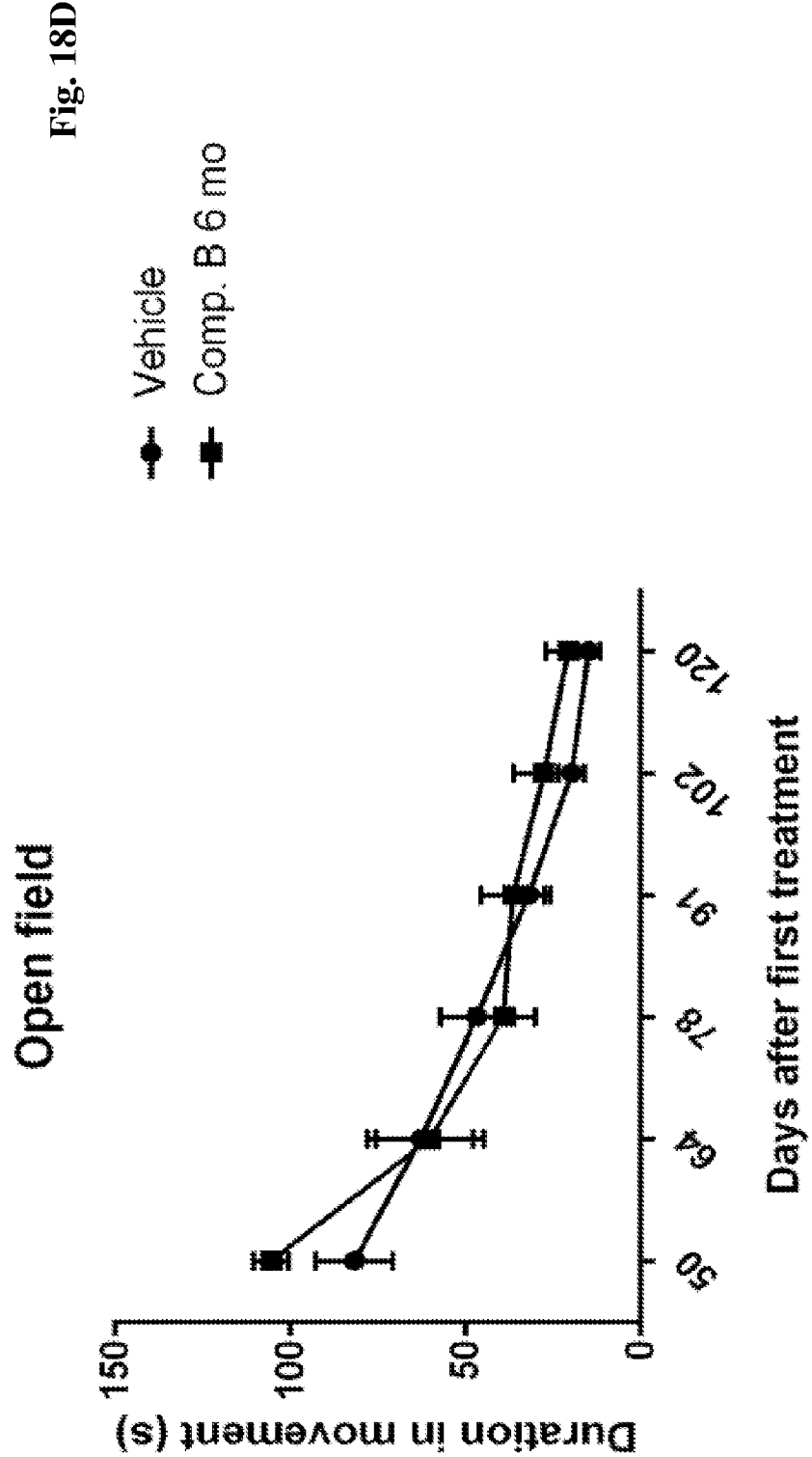

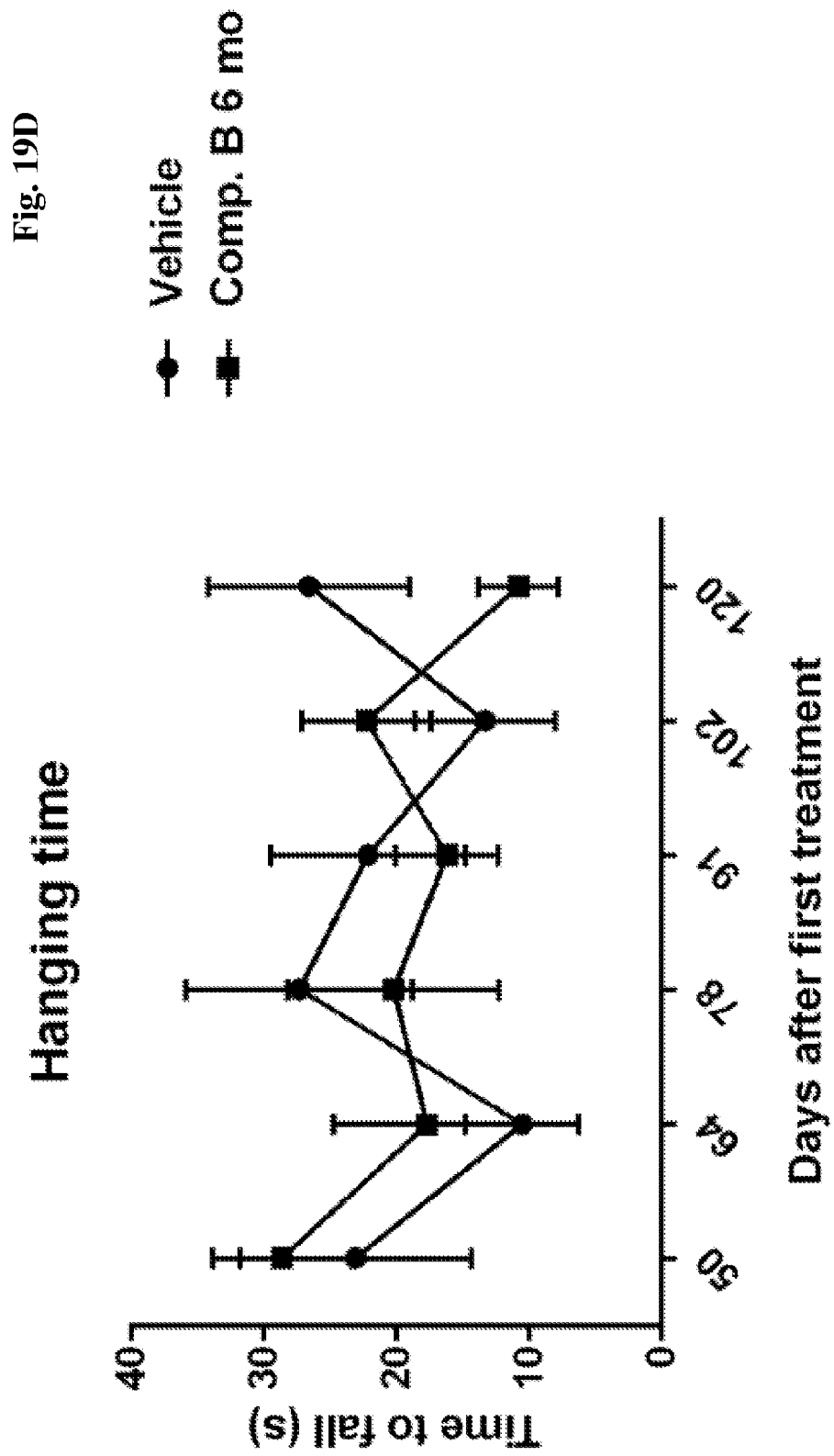

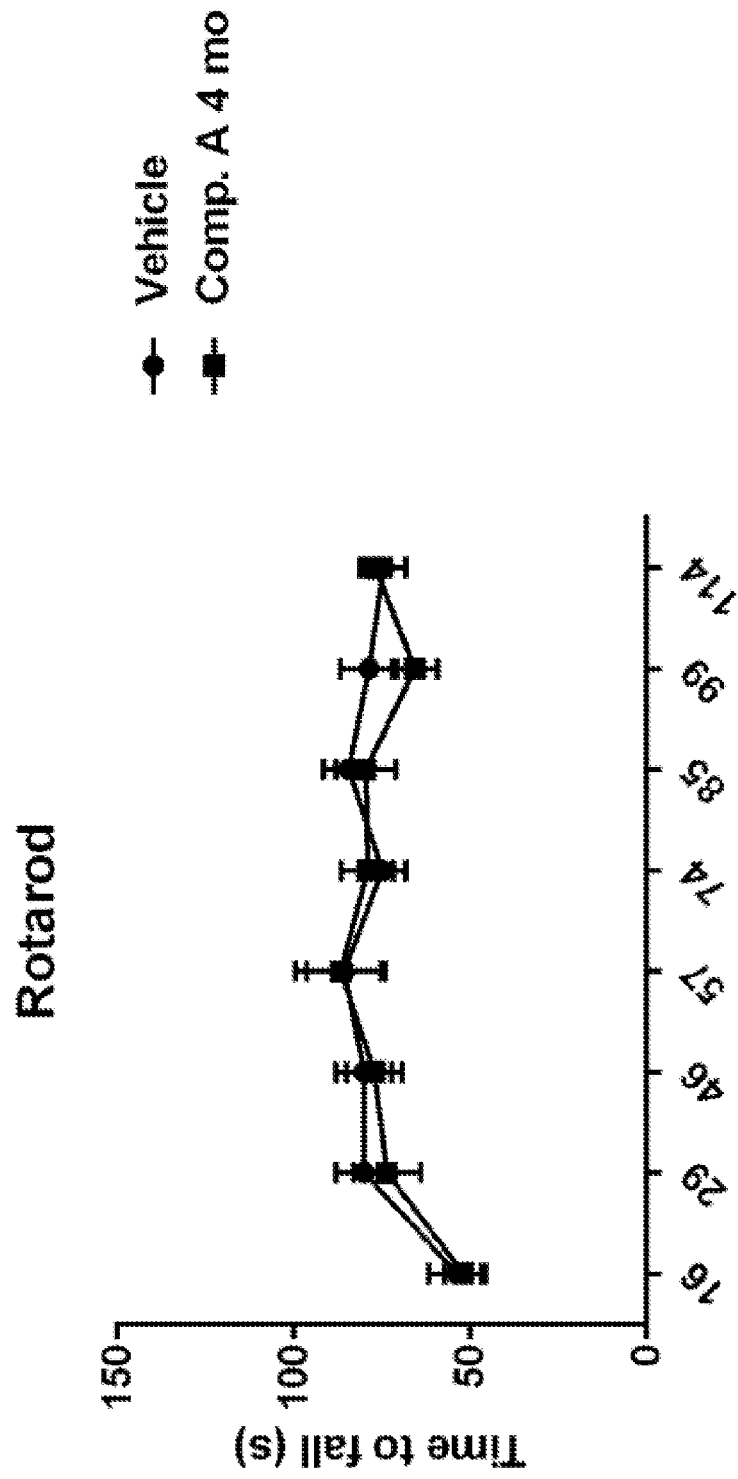

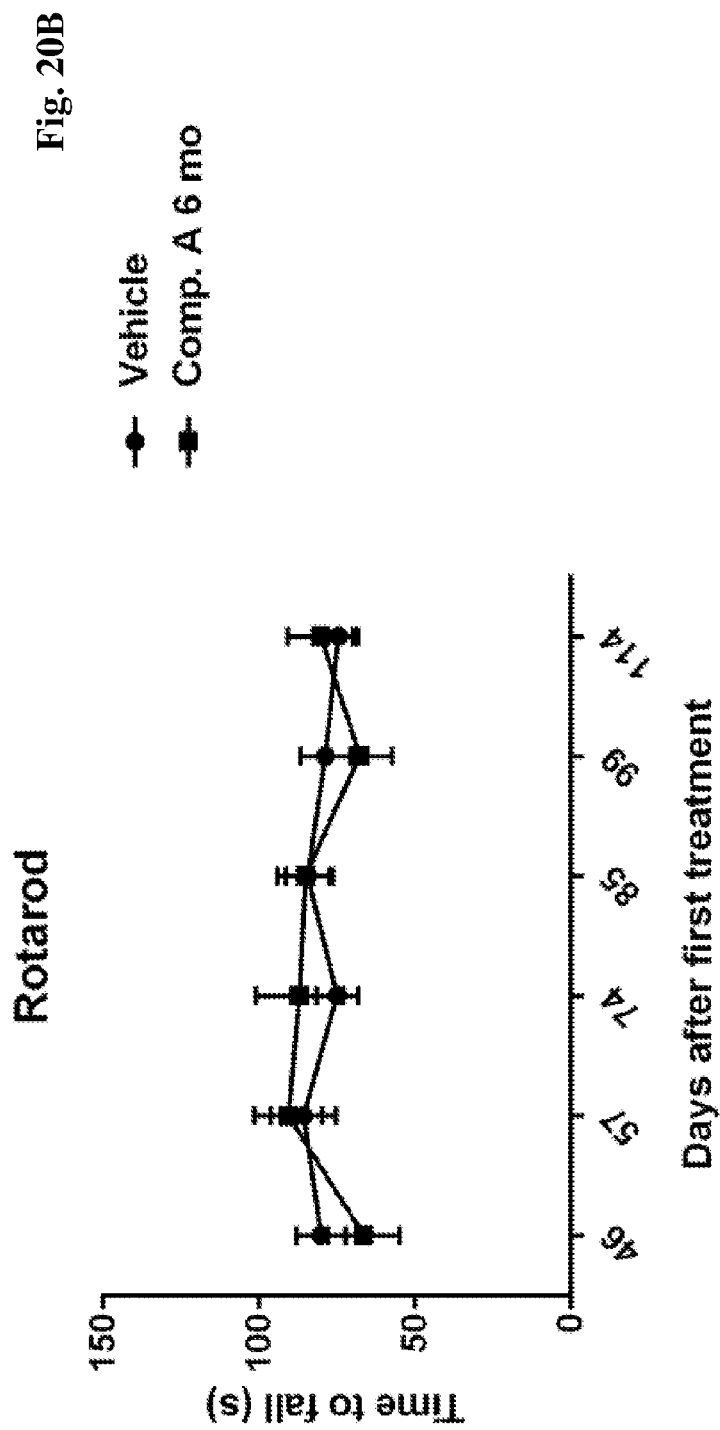

COMPOUNDS FOR THE TREATMENT OF GLYCOGEN STORAGE DISORDERS

CROSS-REFERENCE TO RELATED APPLICATIONS

This application is a divisional application of U.S. Ser. No. 16/485,577 filed Aug. 13, 2019, which is a National Phase of PCT Patent Application No. PCT/IL2018/050207 having International filing date of Feb. 22, 2018, which claims the benefit of priority of U.S. Provisional Application No. 62/461,884 filed on Feb. 22, 2017. The contents of the above document is applications are all incorporated by reference as if fully set forth herein in their entirety.

FIELD OF THE INVENTION

The present invention, in some embodiments thereof, relates to compounds for the treatment of glycogen storage disorders.

BACKGROUND OF THE INVENTION

Glycogen is a compact polymer of alpha-1,4-linked glucose units regularly branched with alpha-1,6-glucosidic bonds, serving as the main carbohydrate store and energy reserve across many phyla.

The two major sites of glycogen storage are liver and muscle. The primary function of glycogen varies in different tissues. In liver, glycogen serves as a glucose reserve for the maintenance of blood-glucose levels. In muscle, glycogen provides energy for muscle contraction. Glycogen metabolism is a complex process involving many different enzymes that directly or indirectly regulate glycogen synthesis and degradation. In mammalian cells, glycogen is synthesized in the cytosol by the two enzymes, glycogen synthase (GS) and glycogen branching enzyme (GBE). Most glycogen is degraded in the cytoplasm (glycogenolysis) by a combined action of glycogen phosphorylase (GP) (cleaves the 1,4-glycosidic bonds) and glycogen debranching enzyme (GDE) (cleaves 1,6-glycosidic bonds at the branch points). A small amount of glycogen is transported into lysosomes and digested into glucose by the enzyme acid alpha-glucosidase (GAA).

Mutations in genes encoding these enzymes cause a partial or complete loss of the enzyme activities in glycogen storage disorders or diseases (GSDs), a group of genetic disorders with abnormal metabolism of glycogen primarily in liver, muscle, and the brain. There are over 13 forms of GSD presently identified, and a wide spectrum of clinical presentations is seen. GSD types I, II, III, VI, VII, and IX are currently recognized as the most common forms, accounting for over 90 percent of all cases. Some deficiencies can affect several tissues (liver, muscle, and other tissues) caused by excessive accumulation of glycogen. Some GSDs (Adult Polyglucosan Body Disease (APBD), Tarui and Lafora diseases) are caused by intracellular accumulation of insoluble inclusions, called polyglucosan bodies (PB), which are chiefly composed of malconstructed glycogen.

SUMMARY OF THE INVENTION

The present invention, in some embodiments thereof, relates to compounds for the treatment of glycogen storage disorders.

According to an aspect of some embodiments of the present invention, there is provided a compound represented by Formula I:

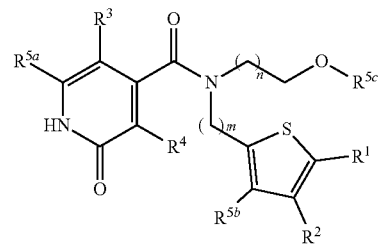

or a pharmaceutically acceptable salt thereof, wherein:
n and m are each integers representing, independently, 1, 2, or 3;
$R^1$ to $R^4$ represent substituents, independently in each occurrence comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted, and
$R^{5a-c}$ represent $C_{1-6}$ alkyl.
In some embodiments, n and m are 1.
In some embodiments, $R^{5a-c}$ represent methyl.
In some embodiments, the compound is in the form of Formula Ia:

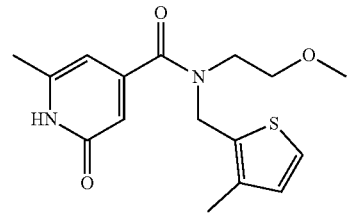

In some embodiments, the compound is represented by Formula II:

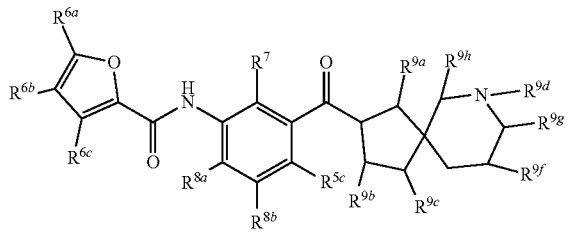

wherein $R^{6a}$ to $R^{6c}$, $R^7$, $R^{8a}$ to $R^{8c}$, independently and in each occurrence represent at least one substituent comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted, and
$R^{9a}$ to $R^{9h}$ independently and in each occurrence represent one or more substituents comprising or being selected from the group consisting of hydrogen or $C_{1-6}$ alkyl.

In some embodiments, $R^{9d}$ is hydrogen.

In some embodiments, $R^7$ is methyl.

In some embodiments, the compound is in the form of Formula IIa:

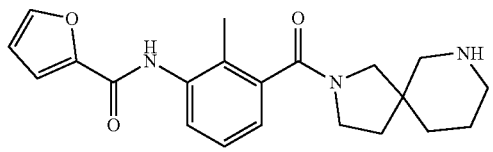 [SMILES: Cc1c(NC(=O)c2ccco2)cccc1C(=O)N1CCC2(CCCNC2)C1]

In some embodiments, the compound is represented by Formula III:

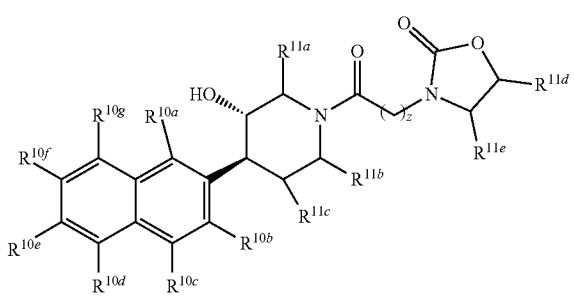

wherein $R^{10a}$ to $R^{10g}$ represent substituents, independently in each occurrence comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted;

z is an integer representing, independently, 1, 2, or 3, and $R^{11a}$ to $R^{11e}$ represent independently and in each occurrence at least one substituent selected from the group consisting of: hydrogen or $C_{1-6}$ alkyl.

In some embodiments, z is 1.

In some embodiments, $R^{10a}$ to $R^{10g}$ and $R^{11a}$ to $R^{11e}$ represent hydrogen.

In some embodiments, the compound is in the form of Formula IIIa:

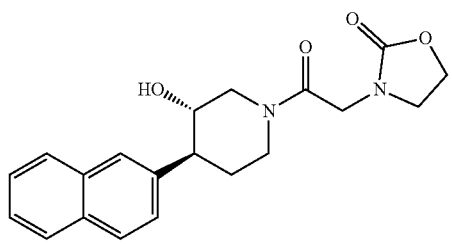 [SMILES: O=C(CN1CCOC1=O)N1CC[C@@H](c2ccc3ccccc3c2)[C@H](O)C1]

In some embodiments, the compound is represented by Formula IV:

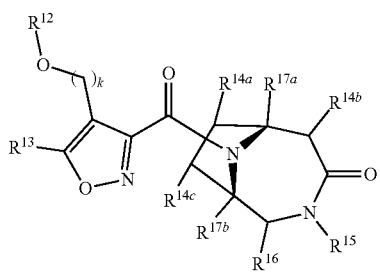

wherein $R^{12}$, $R^{13}$, $R^{14a}$-$R^{14c}$, $R^{15}$, $R^{16}$, and $R^{17a}$-$R^{17b}$ represent substituents, independently in each occurrence comprising or being selected from the group consisting of hydrogen and $C_{1-6}$ alkyl, and k is an integer representing, independently, 1, 2, or 3.

In some embodiments, k is 1.

In some embodiments, $R^{12}$, $R^{13}$ are methyl.

In some embodiments, $R^{15}$ is methyl.

In some embodiments, $R^{14a}$-$R^{14c}$, and $R^{16}$ are hydrogen.

In some embodiments, the compound is in the form of Formula IVa:

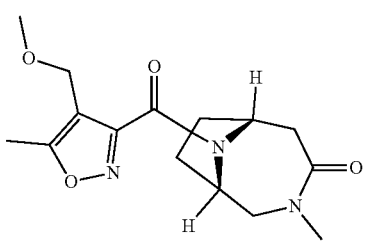

According to an aspect of some embodiments of the present invention, there is provided a pharmaceutical composition comprising one or more of the herein disclosed compounds in any embodiment thereof.

In some embodiments, the pharmaceutical composition is packaged in a packaging material and identified, in or on the packaging material, as a pharmaceutical composition for use in treating a medical condition.

In some embodiments, the pharmaceutical composition is for the treatment of a medical condition associated with glycogen storage disease.

In some embodiments, the medical condition associated with glycogen storage disease is a neurogenerative disease.

In some embodiments, the pharmaceutical composition is formulated for parenteral, mucosal, nasal or oral administration.

According to an aspect of some embodiments of the present invention, there is provided a method of treating glycogen storage disease (GSD) comprising administering to a human in need of such treatment an amount of the disclosed compound in any embodiment thereof.

In some embodiments, the GSD is selected from the group consisting of: GSD type IV, and GSD type VII. In some embodiments, the GSD is Adult polyglucosan body disease (APBD).

According to another aspect, there is provided a diagnostic kit comprising one or more compounds disclosed herein.

In some embodiments, the kit is for detecting GSD.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-C present graph showing dose response of PB reducing hits box plots depicting for each of the 11 concentration dependent hits discovered the influence of concentration on diastase resistant, cell associated, mean PAS intensity, normalized by z-score (FIG. 2A; from left to right corresponding to hits 1 to 11 in FIG. 2B): Arrowheads, median PAS intensity. The boxes delineate upper and lower quartiles from the median, and upper and lower "whiskers" respectively show maximal and minimal mean PAS intensity values. The dots denote outliers. Dose-response (DR) curves of the 11 concentration dependent hits discovered (FIG. 2B): Shown are DR curves of diastase resistant cell associated mean PAS intensities normalized by z-score. Only the descending phases of the hormetic curves are shown, as the concentrations are drawn in a log scale, thus excluding zero concentration. Shown at the bottom are the log EC50 and $R^2$ data for the 11 hits. See molecule structures in FIG. 2B [hit "1" corresponds to UDP #2 (see Tables 1 and 2); hit "2" corresponds to UDP #8; hit "3" corresponds to UDP #6; hit "4" corresponds to UDP #19; hit "5" corresponds to UDP #12; hit "6" corresponds to UDP #11; hit "7" corresponds to UDP #17; hit "8" corresponds to UDP #14; hit "9" corresponds to UDP #5; hit "10" corresponds to UDP #13, and hit "11" corresponds to UDP #15]. FIG. 2C further presents the molecular structures of compounds 1-36, corresponding to Table 1 below.

FIG. 3A and FIG. 3B present data for hits which lowered mean normalized PAS intensity in a non-dose responding manner as presented in FIG. 2A and FIG. 2B, respectively, see molecule structures in FIG. 3B [hit "88D F9" corresponds to UDP #18 (see Table 2); hit "105D G8" corresponds to UDP #1; hit "106D G2" corresponds to UDP #10; hit "106D G5" corresponds to UDP #3; hit "124D F11" corresponds to UDP #16; hit "139D C2" corresponds to UDP #9; hit "140D D4" corresponds to UDP #7, and hit "144D G11" corresponds to UDP #4].

FIGS. 4A-B present: a bar graph showing hit effect on glycogen synthase (GS) activity: an in vitro GS enzyme activity assay (see Example section) was performed in order to test the effect of the 19 hits discovered on GS activity. Each hit compound was used at a final concentration of 50 μM. UDP serves as a positive control for reduction of GS activity. All hits, except for compound #10, have significantly changed GS activity with compounds #6, 7, 8, 12, 18 and 19 increasing and the rest decreasing it (unpaired t-tests, p<0.05). FIG. 4B further presents Table 2 for compound names and molecular structures (also presented in Table 1).

FIG. 5A presents an interactome of the predicted protein targets of the 36 hits (including tautomers and protonation states) discovered. Small yellow circles, hit protein targets; large yellow circles, hit interacting proteins which serve as hubs for protein interaction; red circles, protein targets of the hits known to interact with drugs; blue lines, protein-protein interactions; red arrows, regulatory interactions. See http://www.unihi.org/ for names and descriptions of gene symbols shown. FIG. 5B is an interactome of the subsection of hit-protein targets known to bind drugs and predicted to bind carbohydrate derivatives (red circles in FIG. 5A).

FIG. 6 presents Table 3 summarizing summarizes the common and the difference between the programs: QiqProp (by Schrodinger) SwissADME (the program of Marvin/ChemAxon) and admetSAR @ LMMR.

FIG. 7 presents Table 4 summarizing the QikProp results for descriptors with exceptions.

FIG. 8 presents Table 5 summarizing the SwissADME results for descriptors with exceptions.

FIGS. 9A-B present Table 6 summarizing the AdmetSAR results for descriptors with exceptions (FIG. 9A), and Table 7 summarizing the preferred candidates, assuming the candidates have with less than 4 exceptions (FIG. 9B). Blood-brain barrier (BBB) and central nervous system (CNS)

considerations are not included in the summary presented in FIG. 9A. In addition, for distribution prediction (local in the cell)—see Table 6.

Figure 10:
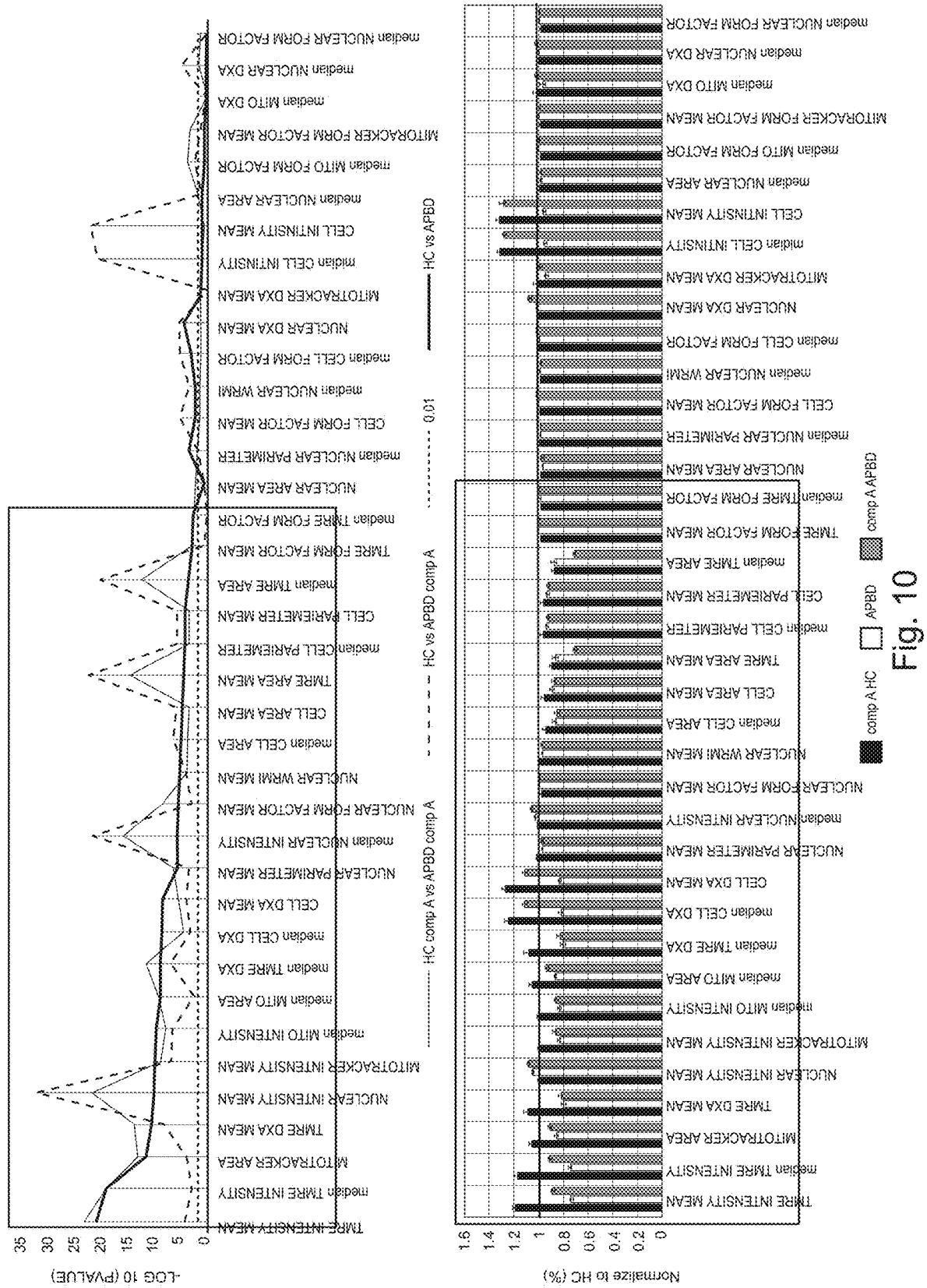

FIG. 10 presents a graph showing multi-parametric cell-phenotypic characterization of healthy control (HC) and APBD skin fibroblasts. Upper panel: the extent of deviation from healthy control of the cell features shown, ordered by the amount of deviation (−log (P value)). Features where the value is above the dashed line (red frame) demonstrate deviation from HC with a p value<0.01. The different comparisons analyzed are shown at the bottom of the panel. The Lower panel shows the deviation as a percentage of HC (horizontal line), according to the treatments indicated below the panel.

Figure 11A:
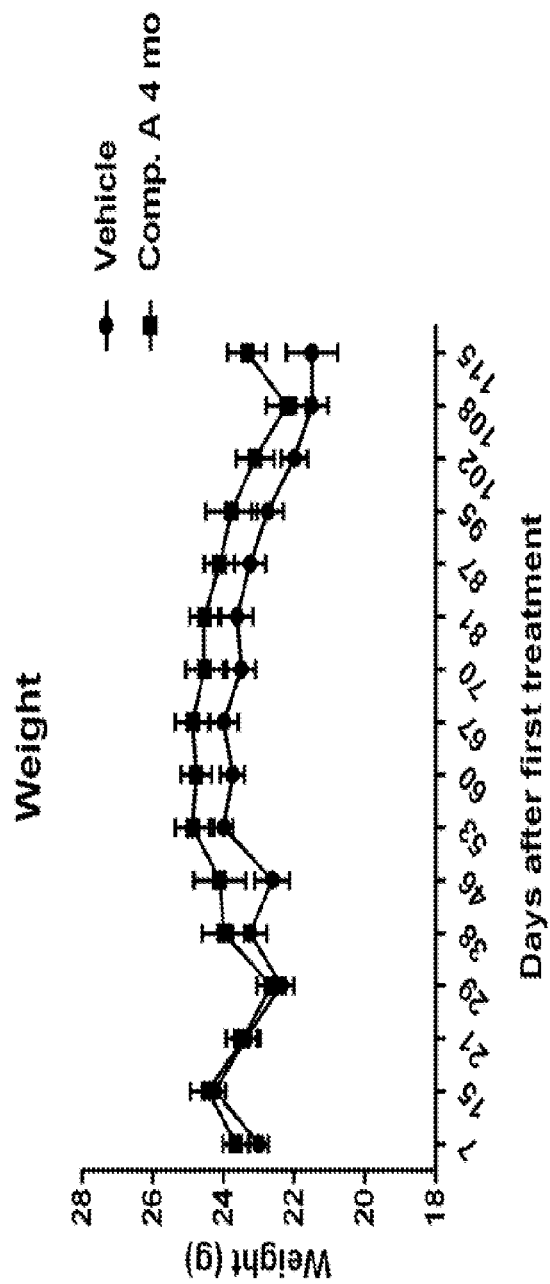

FIGS. 11A-D show weight (in g) as a function of time after treating APBD modeling mice with vehicle, or: compound A, as indicated at 4 months of age (FIG. 11A); as indicated at 6 months of age (at onset) (FIG. 11B); or compound B as indicated at 4 months of age (2 months before onset) (FIG. 11C) or as indicated at 6 months of age (at onset) (FIG. 11D).

FIGS. 12A-D show extension reflex (the degree to which the hind paws open after holding the animal from the tail) as a function of time after treating APBD modeling mice with vehicle, or: compound A, as indicated at 4 months of age (FIG. 12A); as indicated at 6 months of age (at onset) (FIG. 12B); or compound B as indicated at 4 months of age (2 months before onset) (FIG. 12C) or as indicated at 6 months of age (at onset) (FIG. 12D).

FIGS. 13A-D show average front paw grip strength (the force needed to overcome front paw grip of the cage wire) as a function of time after treating APBD modeling mice with vehicle or: compound A, as indicated at 4 months of age (FIG. 13A); as indicated at 6 months of age (at onset) (FIG. 13B); or compound B as indicated at 4 months of age (2 months before onset) (FIG. 13C) or as indicated at 6 months of age (at onset) (FIG. 13D).

Figure 14A:
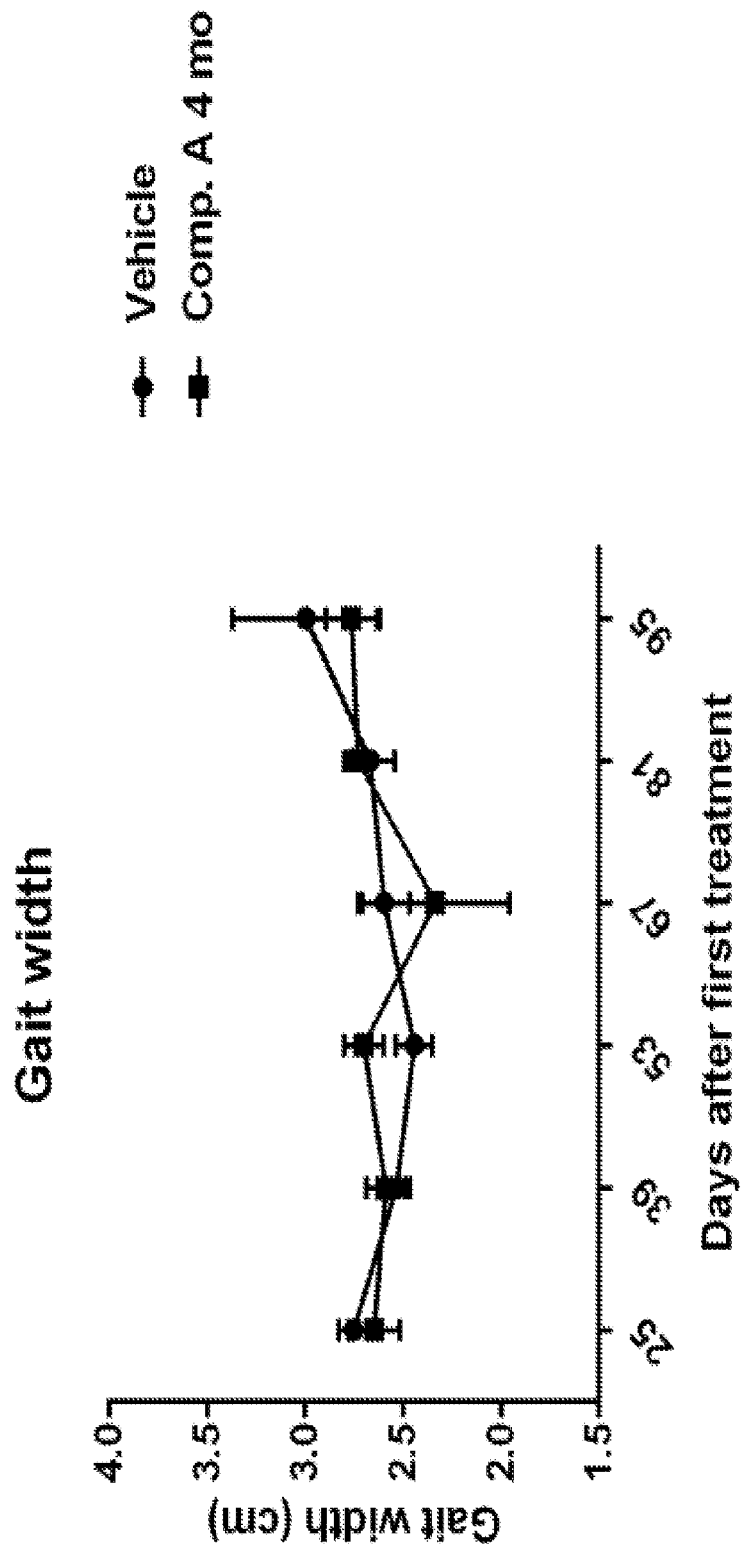
Figure 14B:
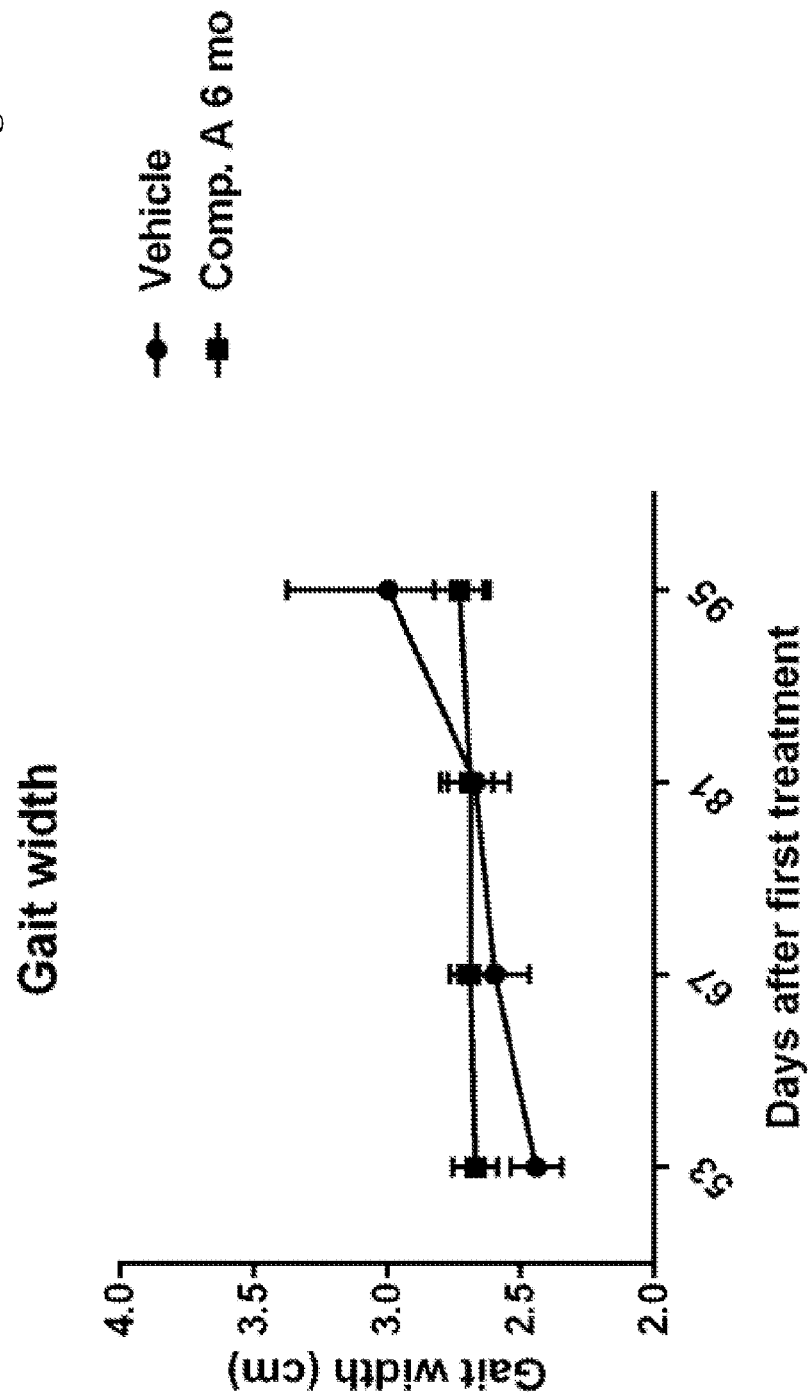
Figure 14D:
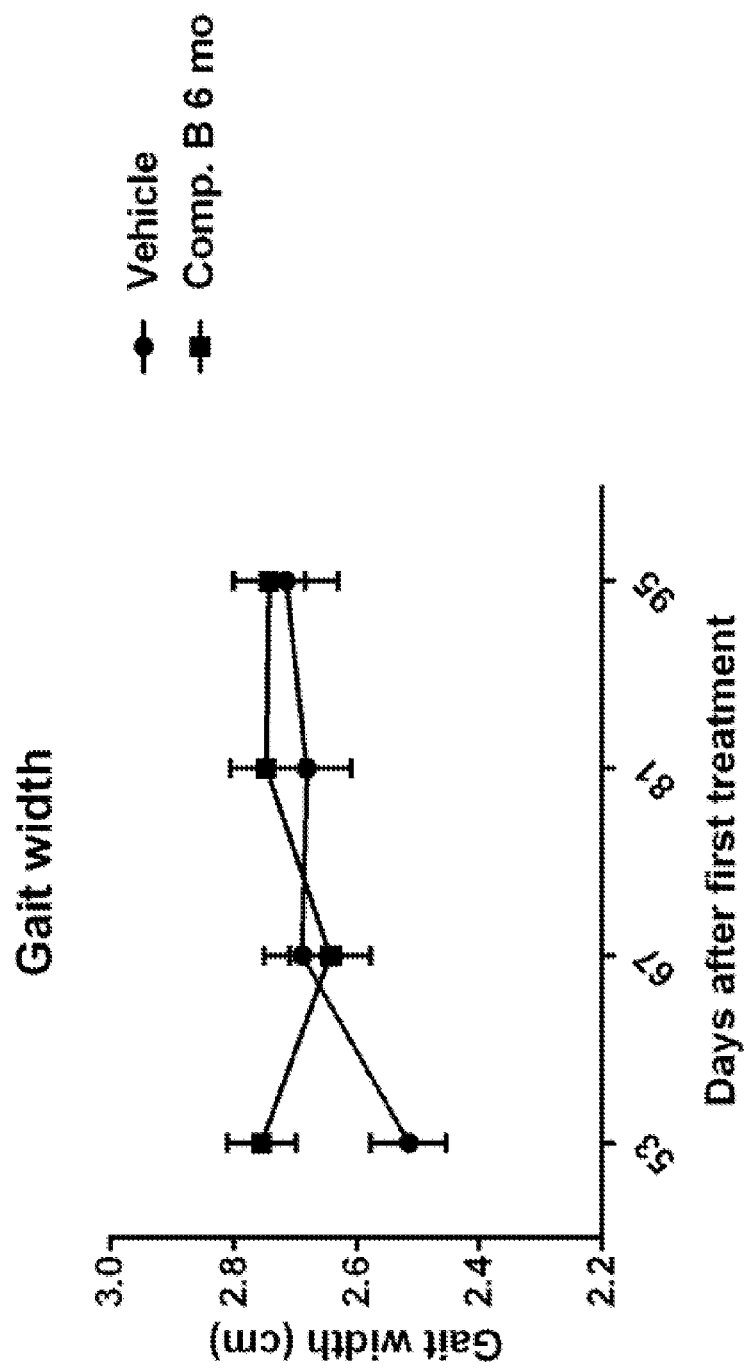

FIGS. 14A-D show average gait width as a function of time after treating APBD modeling mice with vehicle, or: compound A, as indicated at 4 months of age (FIG. 14A); as indicated at 6 months of age (at onset) (FIG. 14B); or compound B as indicated at 4 months of age (2 months before onset) (FIG. 14C) or as indicated at 6 months of age (at onset) (FIG. 14D).

Figure 15A:
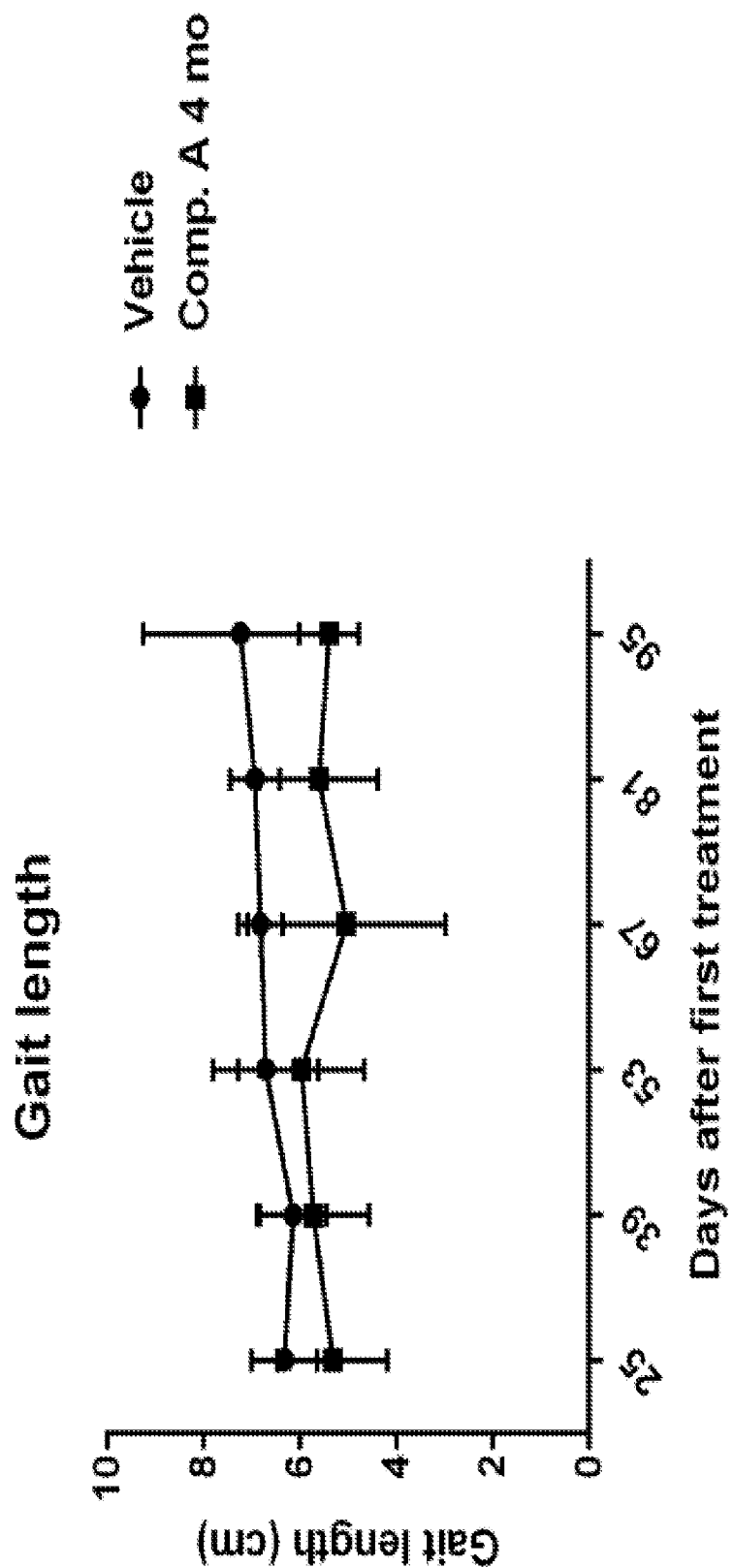
Figure 15D:
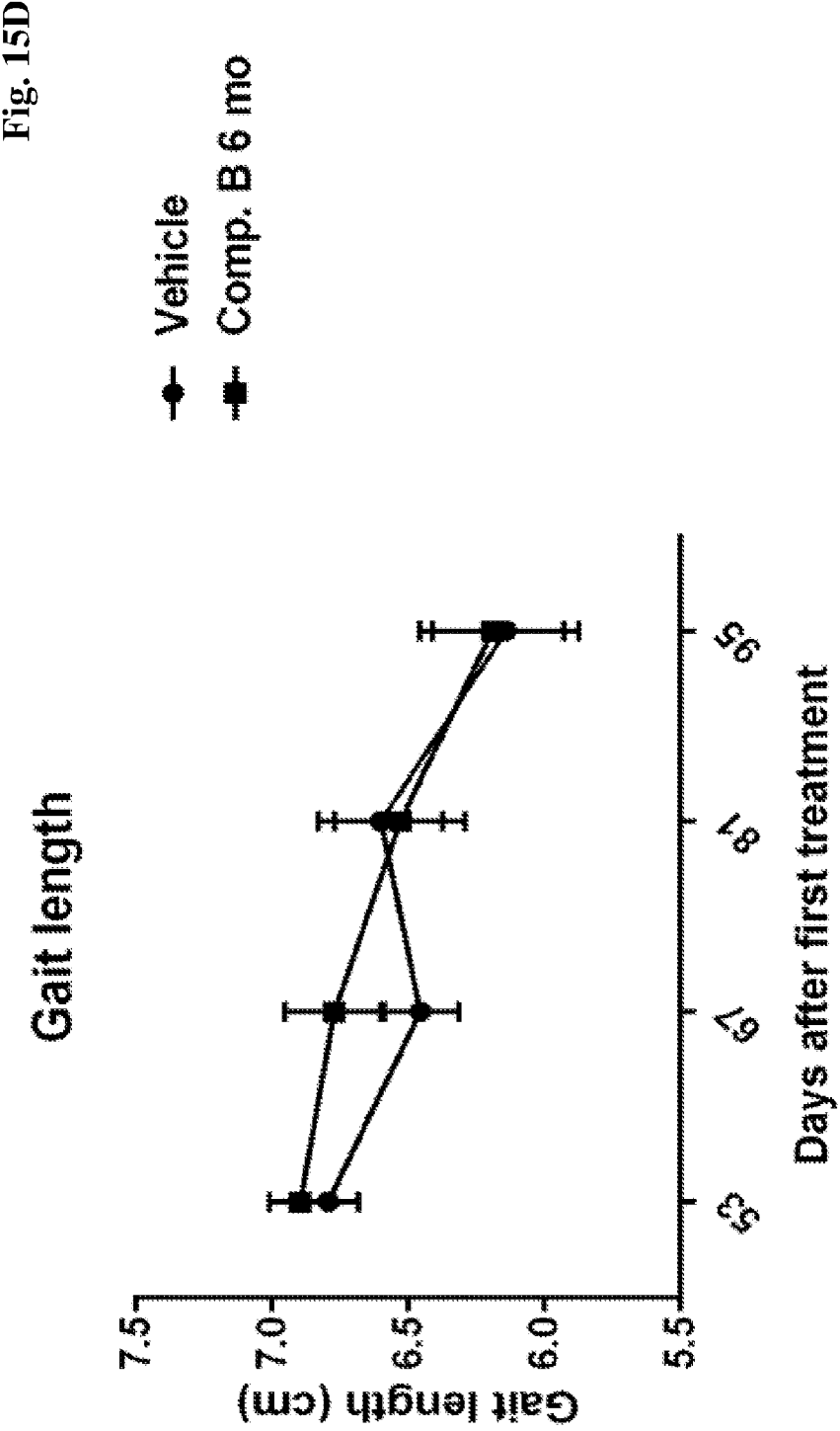

FIGS. 15A-D show average gait length as a function of time after treating APBD modeling mice with vehicle or: compound A, as indicated at 4 months of age (FIG. 15A); as indicated at 6 months of age (at onset) (FIG. 15B); or compound B as indicated at 4 months of age (2 months before onset) (FIG. 15C) or as indicated at 6 months of age (at onset) (FIG. 15D).

Figure 16A:
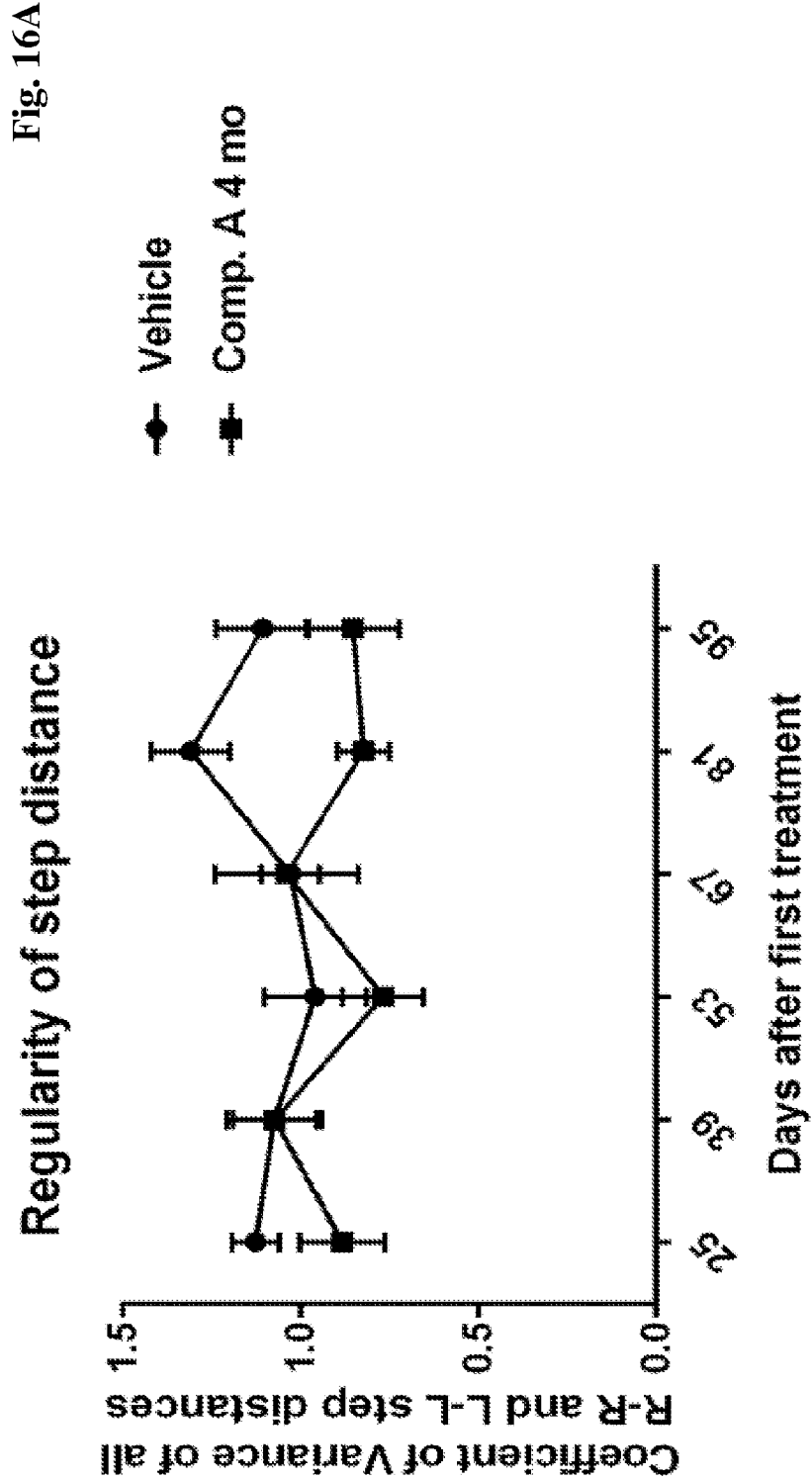
Figure 16C:
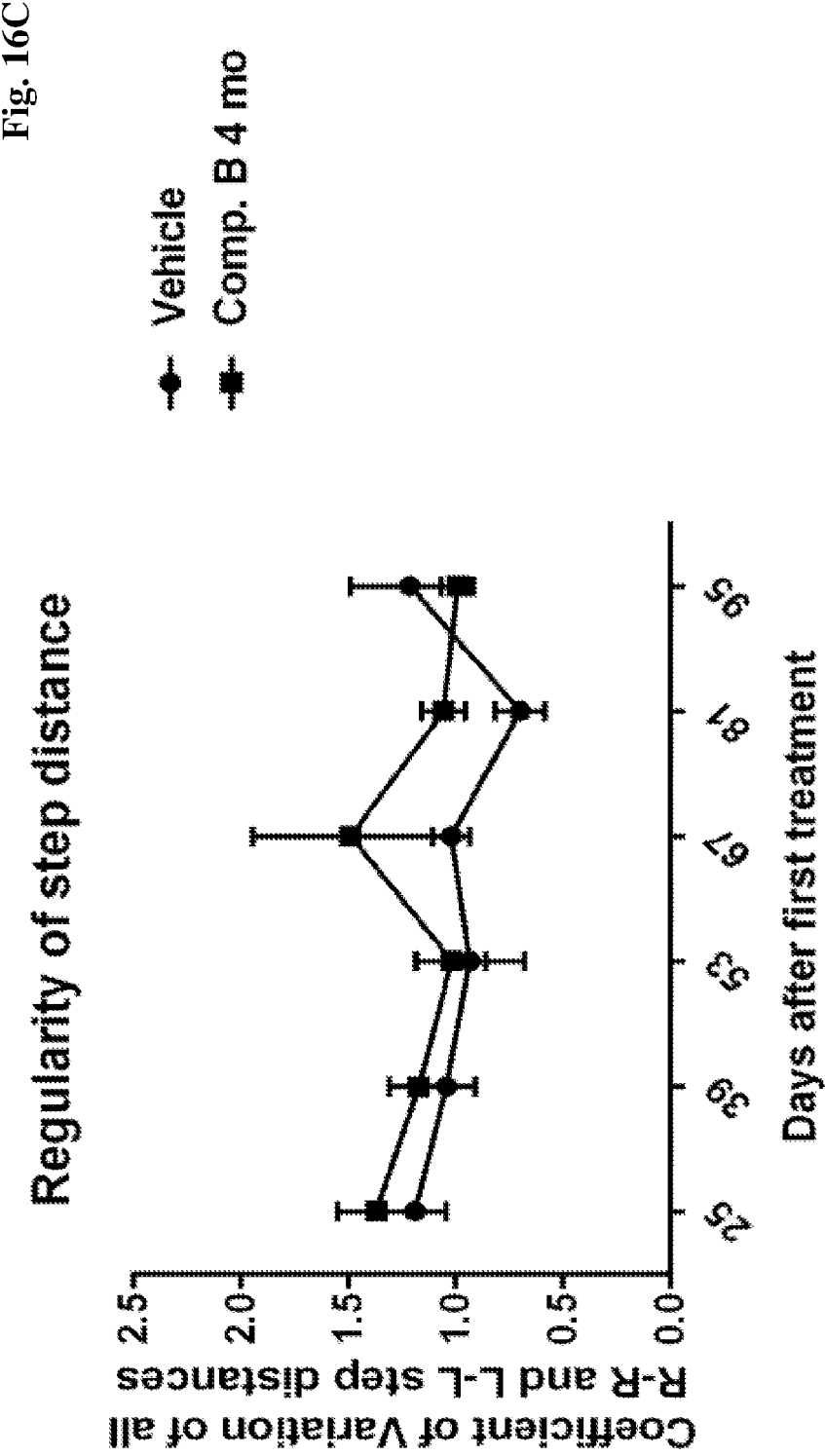
Figure 16D:
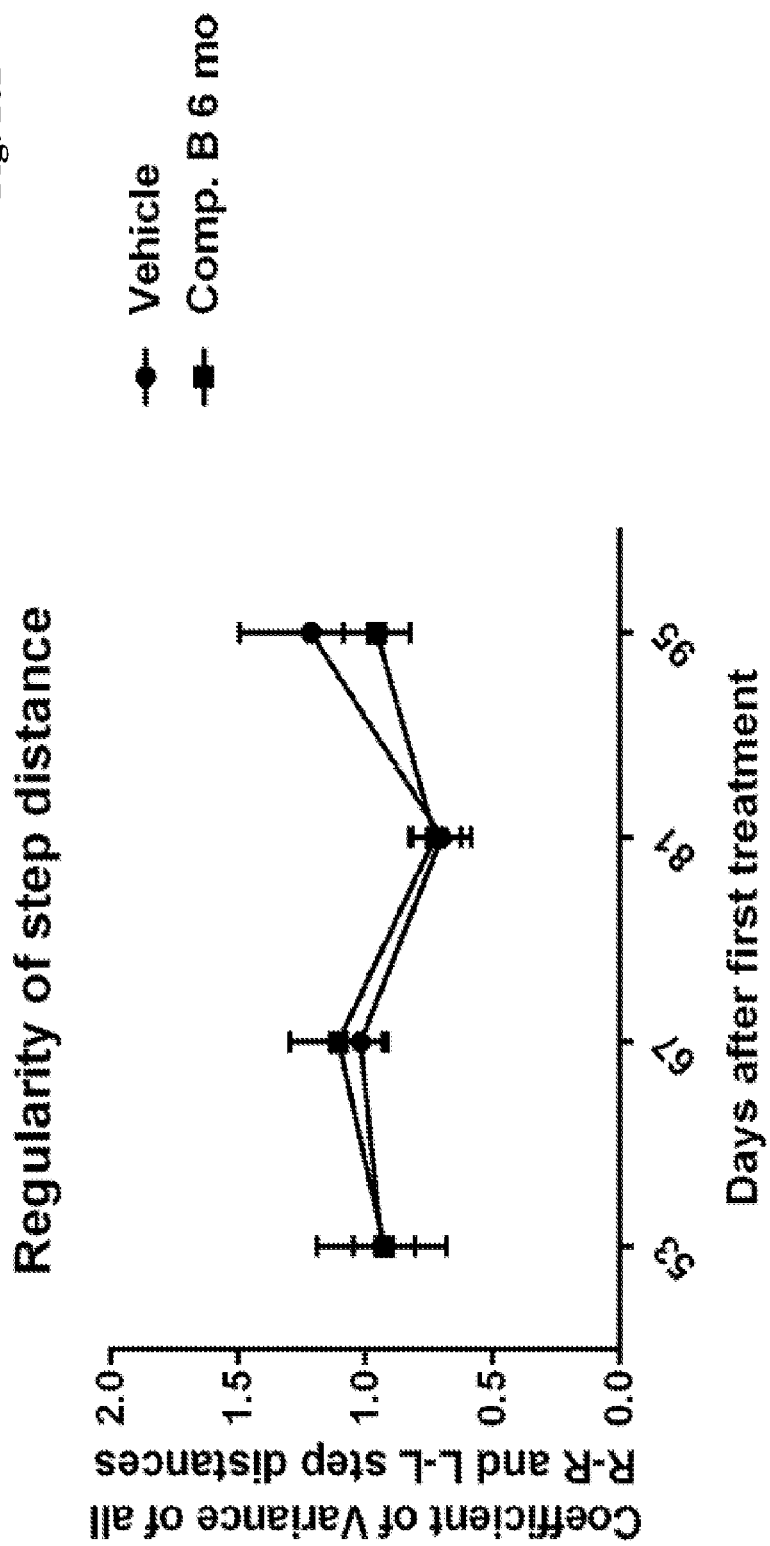

FIGS. 16A-D show average regularity of step distance (the Coefficient of Variance of all R-R and L-L step distances) as a function of time after treating APBD modeling mice with vehicle or: compound A, as indicated at 4 months of age (FIG. 16A); as indicated at 6 months of age (at onset) (FIG. 16B); or compound B as indicated at 4 months of age (2 months before onset) (FIG. 16C) or as indicated at 6 months of age (at onset) (FIG. 16D).

FIGS. 17A-D show average uniformity of step alternation expressed as the mean of the absolute value of 0.5 minus the ratio of R-L distance to R-R step distance (|0.5−(R−L/R−R)|) and vice versa. Uniformity of step alteration is plotted as a function of time after treating APBD modeling mice with vehicle or: compound A, as indicated at 4 months of age (FIG. 17A); as indicated at 6 months of age (at onset) (FIG.

Figure 17B:
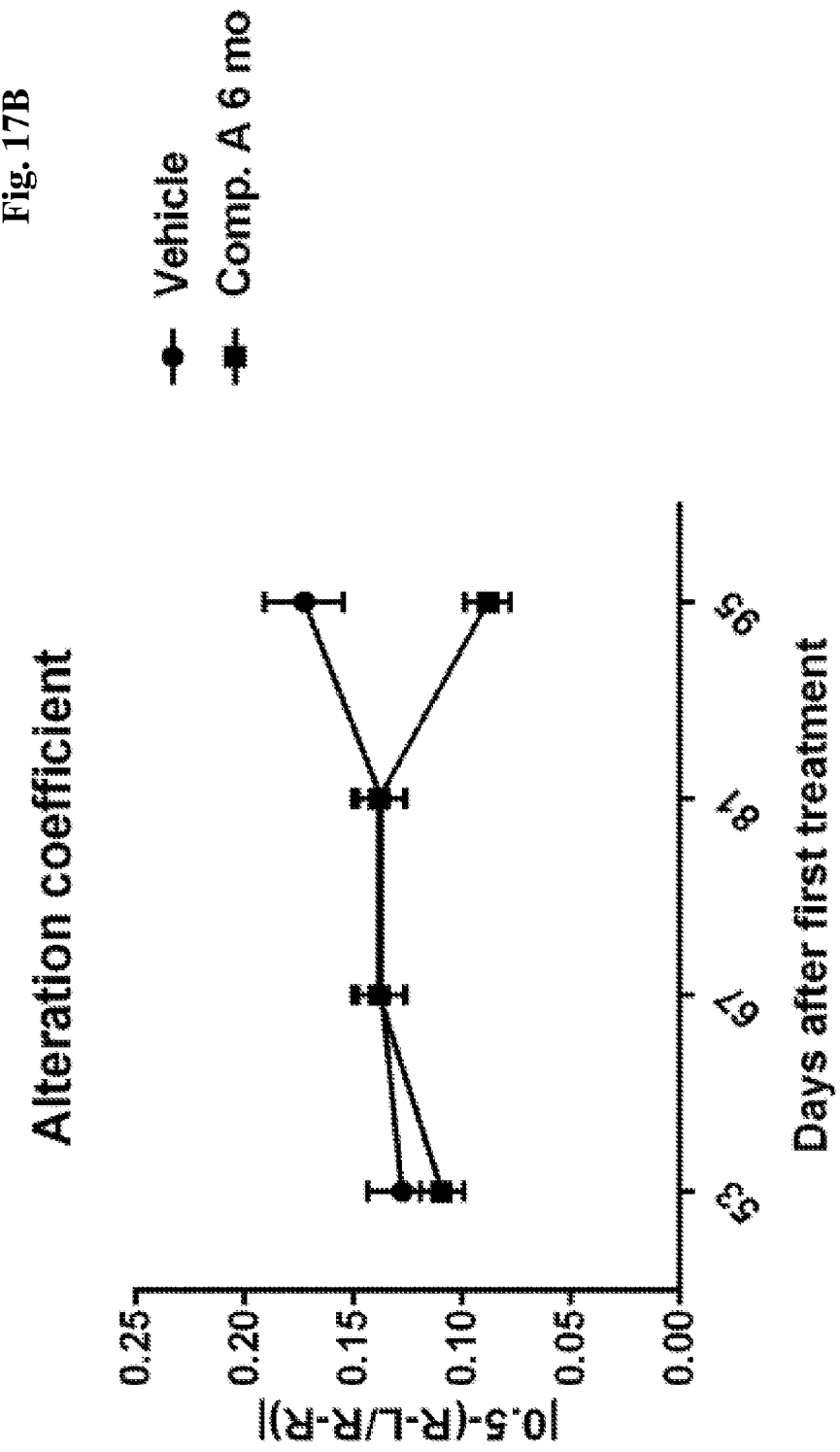
Figure 17C:
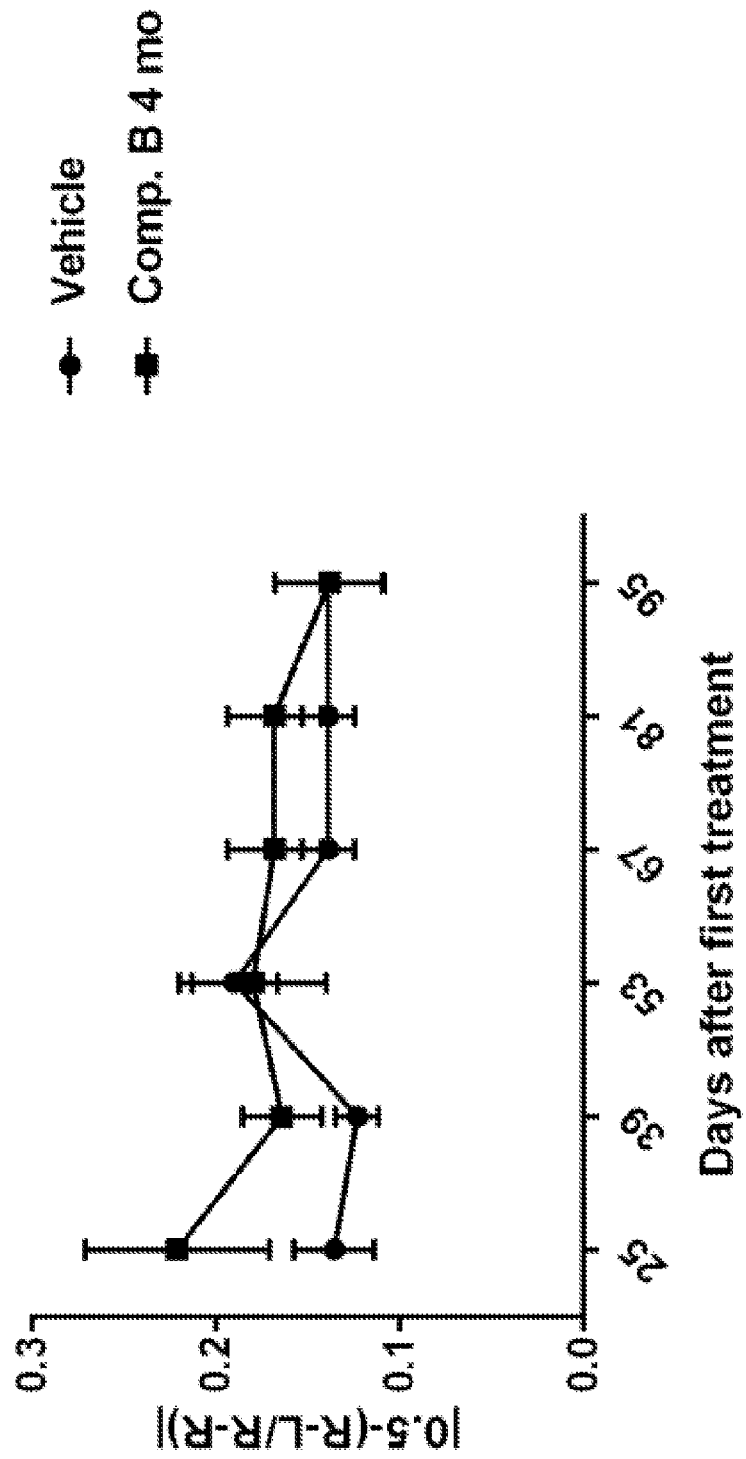
Figure 17D:
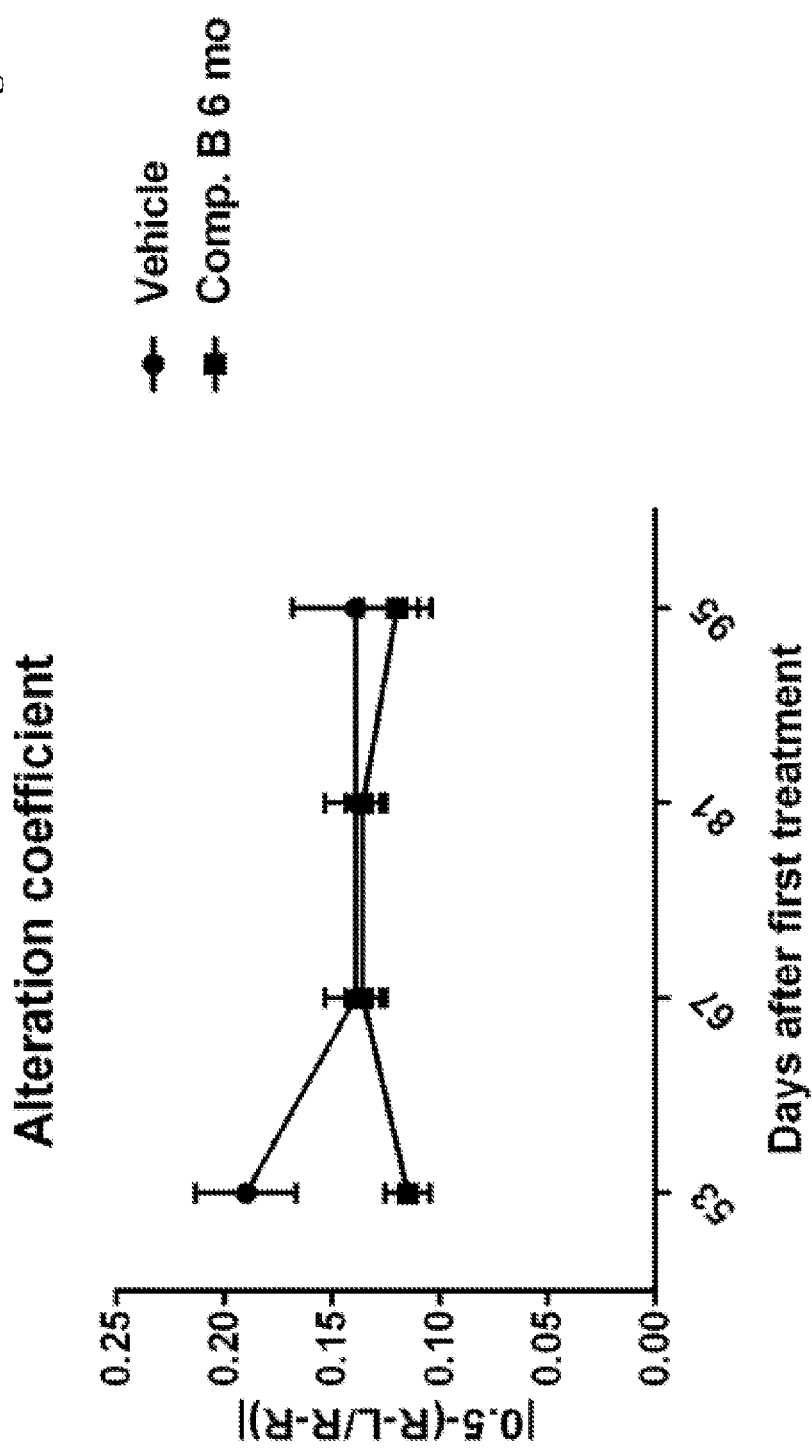

17B); or compound B as indicated at 4 months of age (2 months before onset) (FIG. 17C) or as indicated at 6 months of age (at onset) (FIG. 17D).

Figure 18A:
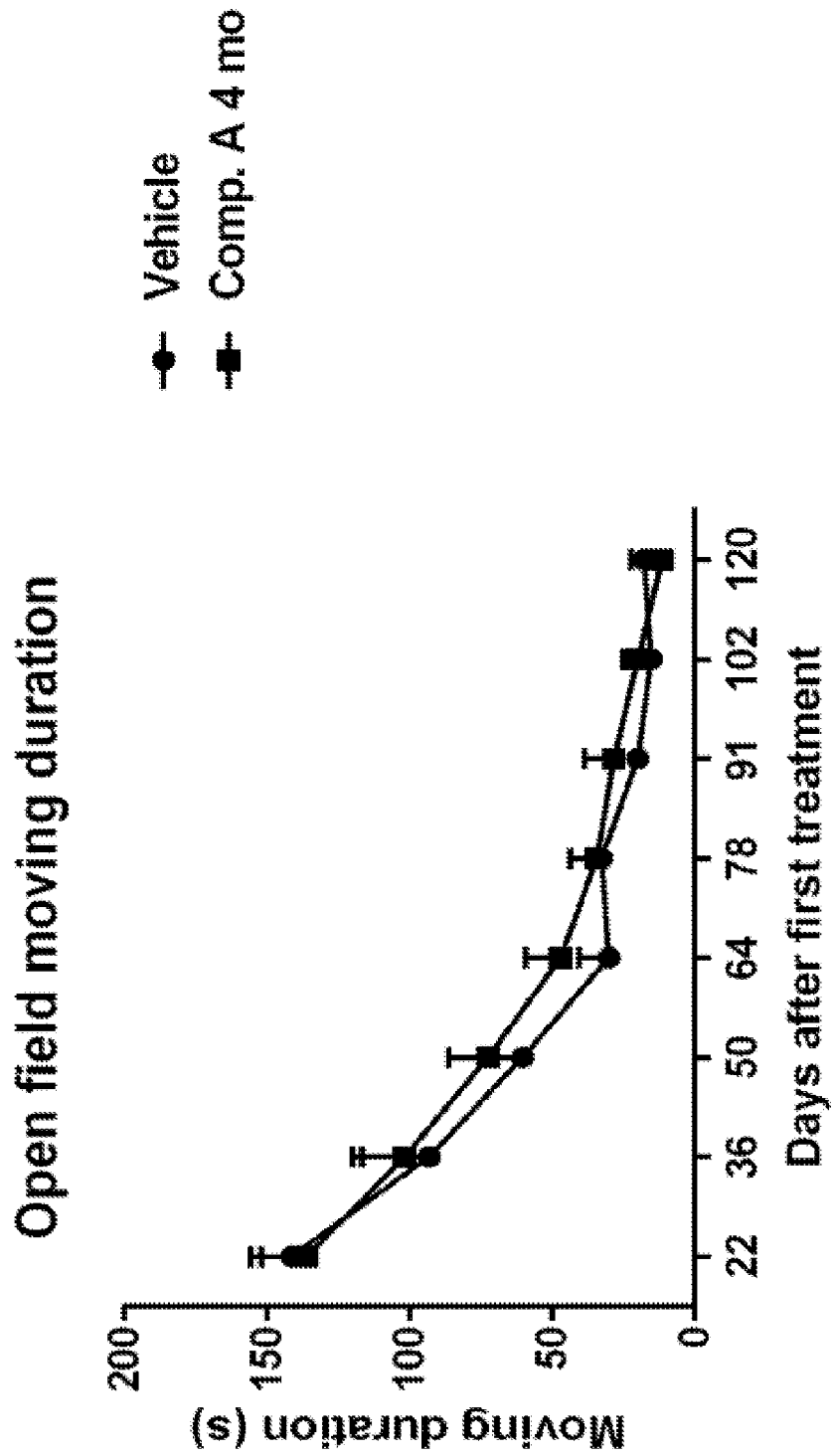

FIGS. 18A-D show average duration in movement in an open field test as a function of time after treating APBD modeling mice with vehicle or: compound A, as indicated at 4 months of age (FIG. 18A); as indicated at 6 months of age (at onset) (FIG. 18B); or compound B as indicated at 4 months of age (2 months before onset) (FIG. 18C) or as indicated at 6 months of age (at onset) (FIG. 18D).

Figure 19A:
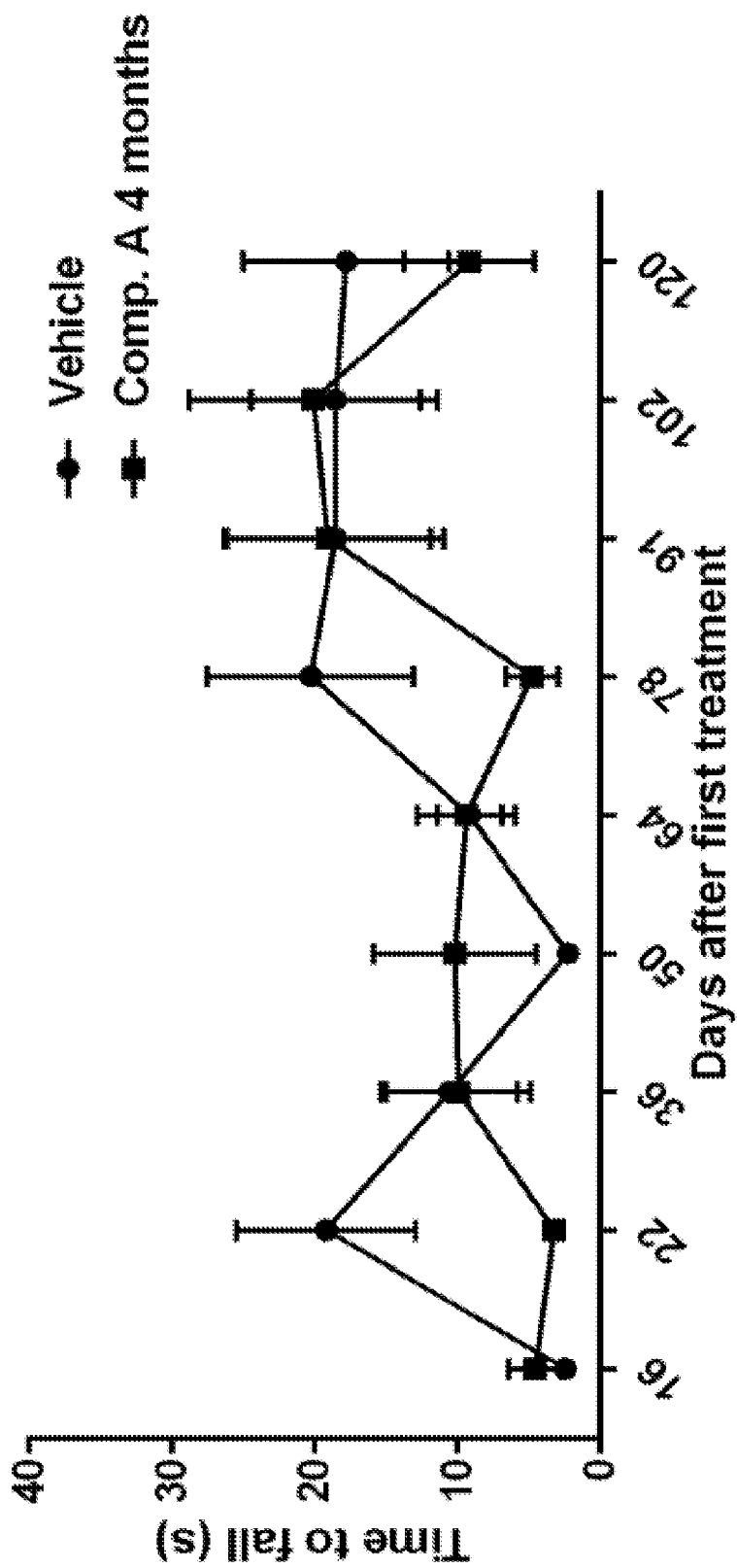

FIGS. 19A-D show average latency to fall off a metal wire as a function of time after treating APBD modeling mice with vehicle or: compound A, as indicated at 4 months of age (FIG. 19A); as indicated at 6 months of age (at onset) (FIG. 19B); or compound B as indicated at 4 months of age (2 months before onset) (FIG. 19C) or as indicated at 6 months of age (at onset) (FIG. 19D).

Figure 20C:
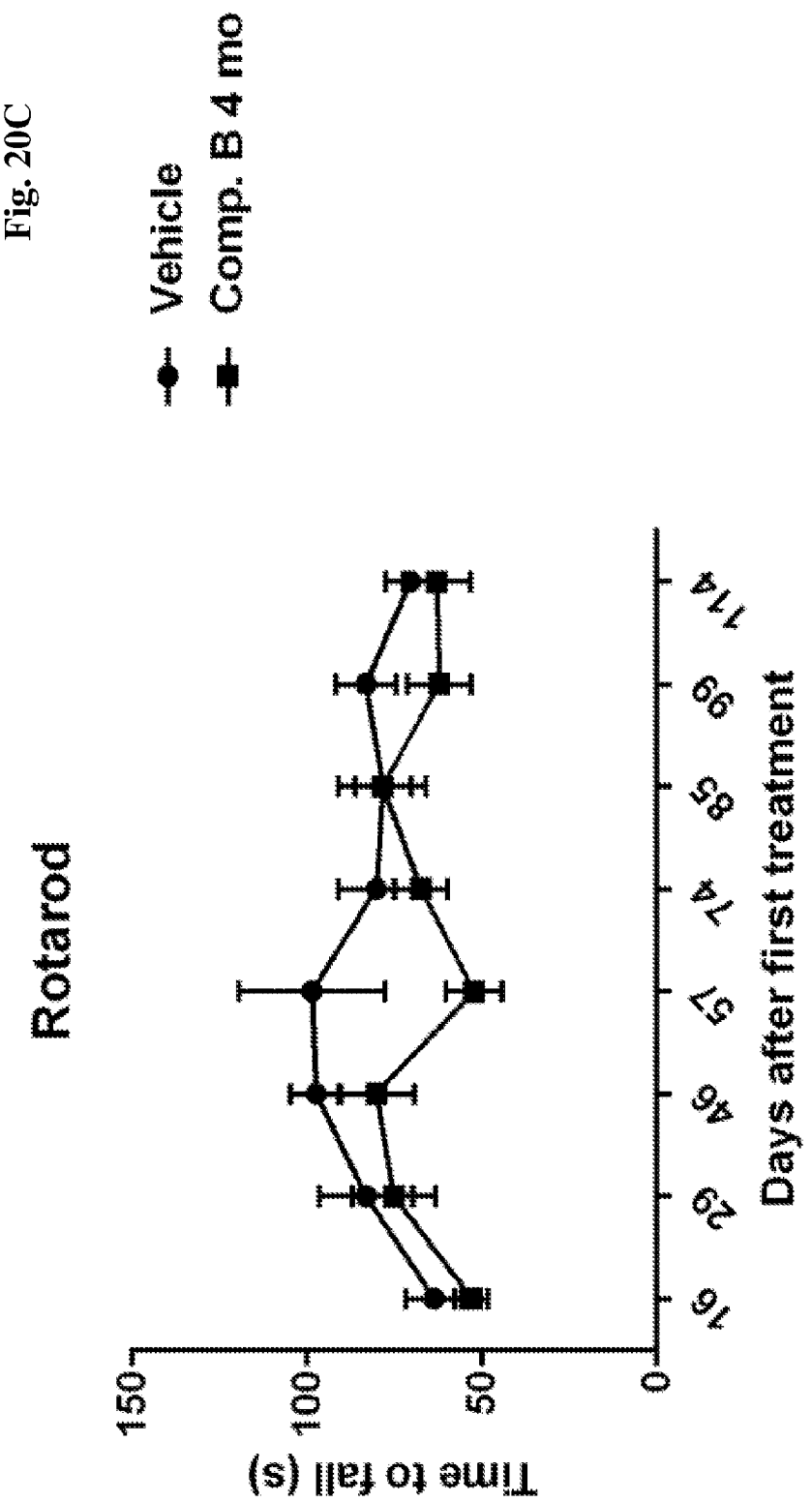
Figure 20D:
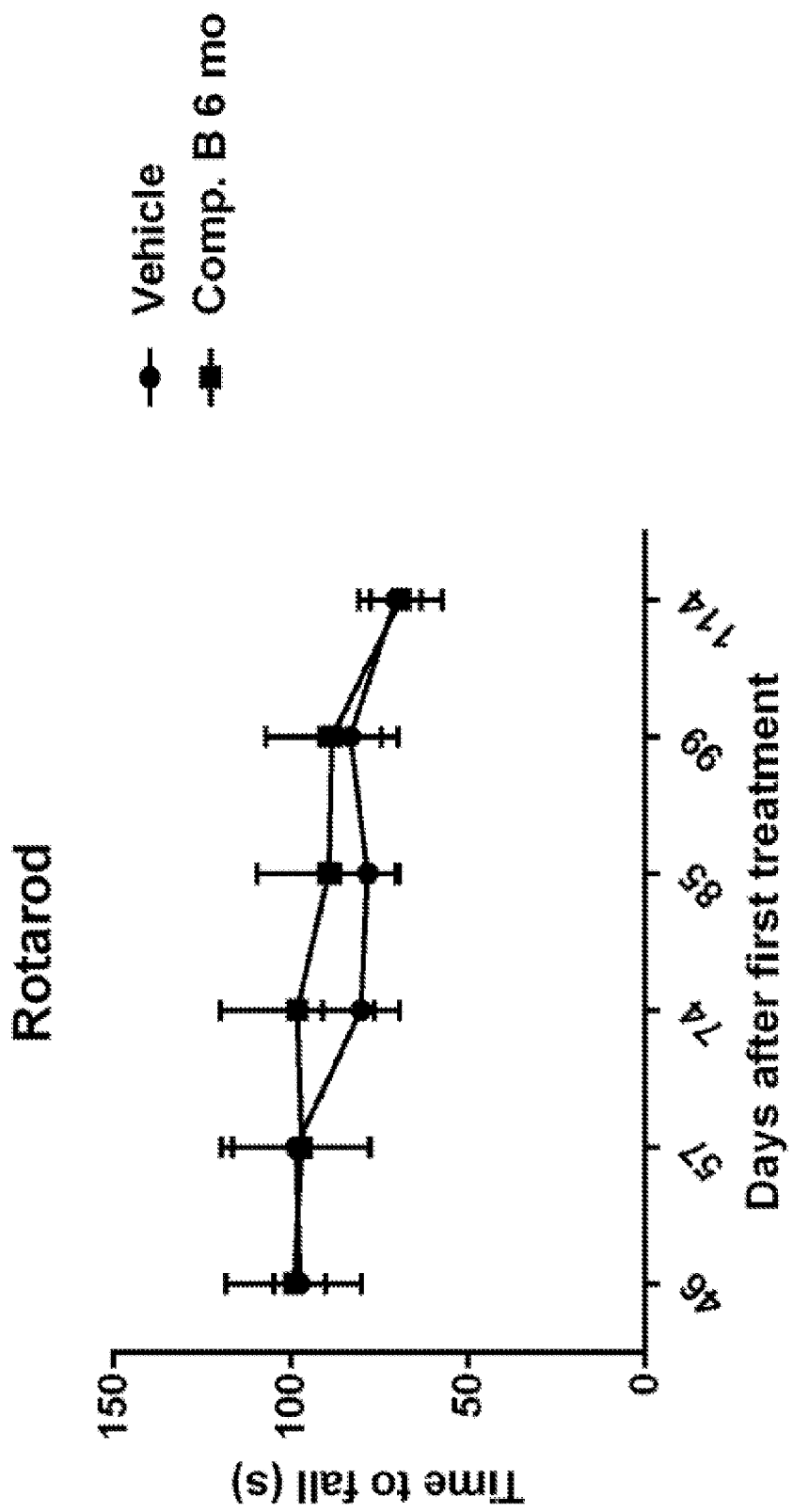

FIGS. 20A-D show average latency to fall off a rotating cylinder (rotarod) as a function of time after treating APBD modeling mice with vehicle or: compound A, as indicated at 4 months of age (FIG. 20A); as indicated at 6 months of age (at onset) (FIG. 20B); or compound B as indicated at 4 months of age (2 months before onset) (FIG. 20C) or as indicated at 6 months of age (at onset) (FIG. 20D).

DETAILED DESCRIPTION

The present invention, in some embodiments thereof, relates to compounds and compositions comprising same for reducing or preventing diseases or disorders characterized by deposition, accumulation or aggregation of polyglucosan bodies.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect of some embodiments of the present invention, there is provided a compound represented by Formula I):

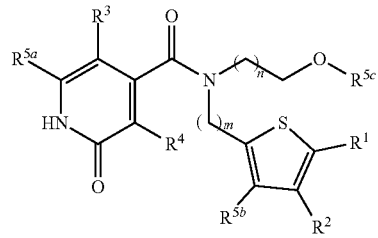

wherein n and m are each integers representing, independently, 1, 2, or 3;
wherein:
$R^1$ to $R^4$ represent substituents, independently in each occurrence comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted, and $R^{5a-c}$ represent $C_{1-6}$ alkyl.

In some embodiments, $R^{5a}$ is methyl. In some embodiments, $R^{5b}$ is methyl. In some embodiments, $R_{5c}$ is methyl. In some embodiments, each of $R^{5a-c}$ represents methyl.

In some embodiments, at least one, two, or three substituents from $R^1$ to $R^4$ represent hydrogen. In some embodiments, each of $R^1$ to $R^4$ represents hydrogen.

In some embodiments, n is 1.

In some embodiments, m is 1.

In some embodiments, m and n are each 1.

In exemplary embodiments, the compound of Formula I is represented by Formula Ia (compound 16 in Table 1, or a tautomer thereof, compound 15 therein, see FIG. 2C):

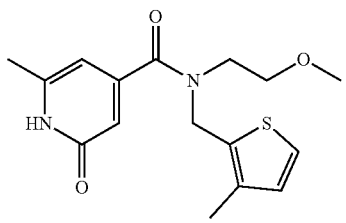

N-(2-methoxyethyl-6-methyl-N-[(3-methyl-2-thienyl)methyl]-2-oxo-1,2-dihydropyridine-4-carboxamide Hereinthroughout, by "compound", it is also meant to include pharmaceutically acceptable salt thereof.

According to an aspect of some embodiments of the present invention, there is

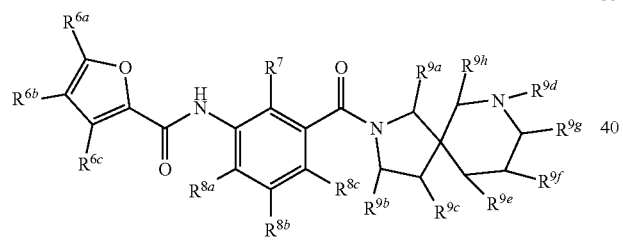

provided a compound represented by Formula II:

wherein $R^{6a}$ to $R^{6c}$, $R^7$, $R^{8a}$ to $R^{8c}$, and $R^{9a}$ to $R^{9h}$, independently and in each occurrence, represent at least one substituent, comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted;

In some embodiments, one or more substituents from $R^{9a}$ to $R^{9h}$ is $C_{1-6}$ alkyl. In some embodiments, one or more substituents from $R^{9a}$ to $R^{9h}$ are hydrogen.

In some embodiments, $R^7$ is $C_{1-6}$ alkyl.

In some embodiments, the alkyl is methyl. In some embodiments, $R^{9d}$ is hydrogen.

In some embodiments, the compound represented by Formula II is represented by Formula IIa (compound 27 in Table 1 below):

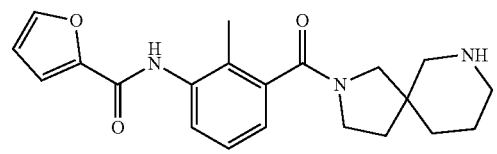 [SMILES: Cc1c(NC(=O)c2ccco2)cccc1C(=O)N1CCC2(CCCNC2)C1]

N-[3-(2,7-diazaspiro[4.5]dec-2-ylcarbonyl)-2-methylphenyl]-2-furamide
or any isomer or tautomer thereof, for example Formula IIb (compound 28 in Table 1 below):

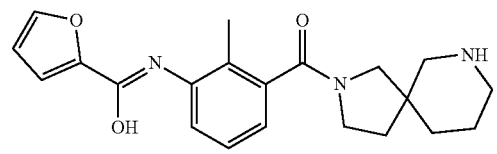 [SMILES: Cc1c(/N=C(\O)c2ccco2)cccc1C(=O)N1CCC2(CCCNC2)C1]

(Z)—N-(2-methyl-3-(2,7-diazaspiro[4.5]decane-2-carbonyl)phenyl)furan-2-carbimidic acid According to an aspect of some embodiments of the present invention, there is provided a compound represented by is represented by Formula III:

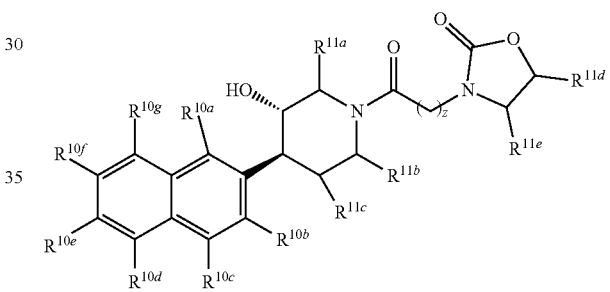

wherein $R^{10a}$ to $R^{10g}$ represent substituents, independently in each occurrence comprising or being selected from the group consisting of hydrogen, alkyl, cycloalkyl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, substituted or non-substituted;

z is an integer representing, independently, 1, 2, or 3;

$R^{11a}$ to $R^{11e}$ represent at least one substituent selected from hydrogen and $C_{1-6}$ alkyl.

In some embodiments, z is 1.

In some embodiments, the compound represented by Formula III is in the form of Formula IIIa (compound 30 in Table 1):

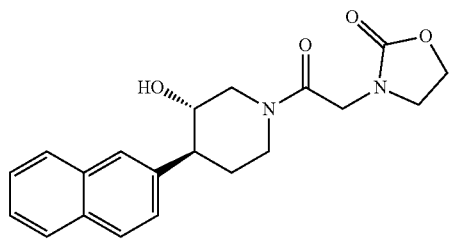 [SMILES: O=C(CN1CCOC1=O)N1CC[C@@H](c2ccc3ccccc3c2)[C@H](O)C1]

3-{2-[(3S*,4S*)-3-hydroxy-4-(2-naphtyl)piperidin-1-yl]-2-oxoethyl}-1,3-oxazolidin-2-one According to an aspect of some embodiments of the present invention, there is provided a compound represented by Formula IV:

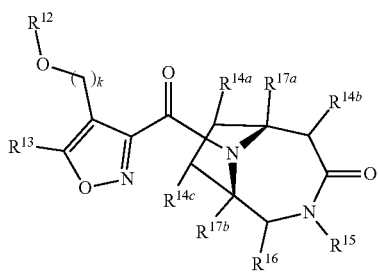

wherein $R^{12}$, $R^{13}$, $R^{14a}$-$R^{14c}$, $R^{15}$, $R^{16}$, $R^{17a}$-$R^{17b}$ represent substituents, independently in each occurrence comprising or being selected from the group consisting of hydrogen and $C_{1-6}$ alkyl; and k is an integer representing, independently, 1, 2, or 3.

In some embodiments, k is 1.

In some embodiments, $R^{12}$, $R^{13}$, and $R^{15}$ are methyl.

In some embodiments, $R^{17a}$, and $R^{17b}$ are hydrogen.

In some embodiments, the compound represented by Formula IV is in the form of Formula IVa (compound 24 in Table 1):

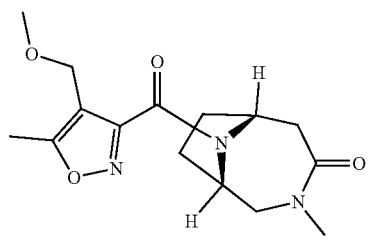

(1S*,6R*)-9-{[4-(methoxymethyl)-5-methylisoxazol-3-yl]carbonyl}-3-methyl-3,9-diazabicyclo[4.2.1]nonan-4-one According to an aspect of some embodiments of the present invention, there is provided a compound represented by any one of compounds 1 to 36 disclosed in Table 1 below (see molecular structure in FIG. 2C):

TABLE 1

| Name | # of Ionizations | # of Tautomers | Structure | Structure | Structure | Structure |
|---|---|---|---|---|---|---|
| N-(2,4-dimethylphenyl)-3-[4-phenyl-5-(tetrahydrofuran-3-yl)-1H-imidazol-1-yl]propanamide UDP# 18 | 1 | 2 | Compound 1 | Compound 2 | | |
| 3-fluoro-4-{6-[(pyridin-3-ylmethyl)amino]-1H-pyrrolo[2,3-b]pyridin-4-yl}phenol UDP # 1 | 1 | 4 | Compound 3 | Compound 4 | Compound 5 | Compound 6 |
| N-[(1,5-dimethyl-1H-indazol-3-yl)methyl]-2-(3-pyrrolidinyl)benzamide UDP # 10 | 1 | 1 | Compound 7 | | | |
| 3-[2-(3-cyclopropyl-1,4,6,7-tetrahydro-5H-pyrazolo[4,3-c]pyridin-5-yl)-2-oxoethyl]-4-(3-methylbutyl)-2-piperazinone UDP # 3 | 1 | 2 | Compound 8 | Compound 9 | | |
| 2-(4-methoxy-2-methylphenyl)-5-methylpyrimidin-4-amine UDP # 16 | 1 | 2 | Compound 10 | Compound 11 | | |
| (1S*,6R*)-9-{[1-methyl-3-(2-thienyl)-1H-pyrazol-5-yl]carbonyl}-3,9-diazabicyclo[4.2.1]nonan-4-one UDP # 9 | 1 | 1 | Compound 12 | | | |

TABLE 1-continued

| Name | # of Ionizations | # of Tautomers | Structure | Structure | Structure | Structure |
|---|---|---|---|---|---|---|
| 4-isopropyl-2-methyl-6-{4-[(3-methylpyridin-2-yl)methyl]piperazin-1-yl}pyrimidine UDP # 7 | 2 | 1 | Compound 13 | Compound 14 | | |
| N-(2-methoxyethyl)-6-methyl-N-[(3-methyl-2-thienyl)methyl]-2-oxo-1,2-dihydropyridine-4-carboxamide UDP # 4 ("Compound A") | 1 | 2 | Compound 15 | Compound 16 | | |
| 6-[4-(2,6-difluoro-4-methoxybenzyl)piperazin-1-yl]pyrazine-2-carboxamide UDP # 2 | 2 | 1 | Compound 17 | Compound 18 | | |
| 5-methyl-1-[4-(4H-1,2,4-triazol-4-yl)phenyl]pyrrolidin-2-one UDP # 8 | 1 | 1 | Compound 19 | | | |
| 4-[4-(3-fluorophenyl)-1H-pyrazol-5-yl]-1-[(1-isopropyl-1H-imidazol-2-yl)methyl]piperidine UDP # 6 | 2 | 2 | Compound 20 | Compound 21 | Compound 22 | Compound 23 |
| (1S*,6R*)-9-{[4-(methoxymethyl)-5-methylisoxazol-3-yl]carbonyl}-3-methyl-3,9-diazabicyclo[4.2.1]nonan-4-one UDP # 19 ("Compound B") | 1 | 1 | Compound 24 | | | |
| 7-(3-chlorophenyl)-4-(3-furoyl)-2,3,4,5-tetrahydro-1,4-benzoxazepin-9-ol UDP # 12 | 1 | 1 | Compound 25 | | | |
| N-[(5-ethylpyridin-2-yl)methyl]-N-methyl-2,1,3-benzoxadiazole-5-carboxamide 1-oxide UDP # 11 | 1 | 1 | Compound 26 | | | |
| N-[3-(2,7-diazaspiro[4.5]dec-2-ylcarbonyl)-2-methylphenyl]-2-furamide UDP # 17 | 1 | 2 | Compound 27 | Compound 28 | | |
| 4-tert-butyl-2-(4H-1,2,4-triazol-4-yl)phenol UDP # 14 | 1 | 1 | Compound 29 | | | |
| 3-{2-[(3S*,4S*)-3-hydroxy-4-(2-naphthyl)piperidin- | 1 | 1 | Compound 30 | | | |

TABLE 1-continued

| Name | # of Ionizations | # of Tautomers | Structure | Structure | Structure | Structure |
|---|---|---|---|---|---|---|
| 1-yl]-2-oxoethyl}-1,3-oxazolidin-2-one UDP # 5 | | | | | | |
| 2-(2-amino-4,6-dimethylpyrimidin-5-yl)-N-[(3S*,4R*)-4-ethoxytetrahydrofuran-3-yl]acetamide UDP # 13 | 1 | 2 | Compound 31 | Compound 32 | | |
| N-[2-(4,5,6,7-tetrahydro-2H-indazol-3-yl)ethyl]-3-azaspiro[5.5]undecan-9-amine UDP # 15 | 2 | 2 | Compound 33 | Compound 34 | Compound 35 | Compound 36 |

In some embodiments, the compound represented by Formula I, in an embodiment thereof, is for the treatment of a medical condition. In some embodiments, the compound represented by Formula II, in an embodiment thereof, is for the treatment of a medical condition. In some embodiments, the compound represented by Formula III, in an embodiment thereof, is for the treatment of a medical condition. In some embodiments, the compound represented by Formula V, in an embodiment thereof, is for the treatment of a medical condition. In some embodiments, the compound represented by Formula IV, in an embodiment thereof, is for the treatment of a medical condition.

In some embodiments, the compound represented by any one of Formulae 1 to 36 (presented in Table 1 and in FIG. 2C) is for the treatment of a medical condition.

In some embodiments, the medical condition is a disease or disorder. In some the disease or disorder is glycogen storage disorder (GSD). In some embodiments, the GSD is associated with glycogen-branching enzyme deficiencies.

In some embodiments, the medical condition is one or more from, without being limited thereto, adult polyglucosan body disorder (APBD), Andersen disease, Forbes disease, and Danon disease.

In some embodiments, by GSD, or by "medical condition associated with "glycogen-branching enzyme deficiencies", it is meant to refer to diseases or disorders characterized by deposition, accumulation or aggregation of polyglucosan bodies in muscle, nerve and/or various other tissues of the body. In some embodiments, the medical condition is characterized by dysfunction of the central and/or peripheral nervous systems of a subject.

Various methods for personalizing treatment, prevention, or reduction of the incidence or severity of GSD and other disorders related to the accumulation of polyglucosan bodies are encompassed in embodiments of the invention.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" (or any grammatical derivative thereof) includes abrogating, prophylaxis, substantially inhibiting, slowing or reversing the progression of a condition/disease, substantially ameliorating clinical or aesthetical symptoms of a condition/disease or substantially preventing the appearance of clinical or aesthetical symptoms of a condition/disease.

According to one embodiment, the compounds of this aspect of the present invention are used to treat neurodegenerative diseases. According to one embodiment, the compounds of the present invention are used to treat inflammatory diseases.

According to one embodiment, the compounds of this aspect of the present invention are used to treat GSD-associated cancer.

In some embodiments, the compound of any formulae disclosed herein (e.g., Formulae I to IV) is characterized by an activity that decreases polyglucosan body (PB) cellular content. In some embodiments, by "decreases PB cellular content", it is meant to refer to shaping (e.g., reducing) the size of PB. In some embodiments, by "decreases PB cellular content", it is meant to refer to degrading the PB. (e.g., by modulating glycogen branching enzyme, GBE).

In some embodiments, the compound of any formulae disclosed herein (e.g., Formulae I to IV) is capable of modulating (e.g., inhibiting, or in some embodiment, increasing) an activity of at least one enzyme.

In some embodiments, the compound of any formulae disclosed herein (e.g., Formulae I to IV) is capable of inhibiting one or more enzymes. Non-limiting examples of such enzyme is glycosyltransferase e.g., glycogen synthase (GS) and protein phosphatase-1 (PP1). The control of glycogen synthase may be a key step in regulating glycogen metabolism and glucose storage.

Further embodiments of the inhibitory activity are described in the Examples section below.

The term "inhibitory" or any grammatical derivative thereof, as used herein in the context of enzymes refers to being capable of preventing, blocking, attenuating, or reducing the activity of an enzyme.

In some embodiments, by "reducing the activity", it is meant to refer to an activity being reduced by at least 20%, at least 30%, at least 40%, at least 50%, at least 60%, at least 70%, at least 80%, or at least 90%, including any value and range therebetween, relative to comparable situation lacking the presence of the disclosed compound or a composition of matter containing same.

The term "therapeutically effective amount" as used herein refers to an amount of an agent which is effective, upon single or multiple dose administration to the subject, in providing a therapeutic benefit to the subject and/or in preventing tissues and cells damage. In one embodiment, the therapeutic benefit is inhibiting or ameliorating symptoms of such damage. As used herein, the term "administering" refers to bringing mammalian cells in contact with the compound or composition of the present invention. The effective amount of the composition used to practice the present invention for therapeutic treatment of conditions caused by the manner of administration, the age, body weight, and general health of the patient. Ultimately, the attending physician may decide the appropriate amount and dosage regimen. As further described below, such amount is referred to as an effective amount.

The disclosed compounds, alone or in combination thereof or with any another therapeutically active agent, can be designed and utilized to exert a dual and possibly synergistic activity when in combination thereof or with any another therapeutically active agent.

According to an aspect of some embodiments of the present invention, there is provided a use of one or more from the disclosed compound I to IV, or a compound disclosed in Table 1, according to an embodiment thereof, or the disclosed pharmaceutical composition according to any embodiment thereof, for the manufacture of a medicament for treating a disease or disorder.

In some embodiments, the disease or disorder is associated with glycogen storage disease, or with disorder associated with an accumulation of PB, Adult polyglucosan body disease (APBD) as described above, e.g. GSD in any type thereof (e.g., type IV).

In some embodiments, the invention makes possible the treatment of forms of GSD, including, but not limited to, GSD-IV, -VI, IX, XI and cardiac glycogenosis due to AMP-activated protein kinase gamma subunit 2 deficiency. In some embodiments, the disclosed compounds may reduce pathogenic PB accumulation in the PB involving GSDs, GSD type IV (APBD and Andersen disease), GSD type VII (Tarui disease), and Lafora Disease (LD).

Further exemplary embodiments of compounds of Formulae I to IV, and Table 1 are described in the Examples section below.

Pharmaceutical Composition Comprising the Disclosed Compounds:

According to an aspect of embodiments of the invention there is provided a pharmaceutical composition comprising one or more compounds as described herein and a pharmaceutically acceptable carrier.

According to some embodiments of the invention, the composition is being packaged in a packaging material and identified in print, in or on the packaging material, for use in the treatment of a medical condition associated with any disease, medical condition, or disorder as described hereinthroughout.

According to an aspect of embodiments of the invention there is provided a method of treating a medical condition associated with any disease, medical condition, or disorder as described hereinthroughout in a subject in need thereof, the method comprising administering to the subject a therapeutically effective amount of the compound or composition as described herein.

In some embodiments, there is provided method of treating a glycogen storage disease by administering to a patient in need thereof a therapeutically effective amount of a pharmaceutical composition that comprises one or more from compounds of Formulae I to IV, and from Table 1.

In some embodiments, there is provided method of treating a glycogen storage disease by administering to a patient in need thereof a therapeutically effective amount of a pharmaceutical composition that comprises one or more from compounds A and B as described herein.

As used herein, the phrase "therapeutically effective amount" describes an amount of the compound being administered which will relieve to some extent one or more of the symptoms of the condition being treated.

The term "subject" (which is to be read to include "individual", "animal", "patient" or "mammal" where context permits) defines any subject, particularly a mammalian subject, for whom treatment is indicated.

In some embodiments, the subject is a human. In another embodiment, the subject is a human suffering from neurological disorder.

According to an aspect of embodiments of the invention there is provided a use of any one of the compounds as described herein as a medicament.

According to an aspect of embodiments of the invention there is provided a use of any one of the compounds as described herein in the manufacture of a medicament for treating a medical condition associated with any disease, medical condition, or disorder associated with an accumulation of PB, as described above.

The compounds described hereinabove may be administered or otherwise utilized either as is, or as a pharmaceutically acceptable salt, an enantiomer, a tautomer, a diastereomer, a protonated or non-protonated form, a solvate, a hydrate, or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the active compounds which are prepared with relatively nontoxic acids or bases, depending on the particular substituents found on the compounds described herein.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compound as described herein to be converted into either base or acid addition salts.

In some embodiments, the neutral forms of the compounds described herein are regenerated by contacting the salt with a base or acid and isolating the parent compounds in a conventional manner. The parent form of the compounds differs from the various salt forms in certain physical properties, such as solubility in polar solvents, but otherwise the salts are equivalent to the parent form of the compound for the purposes of the present invention.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

In some embodiments, the compounds described herein possess asymmetric carbon atoms (optical centers) or double bonds; the racemates, diastereomers, tautomers, geometric isomers and individual isomers are encompassed within the scope of the present invention.

As used herein and in the art, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

In some embodiments, the compounds described herein can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

In some embodiments, the "pharmaceutical composition" refers to a preparation of one or more of the compounds described herein (as active ingredient), or physiologically acceptable salts or prodrugs thereof, with other chemical components including, but not limited to, physiologically suitable carriers, excipients, lubricants, buffering agents, antibacterial agents, bulking agents (e.g., mannitol), antioxidants (e.g., ascorbic acid or sodium bisulfate), anti-inflammatory agents, anti-viral agents, chemotherapeutic agents, anti-histamines and other.

In some embodiments, the purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier", which may be interchangeably used, refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, PA, latest edition, which is incorporated herein by reference.

In some embodiments, pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage, as described and specified herein, may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

In some embodiments, the pharmaceutical composition may be formulated for administration in either one or more of routes depending on whether local or systemic treatment or administration is of choice, and on the area to be treated. As further described herein throughout, administration may be done orally, dentally, by inhalation, or parenterally, for example by intravenous drip or intraperitoneal, subcutaneous, intramuscular or intravenous injection, or topically (including ophtalmically, vaginally, rectally, intranasally).

Formulations for topical and/or dental administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration may include powders or granules, suspensions, dental compositions, or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and anti-histamine.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some embodiments, the method comprises administering to the subject a pharmaceutically effective amount of one or more of the herein disclosed compounds or compositions (e.g., compounds having one of the general "Formulae I or II" described herein above, in any embodiment thereof.

In some embodiments, the method may further comprise administrating an additional drug intended to treat an antimicrobial infection.

It will be recognized that these embodiments are susceptible to various modifications and alternative forms well known to those of skill in the art.

Screening Method

According to an aspect of some embodiments of the present invention, there is provided a method for detecting PB in cells. In some embodiments, the cells are human cells e.g., fibroblast cells.

In some embodiments, the method comprises a step of computational screening of libraries of compounds.

In some embodiments, the method comprises detecting reduction of PB exerted by one or more selected compound (e.g., a small molecule).

It will be appreciated that by virtue of enabling computational screening of libraries of compounds having essentially any of various chemical, biological and/or physical characteristics, the method enables identification of a compound capable of displaying optimal in-vivo pharmacokinetics, optimally low immunogenicity, and optimal effectiveness relative to all prior art compounds capable of decreasing PB cellular content, for example, by correcting impaired enzymatic activity associated with glycogen storage disease e.g., glycogen synthase or, glycogen branching enzyme.

In some embodiments, the method comprises biochemically qualifying the capacity of the compound to decrease PB cellular content.

In some embodiments, the biochemically qualifying comprises subjecting cells to Periodic Acid-Schiff (PAS) staining to provide PAS stained cells. In some embodiments, the method further comprises washing the sample to remove unreacted Schiff's reagents followed by detecting a signal (e.g., light fluorescing) derived from the PAS stained sample at a defined wavelength.

Further embodiments of the disclosed method are provided in the Examples section below.

Definitions

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range;

e.g., "21-100", is stated herein, it implies that the group, in this case the alkyl group, may contain 21 carbon atoms, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons.

The alkyl can be substituted or unsubstituted, as defined herein

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "haloalkoxy" describes an alkoxy group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" or "sulfonate" group describes an —S(=O)$_2$—R' group, where Rx is as defined herein.

A "carbamyl" or "carbamate" group describes an —OC(=O)—NR'R" group, where R' is as defined herein and R" is as defined for R'.

A "nitro" group refers to a —NO$_2$ group.

A "cyano" or "nitrile" group refers to a —C≡N group.

As used herein, the term "azide" refers to a —N$_3$ group.

The term "sulfonamide" refers to a —S(=O)$_2$—NR'R" group, with R' and R" as defined herein.

The term "phosphonyl" or "phosphonate" describes an —O—P(=O)(OR')$_2$ group, with R' as defined hereinabove.

The term "phosphinyl" describes a —PR'R" group, with R' and R" as defined hereinabove.

The term "alkaryl" describes an alkyl, as defined herein, which substituted by an aryl, as described herein. An exemplary alkaryl is benzyl.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

General

As used herein the term "about" refers to ±10%.

The terms "comprises", "comprising", "includes", "including", "having" and their conjugates mean "including but not limited to".

The term "consisting of means" including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

Reference is now made to the following examples, which together with the above descriptions illustrate some embodiments of the invention in a non-limiting fashion.

Example 1

Screening Assays

High Content (Image-Based) Screening Assay

All the steps of the assay were performed automatically using a Freedom Evo 150 liquid handling robot (Tecan). APBD patient-derived fibroblasts were seeded at a density of 800 cells/well in DMEM (Gibco) supplemented with 1 mM sodium pyruvate (Gibco), 1% antibiotics (Biological Industries, Israel) and 5% fetal bovine serum (Hyclone) into 384 well microclear plates (Greiner). The plates were transferred by the robotic arm (RoMa) into an automated incubator (Liconic), integrated with the robotic system, where they were incubated at 37° C. with 5% $CO_2$. Following 24 h incubation, the medium was replaced by the robot using medium supplemented with 10 µM of each screened compound (0.1% DMSO final concentration, all prepared by the robot). The screened compounds were part of the Diverset CL collection purchased from ChemBridge (10,084 out of 50,000 molecules).

Next, these cells were cultured for another 24 h in the automated incubator, and, using the robot, washed them with PBS (Biological Industries, Israel), the cells were fixed with 4% paraformaldehyde (PFA), washed again with PBS, neutralized the previously added PFA by ammonium chloride (Sigma Aldrich), washed with PBS, permeabilized with 0.1% Triton X-100 (Sigma Aldrich), and washed again with PBS.

Following this, a robot was used to treat the fixed cells with 0.5 g/dl diastase (or amylase, Sigma Aldrich) for 5 minutes at 37° C. in the automated incubator, wash with PBS, stained with PAS (Merck), Hoechst 33342 (Sigma Aldrich) and Cell Mask Deep Red (Molecular Probes) and wash with PBS. Images of stained cells were then acquired by the IN Cell Analyzer 2000 (GE Healthcare) and analyzed using the IN Cell Investigator (GE Healthcare) applying an algorithm that quantified the PAS signal within each Cell Mask stained cell.

Image Analysis and Hit Determination

Images were segmented based on the Cell Mask signal which was linked with the segmentation of the nuclei, employing an empirically established sensitivity and kernel size for allowing the best segmentation. Once these nucleus-cytoplasm complex objects were selected, the software calculated the number of these objects (cell number) as well as the intensity of the PAS signal within each of them. All the assay parameters (including the acquisition exposure times, objective, and the analysis parameters) were kept constant throughout the whole screening campaign for allowing comparison of signals obtained from different batches of assay within the campaign.

Dose-Response Curves

The assay was performed as mentioned above, but with compound concentrations of 1, 5, 10, and 50 µM, instead of a constant concentration of 10 µM.

In Vitro GS Activity Assay

The reaction was carried out in 96-well plates containing 50 µl of reaction volume (50 mM Tris, pH8, 20 mM EDTA, 25 mM KF, 2 mg/ml glycogen, 10 mM Glucose-6-Phosphate, 1.65 mM UDP[14C]glucose and 100 mM UDP-glucose). To test the inhibitory effect of the hits, each one was included in the reaction at a final concentration of 50 µM. The reaction was initiated with the addition of 20 nM recombinant human GS1, followed by incubation at 37° C. for 30 min. The reaction was then stopped with the addition of $100_11.1$ cold 100% ethanol, and the total suspension was transferred into a 96-well filter plate. Vacuum was applied to remove the ethanol. Five washing steps with 150 µl of cold 66% ethanol then fully removed any non-incorporated UDP [14C]glucose, while the labelled glycogen stayed on the well filters. The plate was dried at 37° C. incubator for 30 min. 50 µl of scintillation fluid was added to each well and the plate was read for 14C signal on Microplate scintillation and luminescence counter Top Count (Perkin Elmer).

Ligand Profiling

In order to identify potential bio-targets (required due to the phenotypic nature of the screen), active compounds were screened against the PharmaDB pharmacophore database using the Ligand Profile protocol, implemented in Discovery Studio (DS) version 4.1. PharmaDB is a database of pharmacophores created from the sc-PDB protein data bank (http://bioinfo-pharma.u-strasbg.fr/scPDB/). It consists of over 132,000 pharmacophore models, generated from 283 binding sites from 3678 unique proteins and 5608 unique ligands. Many protein targets are represented by multiple pharmacophores with shape constrains generated from excluded volumes.

Clustering of Hits and Known Drugs

Hierarchical clustering was performed based on dendritic fingerprints with merging distance of 0.99 using Canvas v. 2.7. The Kelley criterion was used to obtain an optimal number of clusters. The total number of clusters that was obtained in our analysis was five. However, four of these clusters included only 1-2 known drugs and only one cluster was informative and included all the hits together with 21 of the 27 drugs found to interact with putative hit binding proteins which also bind carbohydrate derivatives.

Similarity Analysis

Hit similarity to drugs was calculated using the Find Similar Molecules by Fingerprint protocol implemented in DS using MDL public key, ECFP 4, ECFP 6, FCFC 2, FCFP 4 fingerprints and requiring a minimum similarity score of 0.5.

A High Throughput Assay for Detecting PB

Since in APBD neurons undergo degeneration due to PB accumulation, a small molecule library was screened in order to find compounds capable of decreasing PB cellular content. For that purpose, an assay based on PAS staining of PB in fibroblasts derived from an APBD patient's skin was developed.

A further work was conducted to demonstrate that, unlike skin fibroblasts derived from healthy individuals, skin fibroblasts from APBD patients show detectable PB.

Figure 1A:
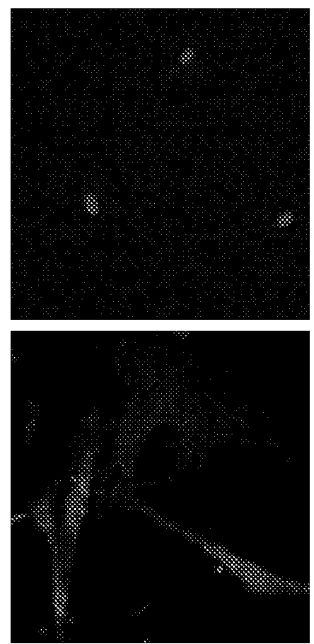
FIGS. 1A-C present High Throughput Screening for compounds able to reduce polyglucosan body (PB): Skin fibroblasts from an Adult Polyglucosan Body Disease (APBD) (left) and control (right) subjects were formaldehyde-fixed, amylase digested, stained with Hoechst (blue) and PAS (red), and then imaged by the InCell 2000 High Content Analysis system (FIG. 1A); A representative image of cells showing the different stains employed (from left to right, as indicated in the figure, nuclear, Periodic acid/Schiff base (PAS), Cell Mask and a merged image) (FIG. 1B); Adult polyglucosan body disease (APBD) patient derived fibroblasts were cultured for 24 h in DMEM (with 5% FBS) and then 10,084 different compounds from the DiverSet CL library (Chembridge) were added to each different well at a concentration of 10 μM. Following an additional 24 h incubation, the cells were fixed, the fixative was neutralized, and the cells were then permeabilized, treated with diastase and stained with Hoechst 33342, Cell Mask Deep Red and PAS. Images were then acquired and analyzed (FIG. 1C upper left panel). Each well mean of cell area (based on Cell Mask Deep Red staining) was normalized by z-scores according to the populational mean of all the compounds. Compounds showing a toxic effect were discarded by keeping only those showing a z-score higher than −1.5 for their normalized cell area mean and more than 300 cells per well (FIG. 1C, upper right panel). Once this selection was made, the hits were selected based on the normalized polyglucosans (PG) mean intensity. Those compounds inducing a well-based PG mean intensity below −1.2 z-score were selected as hits. Thus, from 10,084 compounds screened, 85 were selected as hits. These selected compounds were subjected to the same assay once again employing concentrations of 0, 1, 5, 10 and 50 μM. This dose response experiments narrowed down the 85 selected hits to 11 in which a concentration dependent decrease of cell associated PG mean intensity has been demonstrated (FIG. 1C lower right panel).

Capitalizing on the observation that PGs are resistant, up to certain ceiling concentration and exposure time, to the glycogen digesting enzyme amylase, to operationally define PG, it was administered, post paraformaldehyde fixation, amylase to unaffected and APBD fibroblasts in order to digest soluble glycogen, sparing the relatively amylase-resistant PG, which consequently could be detected. As the results (FIG. 1A) show, amylase resistant staining, and therefore PG and PB, were uniquely observed in APBD and not control fibroblasts.

In additional exemplary procedures, both amylase's cell exposure time and concentration were optimized to achieve the maximal extent of glycogen degradation which spares PG. The chosen conditions following this optimization step were 0.5 g diastase/dl and 5 minutes digestion at 37° C.

In addition, several other aspects of the assay were optimized establishing also the exposure time to compounds (1 day), the medium composition (5% FCS in DMEM), the employed fibroblasts passage (#11), the fixation technique (4% PFA for 10 minutes followed by ammonium chloride neutralization), the permeabilization (5 minutes by 0.1% Triton X-100), additional staining (Hoechst 33342 for nuclei and CellMask Deep Red for cytoplasm reference), plate type (384 well microplates) and cell density (800 fibroblasts/well.

Establishing Criteria for the Identification of PB-Reducing Compounds

Once optimized, the assay was used to screen 10,084 compounds from the Diverset CL collection (ChemBrige) by exposing APBD patient derived fibroblasts to these molecules at a 10 µM concentration. Images were analyzed by performing segmentation of cells based on the Cell Mask Deep Red staining and using the Hoescht 33342 staining to determine if two cells were segmented together as a unique entity (in case they were too adjacent to allow segregation by the software). This feature allows reducing possible under segmentation.

Figure 1B:
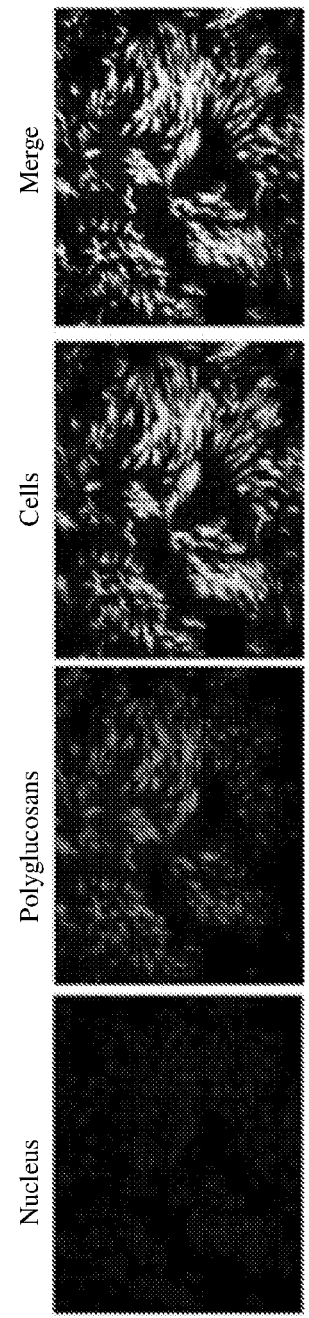
Figure 1C:
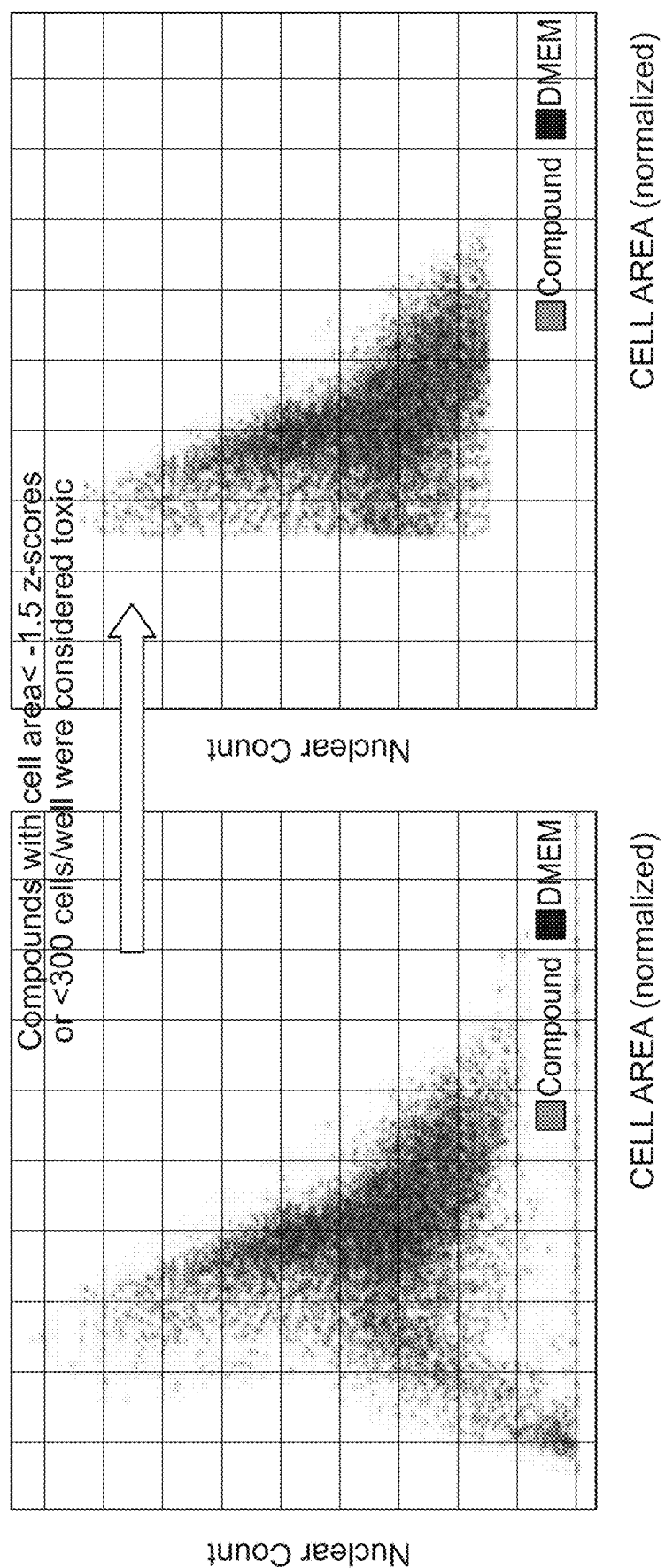

A representative image of the obtained staining is depicted in FIG. 1B. FIG. 1C shows the compiled data points of the screening, illustrating the approach employed for selecting hits. Briefly, once the cell area was established based on the Cell Mask Deep Red signal, the PAS signal in each of the cells was determined (corresponding to cell associated PB mean intensity). Cell area data averaged at the well level were normalized according to the overall well population in the entire screening campaign using the z-score method.

Based on previous image training, only those wells treated with compounds whose induced normalized cell area population mean above −1.5 z-score and showed at least 300 surviving cells (i.e. stained nuclei linked to Cell Mask Deep Red stained object) per well were considered for further analysis. The discarded data was presumably associated with cells affected by toxic compounds. In the remaining data, the measured population mean PB intensity was normalized. Based on a series of images used for training, compounds were considered as positive only where following treatment the normalized PB mean intensity was at least under −1.2 z-score of the scale. Following this approach, 85 potential hits out of the 10,084 screened compounds were selected (0.84%). FIG. 1C shows that these selected molecules caused a decrease in PB mean intensity without any evidence of toxicity (no cell area or cell count reduction).

Discovery of Drug Candidates for Treating PB-Involving GSD

Figure 2A:
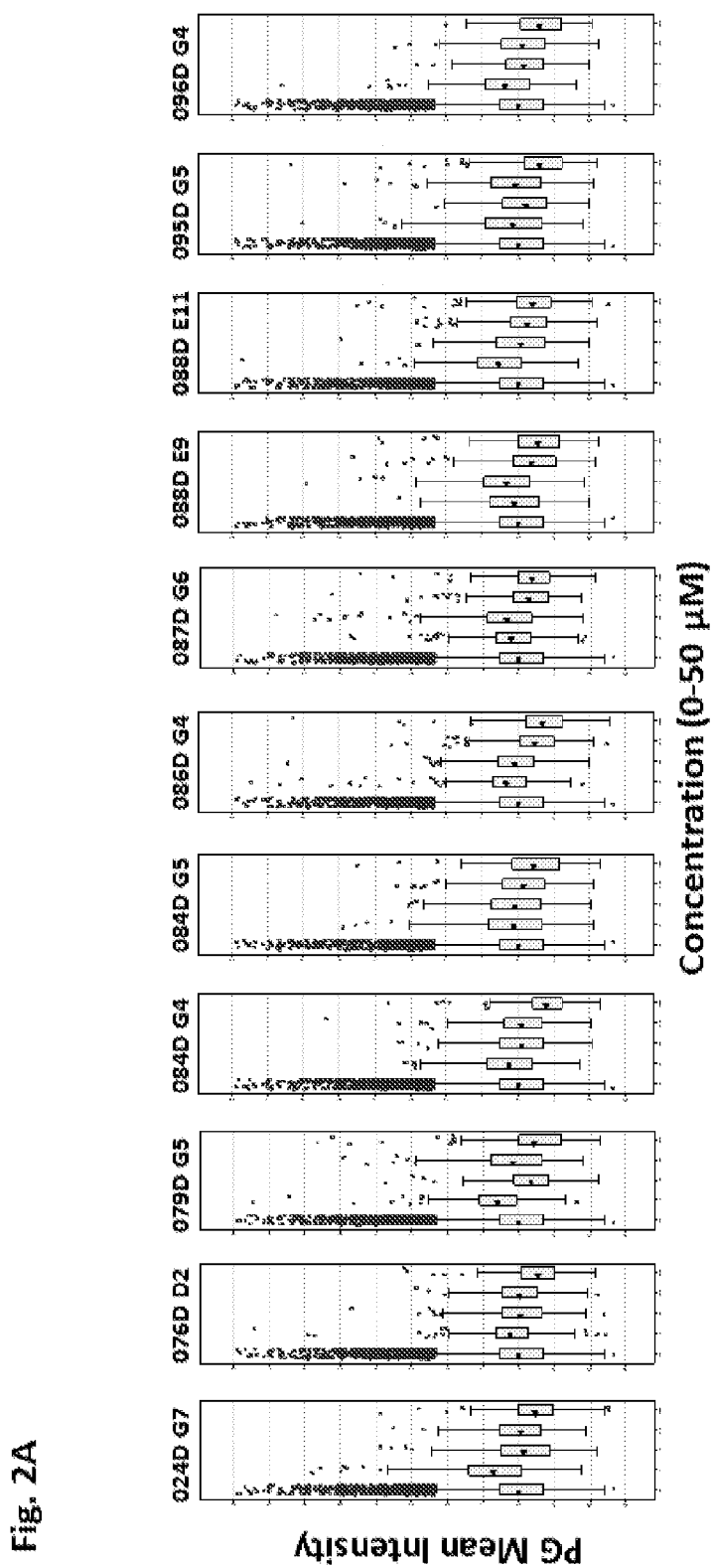
Figure 2B:
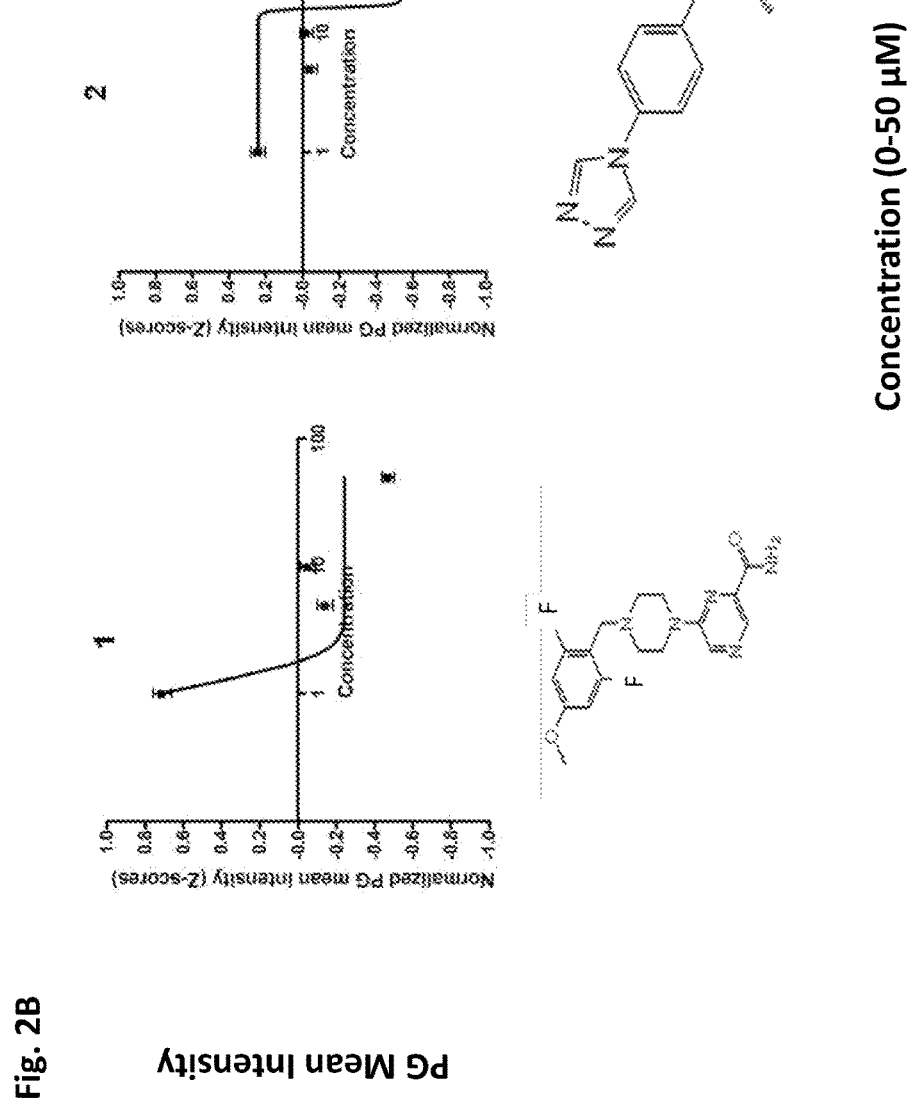

Following this primary screening, it was decided to establish dose response curves for the 85 hits for further validation. For this purpose, the same assay was performed, except in compound concentrations of 0, 1, 5, 10, and 50 µM. FIGS. 2 (A & B) show the molecular formulae and dose response curves of 11 compounds selected as best dose-responders from the 85 hits. These 11 compounds reduce cell associated PB mean intensity in a hormetic, or biphasic dose dependent manner (FIG. 2A) up to 1 µM concentration, PB mean intensity increases slightly, possibly as an adaptive response to maintain homeostasis, and then, at concentrations greater than 1 µM, dose dependent decrease is observed.

Figure 3A:
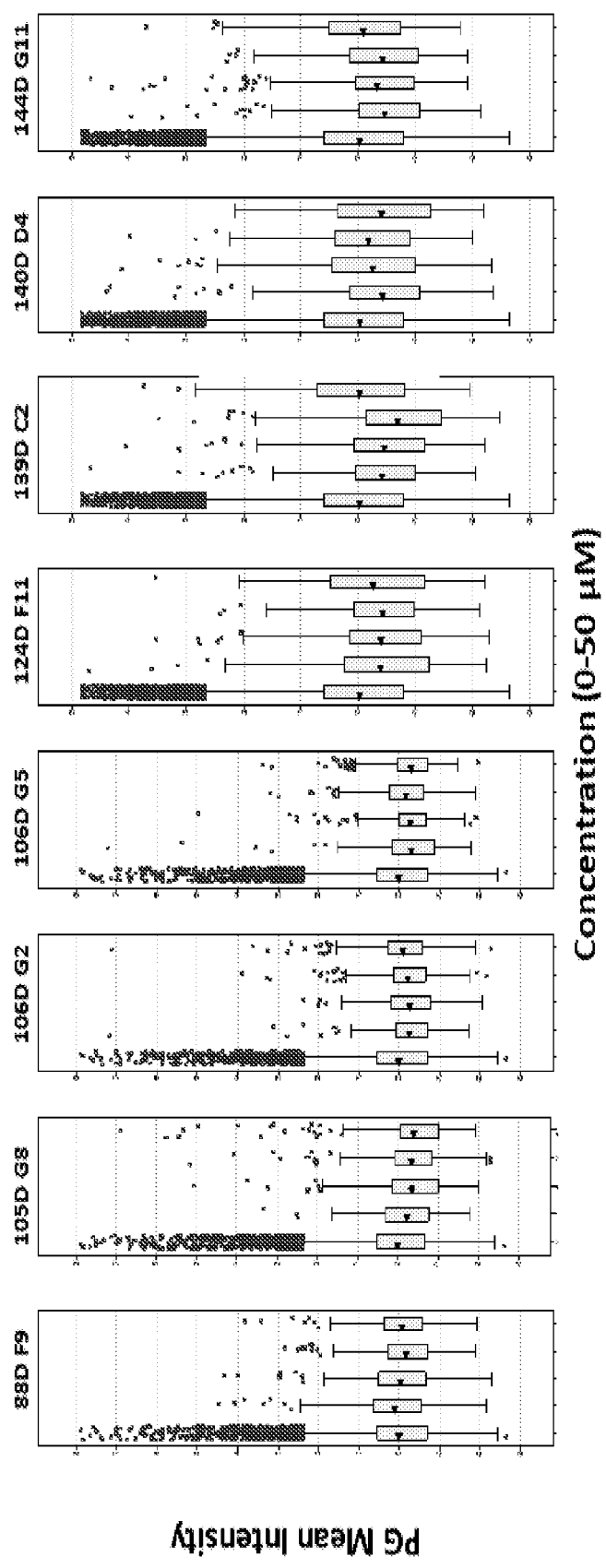
FIGS. 3A-B present none dose-responding PB reducing hits.
Figure 3B:
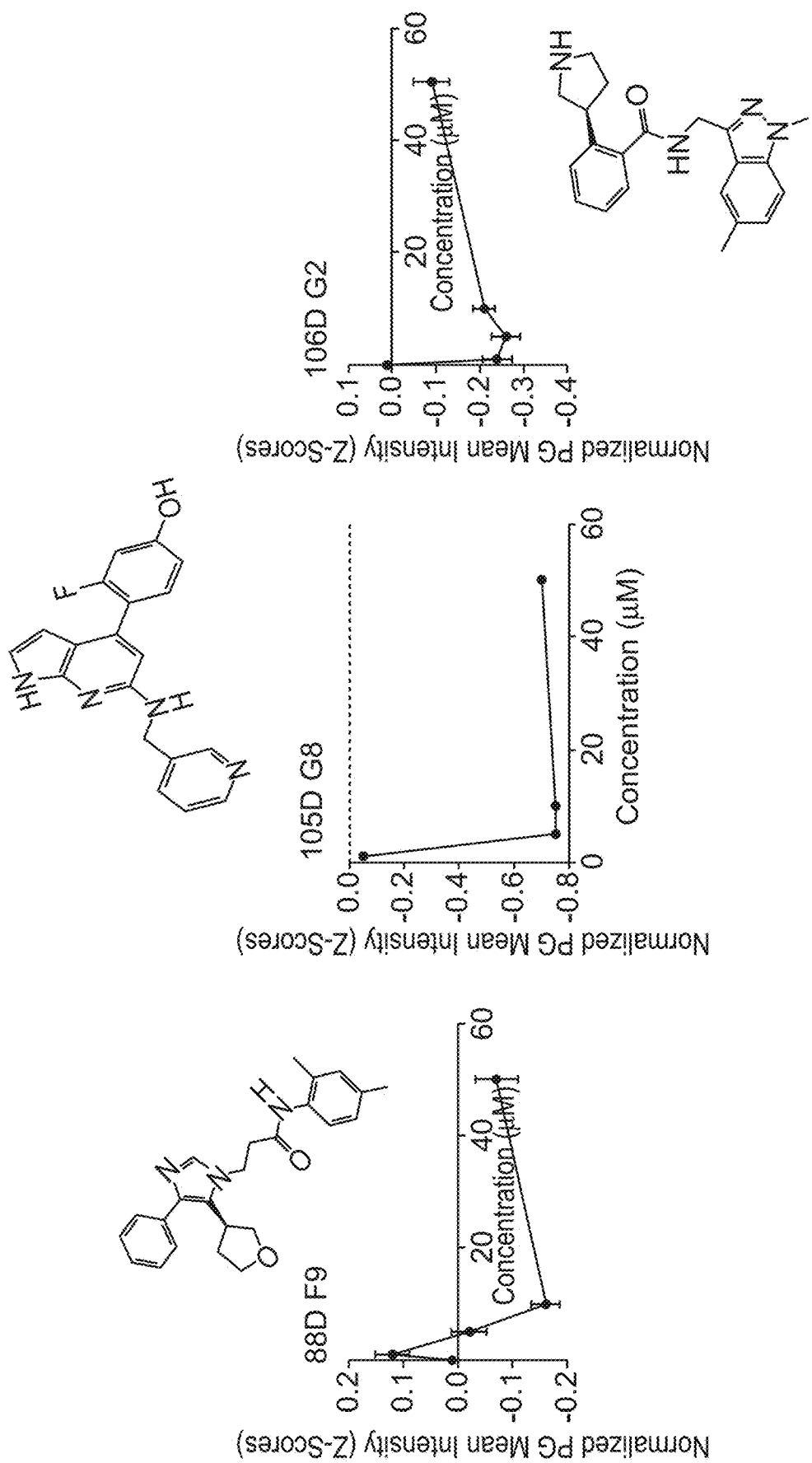

While dose responsiveness is an accepted hit validation criterion, in the current analysis also 8 compounds were included (FIGS. 3 A & B) which were effective in reproducibly lowering PB levels, though by a monophasic, apparently non dose-responsive, manner.

It is assumed that the dynamic range of the concentration-dependent PB reduction effect of these compounds in fibroblasts is too narrow to be detected by the assay. These 8 hits were termed "monophasic" hits.

The Effect of PB-Reducing Hits on GS Activity

Once PB-reducing hits were discovered, a possible mechanism by which these hits might lower PB levels was explored. While instigated by malconstructed glycogen, PB are a more complex entity involving regulatory and scaffolding proteins. Therefore control of PB size may be mediated by several enzymes, able to generate PG (e.g., GS and protein phosphatase-1 (PP1)), shape them (e.g. GBE), or degrade them (e.g., glycogen debranching enzyme (GDE) and GP). However, the most straight forward PG-controlling enzyme with well-studied regulatory mechanism is GS. Therefore, an initial in vitro assay to test hit effect on GS activity was performed.

Figure 4A:
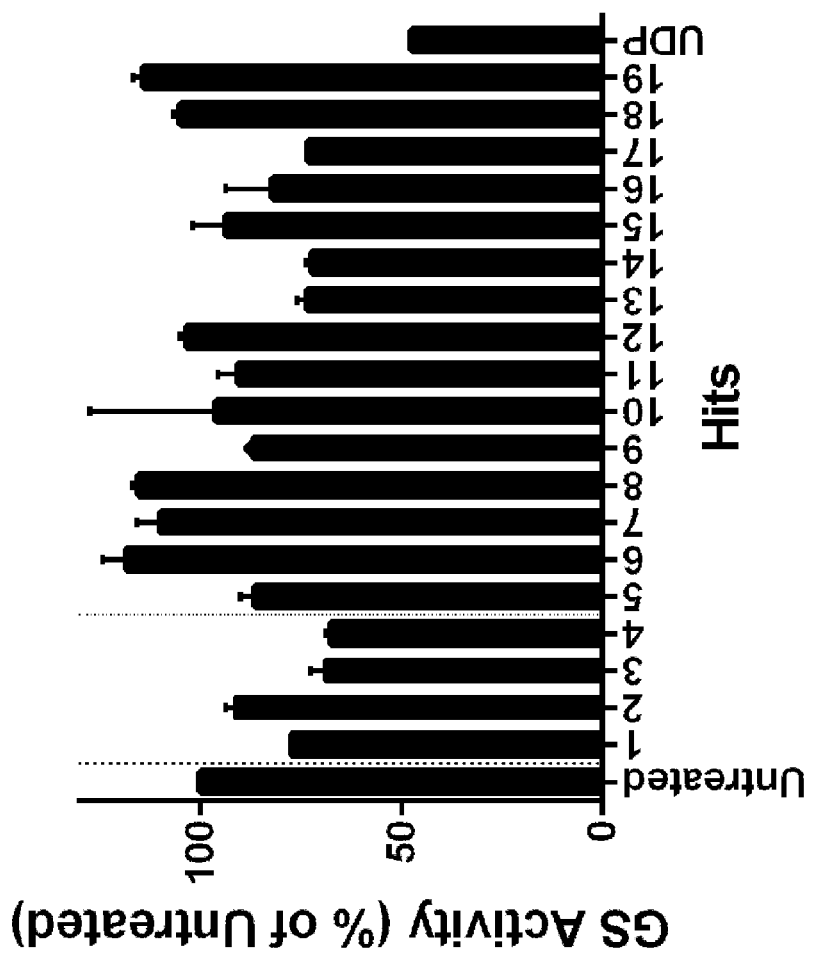

As can be seen in FIG. 4A, it was found that at a concentration of 50 µM, 13 out of the 19 hits significantly reduce GS activity by over 30%. This may suggest that the inhibitory effect observed in PB reduction for most hits in cells is due to direct inhibition of the GS enzyme alone, or in combination with other modes of action, such as PP1 inhibition.

Computational Prediction of Possible Modes of Action of the Hits

To gain some preliminary insight into possible modes of action by which the identified hits have lowered PB levels, computational analysis was conducted. It was first confirmed that out of the 19 biphasic and monophasic hits discovered (represented by 36 molecular entities where certain hits were represented by multiple protonation and tautomeric states) only two were predicted to be promiscuous binders (based on a list of 28 fragments known to characterize promiscuous binders). Then the compounds were profiled against an extensive set of pharmacophore models derived from unique protein binding sites and ligands as detailed in Materials and Methods. This profiling procedure predicted protein sites which might interact with the hits. Using the UniHI software, an interactome map of these proteins was generated (see FIG. 5A). From this interactome map, proteins which are drug targets were identified.

Next, gene ontology tools were used to filter out from the drug targets the proteins predicted to bind carbohydrate derivatives (FIG. 5B) under the assumption that these proteins will be more relevant to PG metabolism. UniHI has identified 27 drugs which interact with proteins which also bind carbohydrate derivatives. These 27 drugs were clustered together with the identified 19 (biphasic and monophasic) hits. The largest cluster included 21 drugs and all hits (including their possible protonation (pH 7) and tautomeric states). About half of these drugs (9 out of 21, Drug Bank (https://www.drugbank.ca/) identifiers DB04012, DB01712, DB08520, DB02888, DB01723, DB00877, DB00337, DB00864, DB03621) interact with the GS inhibitor protein phosphatase 1 (PP1), six directly (DB04012, DB08520, DB02888, DB00877, DB00864, DB03621) and three (DB01712, DB01723, DB00337) via the PP1 complexed FKBP1A protein. When the hits were ranked according to their similarity to these 9 PP1 interacting drugs, only four (out of the 36 hit entities) met the minimum similarity requirement. Three of these four hits are above the median of GS inhibition potency (see Tables 1 and 2). This analysis thus suggests inhibition of PP1-mediated GS activation as a possible PB-lowering mechanism common to some of the hits discovered.

To confirm that the measured output is the result of a true reduction in PB content and not of cell shrinkage (possibly caused by cell toxicity), the PB-detecting PAS assay was optimized by incorporating a third staining for cytoplasmic reference. This cytoplasmic reference allowed to associate the measured PB mean intensity to a given cell and determine whether that cell area was significantly affected by the tested compound. This approach further allowed to confirm that the selected output reflects a true effect of the compound on the PB content, filtering out toxic compounds.

The distribution of hits among the plates (data not shown) was sufficiently homogeneous to suggest that the results cannot be attributed to an artifact resulting from an uneven staining of the plates. Only 11 biphasic hits and 8 monophasic hits, with a stable effect, were selected for analysis. Typical dose-responding hit rates from experimental HTS can range between 0.01% and 0.14%, in high accordance with the hits rate observed for the 11 biphasically dose-responding candidates, which constitute 0.11% of the total screened molecules.

As APBD is a genetic condition, the GBE mutations implicated in it should produce a phenotype not only in neurons but also in cells not directly involved in the pathogenicity such as fibroblasts, which are easier to obtain and culture than neurons.

The results obtained prior to the assay development (FIG. 1A) showed that APBD fibroblasts have a higher PB content than fibroblasts derived from unaffected subjects. Of note that, as opposed to APBD fibroblasts (both patient and mouse-derived), fibroblast cell lines from Lafora Disease (LD) patients or mice do not form PB per se. A likely explanation for this difference is that the replicating cell lines in LD, derived from adolescent patients as opposed to middle-aged to old ones in APBD, simply do not have the timespan required for full-fledged PB to materialize.

Figure 5A:
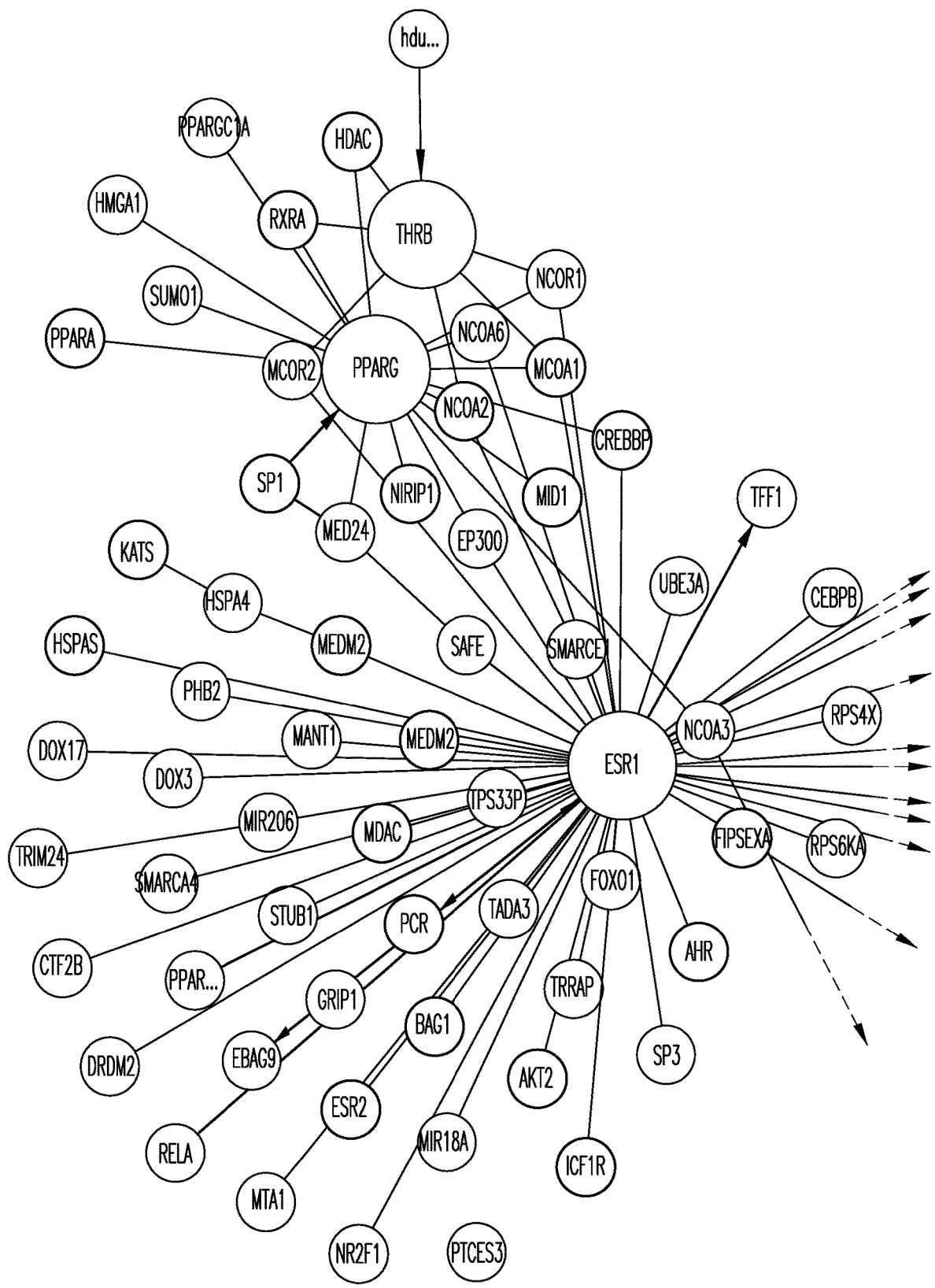
FIGS. 5A-B show protein targets of the hits.
Figure 5B:
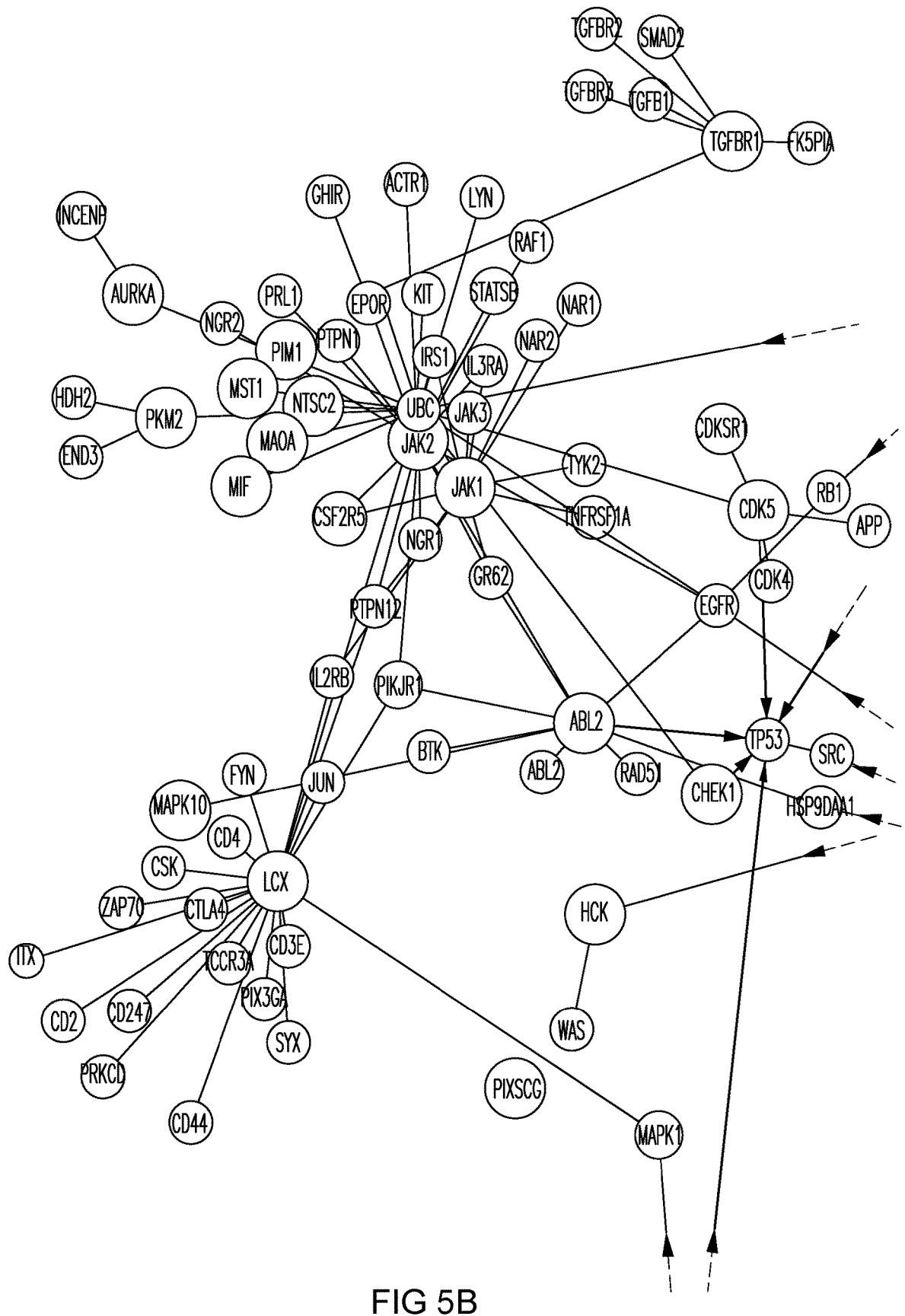

The screening assay which was employed capitalized on phenotypic selection of hits based on a single readout (cell associated PG mean intensity), which can be caused by multiple factors, as suggested by the complexity of interactions among candidate hit interacting proteins (FIGS. 5A-B). Thus the observed compound effect in the analyzed images does not necessarily reveal whether the drug candidate is acting as a GS inhibitor, GBE stabilizer or by somehow promoting PG degradation. Nevertheless, the data (FIG. 4A) suggest that a possible mode of action of 70% of the hits (13 out of 19) is, at least in part, inhibition of GS activity, which stands to reason given that GS is the only enzyme capable of forming the al-4 interglucosidic bonds that constitute PG. These data are corroborated by the computational analysis according to which half of the drugs clustered with all the hits interact with the GS activator PP1.

The GS inhibition mode of action has already been demonstrated for rapamycin, a drug used for treating tuberous sclerosis, which, while being a well-established autophagy inducer, actually suppressed PB levels not by autophagic clearance, but by inhibiting GS activity. Rapamycin reduced PG in APBD modeling neurons and glycogen in mice modeling the GSD Pompe Disease. However its toxic effects in APBD mice (our unpublished data) disqualified it for further development. Since PB is the pathogenic factor in PB-involving GSDs, the present findings that most PB reducing compounds are also mild GS inhibitors call for a GSD therapeutic strategy based on mild inhibition of GS activity, also expected to be less cytotoxic.

Of note that rapamycin, in addition to its pleiotropic effects, is a robust, rather than mild, inhibitor of GS activity (which it reduced by 70%).

In one of the LB-associated GSDs, LD, it has been shown that a mere 30% reduction of GS activity, through knockout of the PP1 subunit (Ptg) that targets the phosphatase to GS, rescues the disease's animal model. The present drug candidates achieve this threshold of GS activity reduction (FIG. 4A) thus constitute a promising therapeutic strategy. On the other hand, PB reducing hits which did not inhibit GS (and even upregulated its activity, FIG. 4A) point to the multifaceted regulation of PB levels, amenable not only to manipulation of their synthesis (by GS), but also of their degradation and shaping.

Thus the data suggest that the hits discovered are indeed germane to net polyglucosan formation, either directly or indirectly.

Finding an inhibitory effect of most hits on GS activity (FIG. 4A) and the computational prediction that 3 of the GS inhibiting hits might also interact with PP1 (see Table 2 in FIG. 4B) are especially important in view of the innate non-specificity of some screening assays, revealed e.g., by the so-called pan-assay interference compounds (PAINS). Providing evidence in support of an expected and relevant mode of action, as GS inhibition is for lowering PB levels, should thus be exercised in all HTSs in order to prevent the "discovery" of false positive hits which may waste time and resources in futile research.

Example 2

Summary of ADMET

In order to implement in the future our discovered drug candidates in the clinic, they will have to meet certain ADMET (Absorption, Distribution, Metabolism, Excretion, and Toxicity) criteria, which is the common practice for many de novo designed drugs. Therefore, a thorough ADMET analysis was performed, based on three independent tools as described below. This analysis was able to narrow down our list of 11 dose responsive and 8 non-dose responsive compounds to only 4 which were pharmacologically preferred. Of the five compounds prioritized based on a single ADME tool (qik_prop (ADME prediction) in the program Maestro11.2), only one (N-[3-(2,7-diazaspiro[4.5]dec-2-ylcarbonyl)-2-methylphenyl]-2-furamide) met the strict ADMET criteria, emphasizing the importance of cross comparing several ADMET prediction tools.

The results from 3 different programs are described:
1. QiqProp (by Schrodinger)
2. SwissADME (the program of Marvin/ChemAxon)
admetSAR @ LMMR FIG. 6 present Table 3 summarizing the common and the difference between the programs.

Results

UDP-1 from the beginning due to many problematic values.

QikProp

FIG. 7 presents Table 4 summarizing the results for descriptors with exceptions.

SwissADME

FIG. 8 presents Table 5 summarizing the results.

AdmetSAR

FIG. 9A presents Table 6 summarizing the results.

Summary

FIG. 9B presents Table 7 summarizing the preferred candidates, assuming the candidates have with less than 4 exceptions.

Example 3

Ex and In Vivo Results

In order to implement the discovered drug candidates in the clinic, they should meet certain ADMET (Absorption, Distribution, Metabolism, Excretion, and Toxicity) criteria, which is the common practice for many de novo designed drugs.

Therefore, a thorough ADMET analysis was performed, based on three independent tools, as described above.

This analysis could narrow down the list of 11 dose responsive and 8 non-dose responsive compounds to only 4 which were pharmacologically preferred.

It is noteworthy that of the five compounds prioritized based on a single ADME tool (qik_prop (ADME prediction) in the program Maestro11.2), only one (N-[3-(2,7-diazaspiro[4.5]dec-2-ylcarbonyl)-2-methylphenyl]-2-furamide) met the strict ADMET criteria, emphasizing the importance of cross comparing several ADMET prediction tools.

Next, the multi-parametric phenotyping of this compound (N-[3-(2,7-diazaspiro[4.5]dec-2-ylcarbonyl)-2-methylphenyl]-2-furamide) and three more which met the ADMET criteria-N-(2-methoxyethyl)-6-methyl-N-[(3-methyl-2-thienyl)methyl]-2-oxo-1,2-dihydropyridine-4-carboxamide (compound A), 5-methyl-1-[4-(4H-1,2,4-triazol-4-yl)phenyl]pyrrolidin-2-one, and 4-tert-butyl-2-(4H-1,2,4-triazol-4-yl)phenol were continued. NB, in terms of reducing polyglucosan body accumulation, which is the end point and most relevant criterion for a putative polyglucosan reducing drug, all these compounds qualify.

However, it was decided to focus on compounds with a realistic prospect of eventually becoming approved drugs, rather than on compounds which were predicted to be superior by previous criteria of similarity to protein phosphatase 1 (PP1) interactors or glycogen synthase (GYS) inhibition competence. This is a major step in the process for hit to lead optimization.

Next, the multi-parametric analysis of compound A, one of the compounds tested in the Gbe$^{Y329S/Y329S}$ mouse model for APBD was completed. The results are presented in FIG. 10. The different cell features in APBD fibroblasts of several patients were ordered according to the extent of their deviation from the same features in healthy fibroblasts.

As can be seen in FIG. 10 (upper panel), compound A has mostly affected nuclear and mitochondrial membrane potential (TMRE) parameters, which were among the features most affected by the disease phenotype. As expected, this effect was more pronounced when compound A treated APBD fibroblasts were compared to untreated HC fibroblasts (a comparison more relevant to the clinical settings): Compound A treatment on its own probably has similar effects on both affected and healthy cells and therefore probably brings the two phenotypes closer together, partially masking the effect of this compound v healthy control (HC).

It was discovered that compound A has a therapeutic value at the animal level (as shown in the in vivo results) and that of all features different between HC and APBD cells, nucleus and mitochondrial membrane potential (MMP) were mostly affected by compound A. These discoveries suggest that manipulation of these features, perhaps by established effectors, might be efficacious in the clinic at least as co-therapy with other agents.

The results shown in the lower panel of FIG. 10 reveal that for most features, compound A had caused the same trend (increase or decrease) in both affected and healthy cells. In general, in the affected cells, compound A has brought forth a change in the preferred direction (i.e., closer to the HC phenotype) in the features most different between APBD and HC, but, conversely, in the undesirable direction (further away from the HC phenotype) in features less dissimilar between APBD and HC.

Without being bound by any particular theory, it is speculated that this phenomenon might reflect cellular overcompensation to the action of compound A on features less affected by the diseased state. The specific features most affected by compound A are nuclear intensity, which is increased, and area of respiring (TMRE labeled) mitochondria which is decreased. The apparent beneficiary effects of compound A on the APBD cell phenotype is being elucidated in the mechanism of action studies as part of the hit to lead optimization process.

In Vivo Results

Compound A and (1S*,6R*)-9-{[4-(methoxymethyl)-5-methylisoxazol-3-yl]carbonyl}-3-methyl-3,9-diazabicyclo[4.2.1]nonan-4-one (compound B) were tested for their efficacy to correct motor disease phenotypes in our APBD cell model. This study was conducted in compounds A and B according to the schemes described in Tables 8 and 9, respectively.

All compounds were injected at the pre-determined maximal concentration of 250 mg/kg which showed null side effects in wild type animals. As vehicle control, 0.1% DMSO was used. It is noteworthy that, in order to have a statistically significant number of animals, compound A was tested in male mice and compound B in female mice (no mixed cages were allowed).

APBD is an autosomal disease with no gender related symptoms and it was presumed that this experimental design is optimal. The mode of delivery of the compounds was intravenous (IV) injection for the first month, followed by subcutaneous injection due to lack of injection space and scaring in animal tails.

This injection regime was selected for two reasons: a. The plasma concentration is supposed to be higher and increase sooner in IV as compared to intraperitoneal (IP) injection. Therefore, everything else (BBB crossing etc.) being equal, higher compound concentrations are supposed to reach the brain sooner in IV as compared to IP injection and also their concentrations should be higher. b. The risk of incidental injection to the bowel exists for IP injections and not for IV injections.

Tables 8 and 9 describe the study design for compounds A and B. both compounds were tested at the age of 4 months, two months prior to disease onset, in order to assess possible prophylactic effects, and at the age of 6 months, at disease onset, in order to assess corrective effects.

TABLE 8

Number of animals used for testing Compound A (males)

| | Pre-onset treatment | Vehicle control | Post-onset treatment |
|---|---|---|---|
| From the age of 4 months | 7 | 6 | — |
| From the age of 6 months | — | 6 | 6 |

TABLE 9

Number of animals used for testing Compound B (females)

|  | Pre-onset treatment | Vehicle control | Post-onset treatment |
|---|---|---|---|
| From the age of 4 months | 9 | 8 | — |
| From the age of 6 months | — | 8 | 9 |

Example 4

The Influence of Compounds a and B on Motor Parameters in APBD Modeling Mice

The effect of compounds A and B on various motor parameters was tested every two weeks. The results are shown in herein.

Briefly, the data show that of all parameters tested the most pronounced ameliorating effect was on the extension reflex (FIG. 12A) and grip strength (FIGS. 13A-D). Compound (comp.) A, administered after before disease onset at 4 months of age, also seems to improve gait regularity tested by the ink tests (FIG. 16A).

Administered after disease onset, at the age of 6 months, compound A also improves the uniformity of step alteration (from one paw to the other, FIG. 17B). These effects can also be observed by the amelioration of limping in the films attached.

Compound A seems to ameliorate extension reflex, grip strength and gait, and compound B seems to ameliorate grip strength. Moreover, the ameliorating effects of compound A on extension reflex FIG. 12A) and gait regularity FIG. 16A) take place before disease onset. This observation might suggest an advantage to prophylactic treatment, although step uniformity, on the other hand, was improved only after disease onset (6 months) and not before it (4 months).

A striking finding was that animals treated with both compounds A and B were less apathic, more mobile and more responsive to intervention by the experimenter.

In more details: Each plot shows the effect of the indicated compounds at the age of 4 months (2 months before onset) and 6 months (at onset) on the parameters indicated. The point of reference is one time point prior to treatment initiation. Please note, since animals first treated with the compounds at 6 months of age were not injected at all before that age, they could not have been compared to animals pre-injected with vehicle. Therefore, the duration of the longitudinal studies for the cohorts first treated at the age of 6 months is shorter than that of the animals first treated at 4 months of age.

Reference is made to FIG. 11A, showing weight (in g) as a function of time after treating APBD modeling mice with vehicle, or compound A as indicated at 4 months of age (2 months before onset). Two way ANOVA with repeated measures showed that treatment was not different from vehicle ($p<0.1$). Bonferroni's multiple comparisons test showed no significant difference ($p<0.05$) between vehicle and treatment at any time point.

Figure 11B:
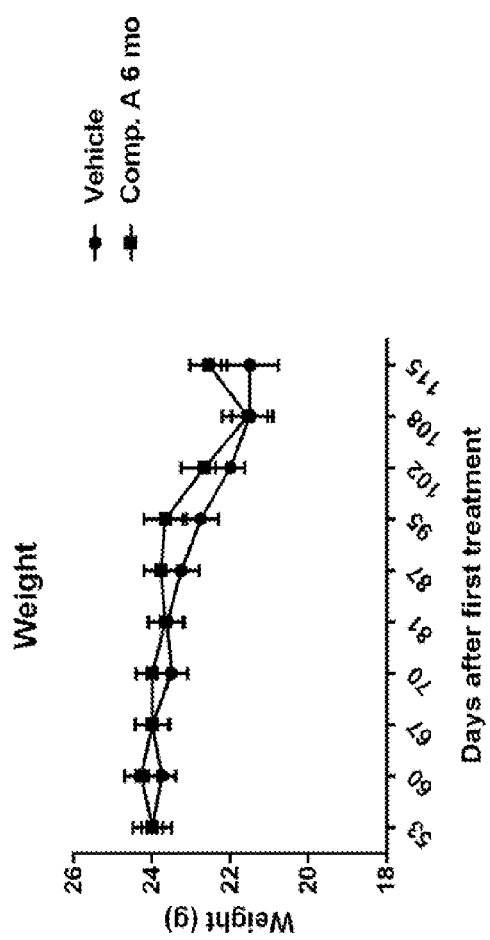

Reference is further made to FIG. 11B, showing weight (in g) as a function of time after treating APBD modeling mice with vehicle, or compound A as indicated at 6 months of age (at onset). Two way ANOVA with repeated measures showed that treatment was not different from vehicle ($p<0.1$). Bonferroni's multiple comparisons test showed no significant difference ($p<0.05$) between vehicle and treatment at any time point.

Figure 11C:
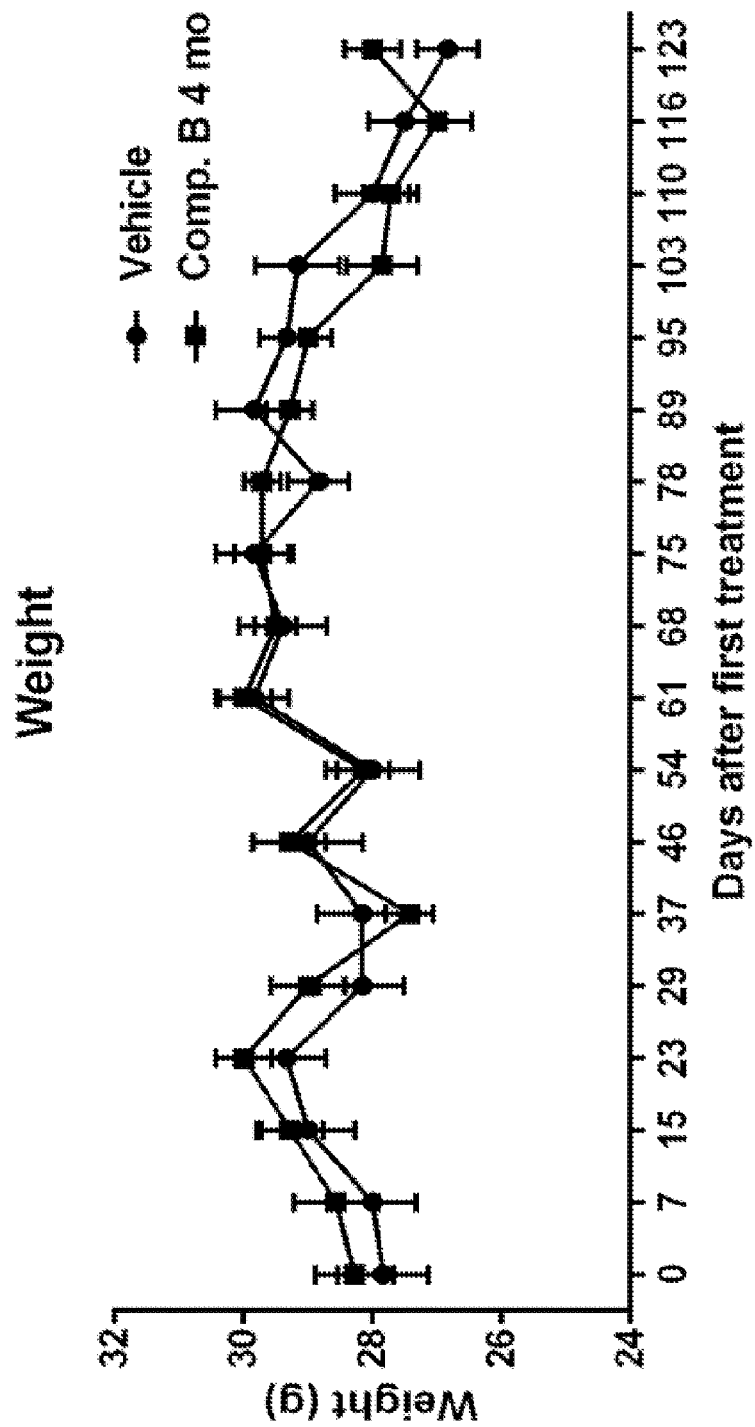

Reference is further made to FIG. 11C, showing weight (in g) as a function of time after treating APBD modeling mice with vehicle, or comp. B as indicated at 4 months of age (2 months before onset). Two way ANOVA with repeated measures showed that treatment was not different from vehicle ($p<0.1$). Bonferroni's multiple comparisons test showed no significant difference ($p<0.05$) between vehicle and treatment at any time point.

Reference is further made to FIG. 11D, showing weight (in g) as a function of time after treating APBD modeling mice with vehicle, or comp. B as indicated at 6 months of age (at onset). Two way ANOVA with repeated measures showed that treatment was significantly different from vehicle ($p<0.08$). Bonferroni's multiple comparisons test showed no significant difference ($p<0.05$) between vehicle and treatment at any time point.

Reference is further made to FIG. 12A, showing extension reflex (the degree to which the hind paws open after holding the animal from the tail) as a function of time after treating APBD modeling mice with vehicle, or comp. A as indicated at 4 months of age (2 months before onset). Two way ANOVA with repeated measures showed that treatment was different from vehicle with $p<0.09$. Bonferroni's multiple comparisons test showed no significant difference ($p<0.05$) between vehicle and treatment at any time point.

Reference is further made to FIG. 12B, showing extension reflex as a function of time after treating APBD modeling mice with vehicle, or compound A as indicated at 6 months of age (at onset). Two way ANOVA with repeated measures showed that treatment was not different from vehicle ($p<0.1$). Bonferroni's multiple comparisons test showed no significant difference ($p<0.05$) between vehicle and treatment at any time point.

Reference is further made to FIG. 12C, showing extension reflex as a function of time after treating APBD modeling mice with vehicle, or compound B as indicated at 4 months of age (2 months before onset). Two way ANOVA with repeated measures showed that treatment was not different from vehicle ($p<0.1$). Bonferroni's multiple comparisons test showed no significant difference ($p<0.05$) between vehicle and treatment at any time point.

Reference is further made to FIG. 12D, showing extension reflex as a function of time after treating APBD modeling mice with vehicle, or comp. B as indicated at 6 months of age (at onset). Two way ANOVA with repeated measures showed that treatment was not different from vehicle ($p<0.1$). Bonferroni's multiple comparisons test showed no significant difference ($p<0.05$) between vehicle and treatment at any time point.

Reference is further made to FIG. 13A, showing average front paw grip strength (the force needed to overcome front paw grip of the cage wire) as a function of time after treating APBD modeling mice with vehicle or compound A as indicated at 4 months of age (2 months before onset). Two way ANOVA with repeated measures showed that treatment was not different from vehicle ($p<0.1$). Bonferroni's multiple comparisons test showed a significant difference ($p<0.05$) between vehicle and treatment at 32 days after initiation of treatment.

Reference is further made to FIG. 13B, showing average front paw grip strength as a function of time after treating APBD modeling mice with vehicle or compound A as indicated at 6 months of age (at onset). Two way ANOVA with repeated measures showed that treatment was different from vehicle with $p<0.055$. Bonferroni's multiple comparisons test showed no significant difference ($p<0.05$) between vehicle and treatment at any time point.

Reference is further made to FIG. 13C, showing average front paw grip strength as a function as of time after treating APBD modeling mice with vehicle or compound B as indicated at 4 months of age (at onset). Two way ANOVA with repeated measures showed that treatment was different from vehicle with p<0.055. Bonferroni's multiple comparisons test showed no significant difference (p<0.05) between vehicle and treatment at any time point.

Reference is further made to FIG. 13D, showing average front paw grip strength as a function as of time after treating APBD modeling mice with vehicle or compound B as indicated at 6 months of age (at onset). Two way ANOVA with repeated measures showed that treatment was different from vehicle with p<0.1. Bonferroni's multiple comparisons test showed no significant difference (p<0.05) between vehicle and treatment at any time point.

Reference is further made to FIG. 14A, showing average gait width as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 14B, showing average gait width as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 14C, showing average gait width as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 14D, showing average gait width as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 15A, showing average gait length as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 15B, showing average gait length as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 15C showing average gait length as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 15D, showing average gait length as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 16A, showing average regularity of step distance (the Coefficient of Variance of all R–R and L–L step distances) as a function of time after treating APBD modeling mice with vehicle or comp. A as indicated at 4 months of age (2 months before onset). Two way ANOVA with repeated measures showed that treatment was significantly different from vehicle (p<0.01). Bonferroni's multiple comparisons test showed a significant difference (p<0.05) between vehicle and treatment at 81 days after treatments initiation.

Reference is further made to FIG. 16B, showing average regularity of step distance as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 16C, showing average regularity of step distance as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 16D, showing average regularity of step distance as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 17A, showing average uniformity of step alternation expressed as the mean of the absolute value of 0.5 minus the ratio of R–L distance to R–R step distance ($|0.5-(R-L/R-R)|$) and vice versa. The more uniform step alteration is, the closer the ratio (R–L/R–R) is to 0.5 and therefore the uniformity parameter approaches zero. Uniformity of step alteration is plotted as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test show a significant difference (p<0.05) between vehicle and treatment 95 days after treatment initiation.

Reference is further made to FIG. 17B, showing average uniformity of step alternation ($|0.5-(R-L/R-R)|$) as a function of time after treating APBD modeling mice with vehicle or comp. A as indicated at 6 months of age (at onset). Two way ANOVA with repeated measures showed that treatment was significantly different from vehicle (p<0.06). Bonferroni's multiple comparisons test show a significant difference (p<0.05) between vehicle and treatment 95 days after treatment initiation.

Reference is further made to FIG. 17C, showing average uniformity of step alternation (|0.5−(R−L/R−R)|) is plotted as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 17D, showing average uniformity of step alternation (|0.5−(R−L/R−R)|) as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed a significant difference (p<0.05) between vehicle and treatment at 53 days after treatment initiation.

Reference is further made to FIG. 18A, showing average duration in movement in an open field test as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Figure 18B:
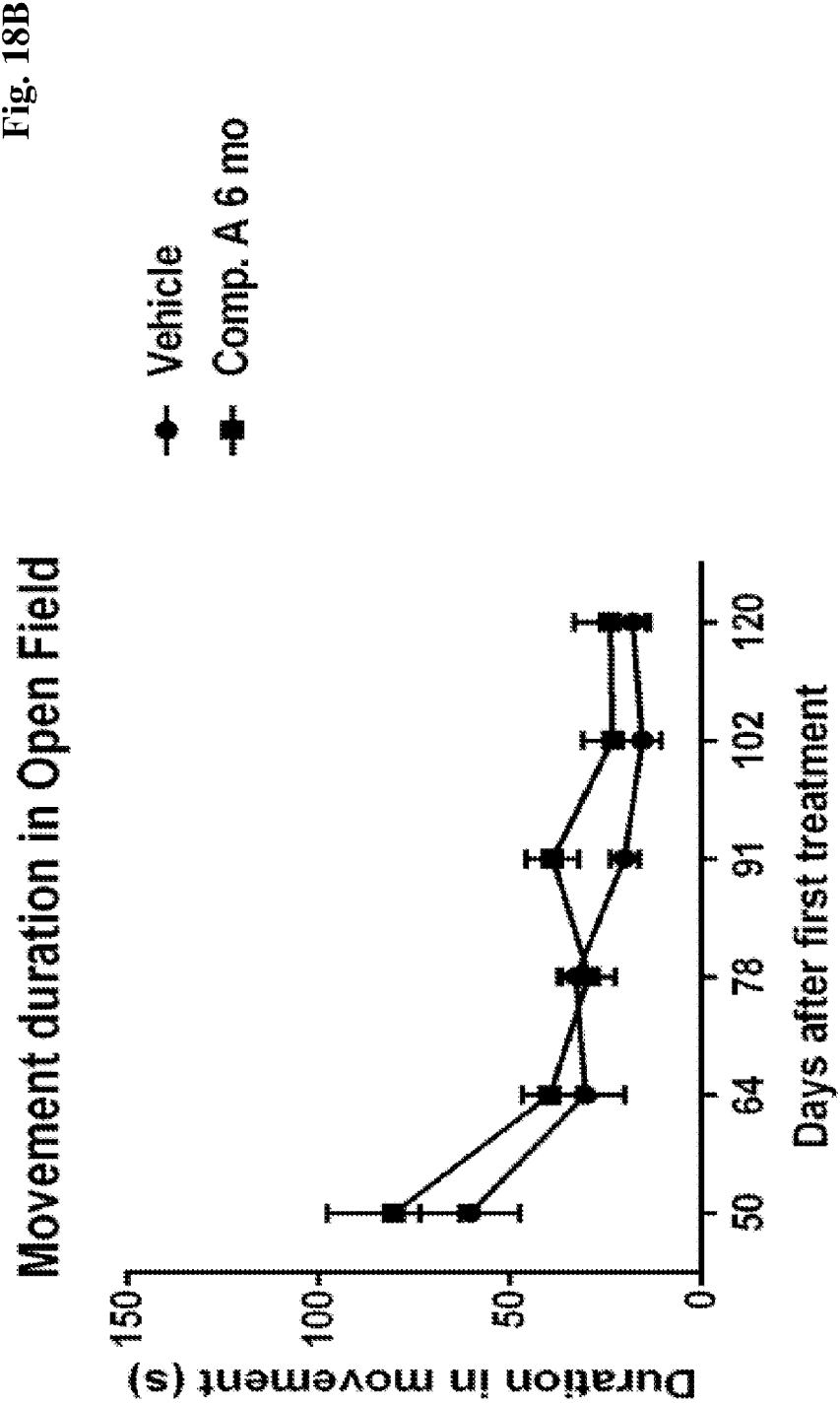

Reference is further made to FIG. 18B, showing average duration in movement in an open field test as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 18C, showing average duration in movement in an open field test as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 18D, showing average duration in movement in an open field test as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 19A, showing average latency to fall off a metal wire as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Figure 19B:
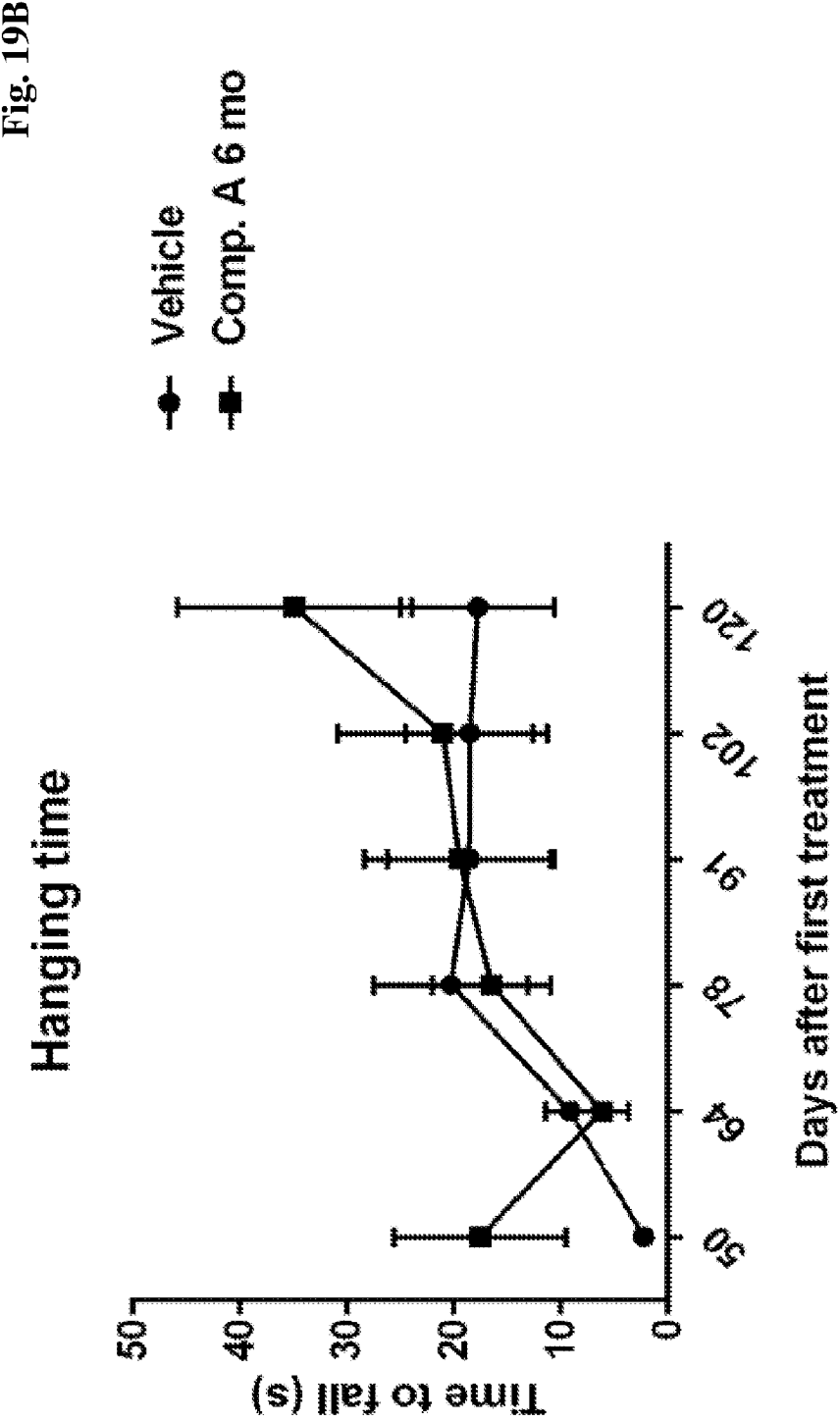

Reference is further made to FIG. 19B, showing average latency to fall off a metal wire as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Figure 19C:
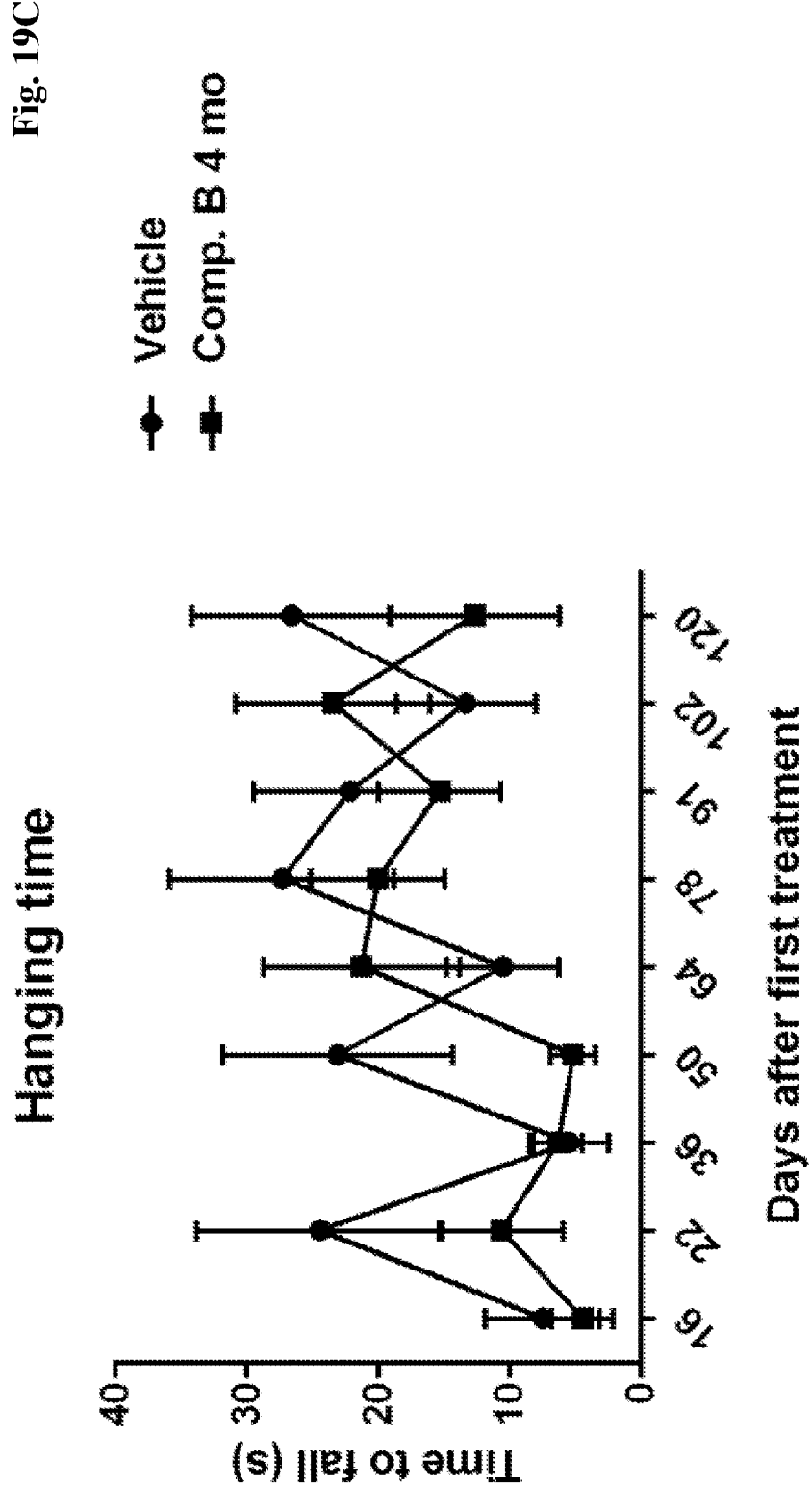

Reference is further made to FIG. 19C, showing average latency to fall off a metal wire as a function of time after treating APBD modeling mice with vehicle or comp. B as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 19D, showing average latency to fall off a metal wire as a function of time after treating APBD modeling mice with vehicle or comp. B as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 20A, showing average latency to fall off a rotating cylinder (rotarod) as a function of time after treating APBD modeling mice with vehicle or comp. A as indicated at 4 months of age (2 months before onset). Two way ANOVA with repeated measures showed that treatment was not different from vehicle (p<0.1). Bonferroni's multiple comparisons test showed no significant difference (p<0.05) between vehicle and treatment at any time.

Reference is further made to FIG. 20B, showing average latency to fall off a rotating cylinder (rotarod) as a function of time after treating APBD modeling mice with vehicle or comp. A as indicated at 6 months of age (at onset). Two way ANOVA with repeated measures showed that treatment was not different from vehicle (p<0.1). Bonferroni's multiple comparisons test showed no significant difference (p<0.05) between vehicle and treatment at any time point.

Reference is further made to FIG. 20C, showing average latency to fall off a rotating cylinder (rotarod) as a function of time after treating APBD modeling mice with vehicle or comp. B as indicated at 4 months of age (2 months before onset). Two way ANOVA with repeated measures showed that the latency to fall was shorter in treated animals (p<0.089). Bonferroni's multiple comparisons test showed that 57 days after treatment initiation latency to fall was lower in treated mice as compared to vehicle control (p<0.05).

Reference is further made to FIG. 20D, showing average latency to fall off a rotating cylinder (rotarod) as a function of time after treating APBD modeling mice with vehicle or comp. B as indicated at 6 months of age (at onset). Two way ANOVA with repeated measures showed that the latency to fall was shorter in treated animals (p<0.089). Bonferroni's multiple comparisons test showed no significant difference (p<0.05) between vehicle and treatment at any time point.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a medical condition associated with accumulation of polyglucosan bodies in a tissue of a subject, the method comprising administering to the subject a pharmaceutical composition comprising a therapeutically effective amount of a compound

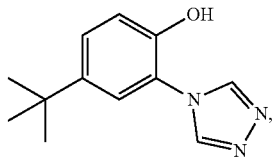 [SMILES: CC(C)(C)c1ccc(O)c(-n2cnnc2)c1]

or a pharmaceutically acceptable salt thereof.

2. The method of claim 1, wherein said medical condition is a glycogen storage disease (GSD).

3. The method of claim 2, wherein said GSD is associated with glycogen-branching enzyme deficiencies.

4. The method of claim 2, wherein said GSD is selected from the group consisting of: GSD type IV, GSD type VI, GSD type VII, GSD type IX, and GSD type XI.

5. A method of treating a medical condition selected from Adult polyglucosan body disease (APBD), Andersen disease, Forbes disease, and Danon disease, the method comprising administering to the subject a pharmaceutical composition comprising a therapeutically effective amount of a compound

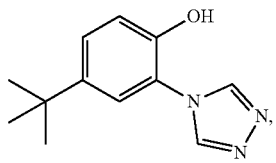 [SMILES: CC(C)(C)c1ccc(O)c(-n2cnnc2)c1]

or a pharmaceutically acceptable salt thereof.

6. The method of claim 1, wherein said subject is a human.

7. The method of claim 1, wherein the pharmaceutical composition is formulated for parenteral, mucosal, nasal or oral administration.

8. The method of claim 5, wherein said subject is a human.

9. The method of claim 5, wherein the pharmaceutical composition is formulated for parenteral, mucosal, nasal or oral administration.

10. A pharmaceutical composition comprising a therapeutically effective amount of a compound

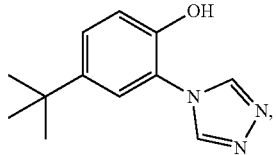 [SMILES: CC(C)(C)c1ccc(O)c(-n2cnnc2)c1]

or a pharmaceutically acceptable salt thereof, and a pharmaceutically acceptable carrier.

* * * * *